US008329175B2

(12) United States Patent
Sukhatme et al.

(10) Patent No.: US 8,329,175 B2
(45) Date of Patent: Dec. 11, 2012

(54) METHODS AND COMPOSITIONS FOR THE TREATMENT AND DIAGNOSIS OF ENDOTHELIAL CELL DISORDERS AND ANGIOGENIC DISORDERS

(75) Inventors: Vikas P. Sukhatme, Newton, MA (US); Leonard I. Zon, Boston, MA (US); Jenna Galloway, Boston, MA (US)

(73) Assignees: Beth Israel Deaconess Medical Center, Inc., Boston, MA (US); Children's Hospital Boston, Boston, MA (US)

( * ) Notice: Subject to any disclaimer, the term of this patent is extended or adjusted under 35 U.S.C. 154(b) by 509 days.

(21) Appl. No.: 11/990,803

(22) PCT Filed: Aug. 18, 2006

(86) PCT No.: PCT/US2006/032497
§ 371 (c)(1),
(2), (4) Date: Apr. 27, 2009

(87) PCT Pub. No.: WO2007/024752
PCT Pub. Date: Mar. 1, 2007

(65) Prior Publication Data
US 2009/0214572 A1 Aug. 27, 2009

Related U.S. Application Data

(60) Provisional application No. 60/711,579, filed on Aug. 26, 2005.

(51) Int. Cl.
*A61K 39/395* (2006.01)
*A61K 39/00* (2006.01)
*C07K 16/00* (2006.01)

(52) U.S. Cl. ................. 424/138.1; 424/139.1; 530/388.8

(58) Field of Classification Search ........................... None
See application file for complete search history.

(56) References Cited

U.S. PATENT DOCUMENTS

| | | | |
|---|---|---|---|
| 4,179,337 A | 12/1979 | Davis et al. | |
| 5,194,596 A | 3/1993 | Tischer et al. | |
| 5,219,739 A | 6/1993 | Tischer et al. | |
| 5,240,848 A | 8/1993 | Keck et al. | |
| 5,332,671 A | 7/1994 | Ferrara et al. | |
| 6,447,768 B1 | 9/2002 | van Zonneveld et al. | |
| 7,335,362 B2 | 2/2008 | Karumanchi et al. | |
| 7,407,659 B2 | 8/2008 | Karumanchi et al. | |
| 7,435,419 B2 | 10/2008 | Karumanchi et al. | |
| 2006/0024231 A1* | 2/2006 | Schnitzer et al. ............ | 424/1.49 |

FOREIGN PATENT DOCUMENTS

| | | |
|---|---|---|
| WO | WO 01/81634 | 11/2001 |
| WO | WO2004/008946 | 1/2004 |
| WO | WO 2004/048938 | 6/2004 |
| WO | WO2005/077007 | 8/2005 |

OTHER PUBLICATIONS

Aicher et al., "Mobilizing Endothelial Progenitor Cells," *Hypertension* 45:321-325, 2005.

Artigues et al., "Refolding Intermediates of Acid-Unfolded Mitochondrial Aspartate Aminotransferase Bind to hsp70," *J. Biol. Chem.* 272:16852-16861, 1997.
Bahary et al., "Duplicate VegfA Genes and Orthologues of the KDR Receptor Tyrosine Kinase Family Mediate Vascular Development in the Zebrafish," *Blood* 110:3627-3636, 2007.
Bdolah et al., "Angiogenic Imbalance in the Pathophysiology of Preeclampsia: Newer Insights," *Semin. Nephrol.* 24:548-556, 2004.
Beckmann et al., "Interaction of Hsp 70 with Newly Synthesized Proteins: Implications for Protein Folding and Assembly," *Science* 248:850-854, 1990.
Bedell et al., "Roundabout4 is Essential for Angiogenesis in Vivo," *Proc. Natl. Acad. Sci. U.S.A.* 102:6373-6378, 2005.
Bhatt et al., "Biomarkers for Monitoring Antiangiogenic Therapy," *Clin. Cancer Res.* 13(2 Suppl.):777s-780s, 2007.
Carmeliet et al., "Angiogenesis in Health and Disease," *Nat. Med.* 9:653-660, 2003.
Carrello et al., "Interaction of the Hsp90 Cochaperone Cyclophilin 40 with Hsc70," *Cell Stress Chaperones* 9:167181, 2004.
Charnock-Jones et al., "Identification and Localization of Alternately Spliced mRNAs for Vascular Endothelial Growth Factor in Human Uterus and Estrogen Regulation in Endometrial Carcinoma Cell Lines," *Biol. Reprod.* 48:1120-1128, 1993.
de Candia et al., "Angiogenesis Impairment in Id-Deficient Mice Cooperates with an Hsp90 Inhibitor to Completely Suppress HER2/neu-Dependent Breast Tumors," *Proc. Natl. Acad. Sci. U.S.A.* 100:12337-12342, 2003.
Durr et al., "Direct Proteomic Mapping of the Lung Microvascular Endothelial Cell Surface in Vivo and in Cell Culture," *Nat. Biotechnol.* 22:985-992, 2004.
Fujio et al., "Akt Mediates Cytoprotection of Endothelial Cells by Vascular Endothelial Growth Factor in an Anchorage-Dependent Manner," *J. Biol. Chem.* 274:16349-16354, 1999.
Gallagher et al., "Angiopoietin 2 is a Potential Mediator of High-Dose Interleukin 2-Induced Vascular Leak," *Clin. Cancer Res.* 13:2115-2120, 2007.
Gallagher et al., "Circulating Angiopoietin 2 Correlates with Mortality in a Surgical Population with Acute Lung Injury/Adult Respiratory Distress Syndrome," *Shock* 29:656-661, 2008.
Galloway et al., "Loss of gata1 but not gata2 Converts Erythropoiesis to Myelopoiesis in Zebrafish Embryos," *Dev. Cell* 8:109-116, 2005.
Gille et al., "Analysis of Biological Effects and Signaling Properties of Flt-1 (VEGFR-1) and KDR (VEGFR-2). A Reassessment Using Novel Receptor-Specific Vascular Endothelial Growth Factor Mutants," *J. Biol. Chem.* 276:3222-3230, 2001.
Giuliano Jr., "Admission Angiopoietin Levels in Children with Septic Shock," *Shock* 28:650-654, 2007.
Gong et al., "A Gene Expression Atlas of the Central Nervous System Based on Bacterial Artificial Chromosomes," *Nature* 425:917-925, 2003.
Goon et al., "Circulating Endothelial Cells, Endothelial Progenitor Cells and Endothelial Microparticles in Cancer," *Neoplasia* 8:79-88, 2006.

(Continued)

*Primary Examiner* — Doug Schultz
(74) *Attorney, Agent, or Firm* — Kristina Bieker-Brady; Clark & Elbing LLP

(57) ABSTRACT

The invention features methods and compositions for treating and preventing angiogenic disorders and endothelial cells disorders using HspA12B antagonist and HspA12B agonist compounds, respectively.

9 Claims, 15 Drawing Sheets

OTHER PUBLICATIONS

Hakimé et al., "Combination of Radiofrequency Ablation with Antiangiogenic Therapy for Tumor Ablation Efficacy," *Radiology* 244:464-470, 2007.

Hanahan et al., "The Hallmarks of Cancer," *Cell* 100:57-70, 2000.

Hartl et al., "Protein Folding in the Cell: The Role of Molecular Chaperones Hsp70 and Hsp60," *Annu. Rev. Biophys. Biomol. Struct.* 21:293-322, 1992.

Heeschen et al., "A Novel Angiogenic Pathway Mediated by Non-Neuronal Nicotinic Acetylcholine Receptors," *J. Clin. Invest.* 110:527-536, 2002.

Hu et al., "A Novel Endothelial-Specific Heat Shock Protein HspA12B is Required in Both Zebrafish Development and Endothelial Functions in Vitro," *J. Cell Sci.* 119:4117-4126, 2006.

Ingram et al., "Unresolved Questions, Changing Definitions, and Novel Paradigms for Defining Endothelial Progenitor Cells," *Blood* 106:1525-1531, 2005.

Kale et al., "Microarray Analysis of in Vitro Pericyte Differentiation Reveals an Angiogenic Program of Gene Expression," *FASEB J.* 19:270-271, 2004 (30 pages).

LeCouter et al., "Angiogenesis-Independent Endothelial Protection of Liver: Role of VEGFR-1," *Science* 299:890893, 2003.

Lee et al., "Neurophilin-1 is Required for Vascular Development and is a Mediator of VEGF-Dependent Angiogenesis in Zebrafish," *Proc. Natl. Acad. Sci. U.S.A.* 99:10470-10475, 2002.

Levine et al., "Circulating Angiogenic Factors and the Risk of Preeclampsia," *N. Engl. J. Med.* 350:672-683, 2004.

Maisonpierre et al., "Angiopoietin-2, A Natural Antagonist for Tie2 That Disrupts in Vivo Angiogenesis," *Science* 277:55-60, 1997.

Mammoto et al., "Angiopoietin-1 Requires p190 RhoGAP to Protect Against Vascular Leakage in Vivo," *J. Biol. Chem.* 282:23910-23918, 2007.

Marber et al., "Overexpression of the Rat Inducible 70-kD Heat Stress Protein in a Transgenic Mouse Increases the Resistance of the Heart to Ischemic Injury," *J. Clin. Invest.* 95:1446-1456, 1995.

Merchan et al., "In Vitro and in Vivo Induction of Antiangiogenic Activity by Plasminogen Activators and Captopril," *J. Nat. Can. Instit.* 95:388-399, 2003.

Parikh et al., "Excess Circulating Angiopoietin-2 May Contribute to Pulmonary Vascular Leak in Sepsis in Humans," *PLoS Med.* 3:0356-0370, 2006.

Plumier et al., "Transgenic Mice Expressing the Human Heat Shock Protein 70 Have Improved Post-Ischemic Myocardial Recovery," *J. Clin. Invest.* 95:1854-1860, 1995.

Snoeckx et al., "Heat Shock Proteins and Cardiovascular Pathophysiology," *Physiol. Rev.* 81:1461-1497, 2001.

Soti et al., "Aging and Molecular Chaperones," *Experimental Gerontology* 38:1037-1040, 2003.

Steagall et al., "HSPA12B is Predominantly Expressed in Endothelial Cells and Required for Angiogenesis," *Arterioscler. Thromb. Vasc. Biol.*, 26:2012-2018, 2006.

Takano et al., "Dibutyryl Cyclic Adenosine Monophosphate Protects Mice Against Tumor Necrosis Factor-Alpha-Induced Hepatocyte Apoptosis Accompanied by Increased Heat Shock Protein 70 Expression," *Cell Stress Chaperones* 3:109-117, 1998.

Tang et al., "A Critical Role for Calponin 2 in Vascular Development," *J. Biol. Chem.* 281:6664-6672, 2006.

Thadhani et al., "Insulin Resistance and Alterations in Angiogenesis: Additive Insults that may Lead to Preeclampsia," *Hypertension* 43:988-992, 2004.

Tischer et al., "The Human Gene for Vascular Endothelial Growth Factor. Multiple Protein Forms are Encoded Through Alternative Exon Splicing," *J. Biol. Chem.* 266:11947-11954, 1991.

Wolf et al., "Preeclampsia and Future Cardiovascular Disease: Potential Role of Altered Angiogenesis and Insulin Resistance," *J. Clin. Endocrinol. Metab.* 89:6239-6243, 2004.

Berruguete et al., "Heat Shock Protein of Molecular Weight 70 (HSP70) is Involved in the Survival Effect of Endogenous and Exogenous Vascular Endothelial Growth Factor (VEGF) in Endothelial Cells (EC) by a Mechanism that Involves the VEGF Receptor 2 (VEGFR2) and PI3/AKT," *New Insights into Renal and Vascular Inflamation*, vol. 196., Jun. 6, 2005, Abstract M025.

Han et al., "Two Hsp70 Family Members Expressed in Atherosclerotic Lesions," *Proc. Natl. Acad. Sci. U.S.A.* 100:1256-1261, 2003.

Hannon et al., "Unlocking the Potential of the Human Genome with RNA Interference," *Nature* 431:371-378, 2004.

International Search Report for PCT/US2006/032497, completed Jun. 23, 2007, mailed Sep. 21, 2007.

International Preliminary Report on Patentability for PCT/US2006/032497, issued Feb. 26, 2008.

Written Opinion of the International Searching Authority for PCT/US2006/032497, mailed Sep. 21, 2007.

\* cited by examiner

Figure 11A

HspA12B amino acid sequence

MLAVPEMGLQGLYIGSSPERSPVPSPPGSPRTQESCGIAPLTPSQSPKPEVRA
PQQASFSVVVAIDFGTTSSGYAFSFASDPEAIHMMRKWEGGDPGVAHQKTPT
CLLLTPEGAFHSFGYTARDYYHDLDPEEARDWLYFEKFKMKIHSATDLTLKTQL
EAVNGKTMPALEVFAHALRFFREHALQELREQSPSLPEKDTVRWVLTVPAIWK
QPAKQFMREAAYLAGLVSRENAEQLLIALEPEAASVYCRKLRLHQLLDLSGRAP
GGGRLGERRSIDSSFRQAREQLRRSRHSRTFLVESGVGELWAEMQAGDRYVV
ADCGGGTVDLTVHQLEQPHGTLKELYKASGGPYGAVGVDLAFEQLLCRIFGED
FIATFKRQRPAAWVDLTIAFEARKRTAGPHRAGALNISLPFSFIDFYRKQRGHNV
ETALRRSSVNFVKWSSQGMLRMSCEAMNELFQPTVSGIIQHIEALLARPEVQG
VKLLFLVGGFAESAVLQHAVQAALGARGLRVVVPHDVGLTILKGAVLFGQAPGV
VRVRRSPLTYGVGVLNRFVPGRHPPEKLLVRDGRWCTDVFERFVAAEQSVAL
GEEVRRSYCPARPGQRRVLINLYCCAAEDARFITDPGVRKCGALSLELEPADC
GQDTAGAPPGRREIRAAMQFGDTEIKVTAVDVSTNRSVRASIDFLSN

Figure 11A (continued)

HspA12B nucleic acid sequence

```
   1 gcggccgccg cagcgggcac ggccaacgag ctgcgggccc gggatcgcgg cggctggacg
  61 gggctggagc tgtcgggagg gcggagctac agggcctgca aggatgttgg ctgtcccgga
 121 gatgggcctg cagggggctgt acatcggctc cagcccggag cggtccccag tgcctagccc
 181 acccggctcc ccgaggaccc aggaaagctg cggcattgcc cccctcacac cctcgcagtc
 241 tccaaaaccc gaggtccgag ccccccagca ggcctccttc tctgtggtgg tggccattga
 301 cttcggcacc acgtctagtg gctatgcttt cagctttgcc agtgaccctg aggccatcca
 361 catgatgagg aaatggaagg gcggagaccc gggcgtggcc caccagaaga ccccgacctg
 421 cctgctgctg actccggagg gcgccttcca cagctttggc tacaccgccc gcgattacta
 481 ccatgacctg gaccccgaag aggcgcggga ctggctctac ttcgagaagt tcaagatgaa
 541 gatccacagc gccacggatc tcaccttgaa gacccagcta gaggcagtaa atggaaagac
 601 gatgcccgcc ctggaggtgt tcgcccatgc cctgcgcttc tcagggagc acgcccttca
 661 ggagctgagg gagcagagcc catcgctgcc agagaaggac actgtgcgct gggtgttgac
 721 ggtgcctgcc atctggaaac agccagccaa gcagttcatg cgggaggctg cctacctggc
 781 tggactagtg tcccgagaga atgcagagca gctactcatc gccctggagc ccgaggccgc
 841 ctcggtatac tgccgcaagc tgcgcctgca ccagctcctg gacctgagtg gccgggcccc
 901 aggtggtggg cgcctgggtg agcgccgctc catcgactcc agcttccgtc aggctcggga
 961 gcagctgcga aggtcccgcc acagccgcac gttcctggtg gagtcaggcg taggagagct
1021 gtgggcagag atgcaagcag gagaccgcta cgtggtggcc gactgcggcg gaggcaccgt
1081 ggacctgacg gtgcaccagc tggagcagcc ccatggcacc ctcaaggagc tctacaaggc
1141 atctgggggc ccttatggcg cggtgggcgt ggacctggcc ttcgagcagc tgctgtgccg
1201 catcttcggc gaggacttca tgccaccctt caaaaggcaa cggccggcag cctgggtaga
1261 tctgaccatc gccttcgagg ctcgcaagcg cactgctggc ccacaccgtg caggggcgct
1321 caacatctcg ctgcccttct ccttcattga cttctaccgc aagcagcggg gccacaacgt
1381 ggagaccgct ctgcgcagga gcagcgtgaa cttcgtgaag tggtcctcac agggggatgct
1441 ccgaatgtct tgtgaagcca tgaacgagct ctttcagccc accgtcagcg ggatcatcca
1501 gcacatagag gccctgctgg cacggccgga ggtgcagggt gtgaagctgc tgttcctagt
1561 gggcggcttc gccgagtcag cggtgctgca gcacgcggtg caggcggcgc tgggcgcccg
1621 cggtctgcgt gtcgtggtcc cgcacgacgt gggcctcacc atcctcaaag gcgcggtgct
1681 gttcggccag gcgccgggcg tggtgcgggt ccgccgctcg ccgctcacct atggcgtggg
1741 cgtgctcaac cgctttgtgc ctgggcgcca cccgccgaa aagctgctgg ttcgcgacgg
1801 ccgccgctgg tgcaccgacg tcttcgagcg cttcgtggcc gccgagcagt cggtggccct
1861 gggcgaggag gtgcggcgca gctactgccc ggcgcgtccc ggccagcggc gcgtactcat
1921 caacctgtac tgctgcgcgg cagaggatgc gcgcttcatc accgaccccg gcgtgcgcaa
1981 atgcggcgcg ctcagcctcg agcttgagcc cgccgactgc ggccaggaca ccgccggcgc
2041 gcctcccggc cgccgcgaga tccgcgccgc catgcagttt ggcgacaccg aaattaaggt
2101 caccgccgtc gacgtcagca ccaatcgctc cgtgcgcgcg tccatcgact tctttccaa
2161 ctgagggcgc gccggcgcgg tgccagcgcc gtctgcccgg ccccgccctc tttcggttca
2221 ggggcctgcg gagcgggttg gggcggggga acgatagtt ctgcagtctg cgcctttcca
2281 cgccctccag ccccggggga gataaggtca tgggagagtg ggtgggaca cacccagaga
2341 ctggctttgg gattgggcac tggtccgctg actccaggc tgaagggacc cgccaaggac
2401 tgaacgggta agagaagagg tttgcaagac agagcgcgca gcccggcaag gggcatgtga
2461 ccccgaagga agaacgcaac agaagagtcc tggtctgaac ttggccgagt aggggtgggg
2521 gtgggatggc aggaggagcc gcaggaggaa ggaggttgtg cagggtctgg acctgcaggg
2581 ctgaagttca ctcatcgacc gactcagccc caaccgggag ccaggcagaa aaaccctgtg
2641 ccgtaggaaa gtgactggaa gtggactcca gagggacagg tgtggtggca cagtcctggt
2701 gtggtgctga ccacccaaat atgactgtga attgtggaaa gggcagtaga tctctaatgt
```

Figure 11A (continued)

HspA12B nucleic acid sequence (continued)

```
2761 ggaggtggga acattattgt ggtggaggca attatgaggg tagcatttct ttcgagacaa
2821 aacacccgtc tgggaaggcc ccaaggtcag cttatgaagg accccacttg caccccaccc
2881 cagccatgga agagcagctg gagggtggat ggggaggcca gagggagcaa tgaggggtgg
2941 tcccagctct gctattgact cggtatgcct ttaggacatt ctcttaccgc tcatgggcct
3001 cagtttccta aagtgtgaaa tgtcaggcac ttccctctaa ctggcatgca acagccccac
3061 ctgcctgaga gccctgaggt gacaataaaa catttatgct caaggggaa
```

```
  1 MADVLQLSIN SLQVP--GED KSDSTSPSGS PFPSRNECSL TPLTPSPSPR TEVRPRLARP EYVVVAIDFG TTSSGYAFSF Zebrafish
  1 MLAVPEMGLQ GLYI-GSSPE RSPVPSPPGS PR-TQESCGI APLTPSQSPK PEVRAPQQAS FSVVVAIDFG TTSSGYAFSF Human
  1 MLIVPEMGLQ GLYIS-SSPE RSPVPSPPGS PR-TQESCGI APLTPSQSPK PEARALQQAS FSVVVAIDFG TTSSGYAFSF Mouse
  1 MLTVPEMGLQ GLYIS-SSPE RSPVPSPFGS PR-TQESCGI APLTPSQSPK PEVRAPQRAS FSVVVAIDFG TTSSGYAFSF Rat 79 IEDPEITHMM RRWEGGDFGV ANQKSPTCLI LTEDLRFHSF GFAARDSYHD LDPEEARHNL KEDKFKMKIH STSDLIMETE Zebrafish
 79 ASDPEAIHMM RKWEGGDFGV AHQKTPTCLI LTPEGAFHSF GYTARDYYHD LDPEEARDNL KFEKFKMKIH SAIDLTLKTQ Human
 79 ASDPEAIHMM RKWEGGDFGV AHQKTPTCLI LTPEGIFHSF GYTARDYYHD LDPEEARDNL KFEKFKMKIH SAIDLTLKTQ Mouse
 79 ATDPEAIHMM RKWEGGDFGV AHQKTPTCLI LTPEGIFHSF GYTARDYYHD LDPEEARDNL KFEKFKMKIH SAIDLTLKTQ Rat 159 LESVSGRRVQ ALEVFAHALR FFRFHALK-- ---------- ---------- ---EVKDQSS SVLEGNEVRW VLTVPAVWRQ Zebrafish
159 LEAVNGKTMP ALEVFAHALR FFREHAL--- ---------- ---------- --QELREQSE SLPEKDTVRV VLTVPAIWKQ Human
159 LEAVNGKKML ALEVFAHALR FFKEHALQ-- ---------- ---------- ---ELREQSE CMLEKGAVRW VLTVPAIWKQ Mouse
159 LEAVNGKKML ALEVFAHALR FFKEHALQLP ERAENASDQL SPYGPFPTPP TLQELREQSE CMLEKDAVRW VLTVPAIWKQ Rat 214 PAKQFMPEAA VL-------- ---------- ------AGH VPPDSPEQHL TALEPEAASI KCRKLRLHQV TDLSQRPVTN Zebrafish
214 PAKQFMREAA VL-------- ---------- ------AGH VSEFNAEQII TALEPEAASV KCRKLRLHQI LDLSCR-APG Human
214 PAKQFMREAA VL-------- ---------- ------AGL VSREDAEKLL TALEPEAASV KCRKLRLHQI MDLSSR-TAG Mouse
239 PAKQFMREAA VLKRWEQPDP RAPSYMTVYG AGHTYPQAGI VSREDAEKLL TALEPEAASV KCRKLRLHQI MDLSSR-TAG Rat 269 GFDIDGSRPF DSSFRQAREQ LFRAPHSRTE LVESGTGELW SEMQTGDFYI VADCGGGTVD LTVHQLEQFQ GTLKELYKAS Zebrafish
268 GGRIGERRSI DSSFRQAREQ LRRSRHSFTE LVESGVGELW AEMQAGDRIV VADCGGGTVB LTVHQLEQFH GTLKELYKAS Human
268 RGRLGERRSL DSSFRHAREQ LFRSRHSRTE LVEAGVGELW AEMQEGDRYM VADCGGGTVB LTVHQLEQPH GTLKELYKAS Mouse
318 GGRLGERRSI DSSFRHAREQ LRRSRHSRTE LVESGVGELW SEMQEGDRYM VADCGGGTVB GTLKELYKAS LTVHQLEQPH Rat 349 GGPYGAVGVD LAFEIMLCQI KGIDFIDSFK AKRPAAWVDL ITAFEARKRT AAEGRANILN ISLPFSFIDR YKQHEGQSVE Zebrafish
348 GGPYGAVGVD LAFEQLLCRI FGEDFIATFK RQRPAAWVDL ITAFEARKRT AGPHRAGALN ISLPFSFIDF YRKQRGHNVE Human
348 GGPYGAVGVD LAFEQLLCRI FGEDFIAKFK RQRPAAWVDL ITAFEARKRT AGPHRAGALN ISLPFSFIDF YRKQRGHNVE Mouse
398 GGPYGAVGVD LAFEQLLCRI FGEDFIAKFK RQRPAAWVDI ITAFEARKRT AGPHRAGALN ISLPFSFIDE YRKQRGHNVE Rat 429 TALRKSNMNF IKWSSCGMLR LSTEATNELF QPTINNITKI EENVMQEEEV KCVRPLFLVG GFAESEMLQR AIQNTIG-RN Zebrafish
428 TALKRSSVNF VKWSSCGVLR MSCEANNELF QPTVSGIIQR IPALIARDFV QGVKLLFLVG GFAESAVLQH AVQAALGARS Human
428 TALKRSSVNL VKNSSCGMLR MSCEAMMELF QPIVSGIIQR IEMLLAKPRV OGVKLLRIVG GFAESAVLQH AVQEAIGTRG Mouse
478 TALKRSSVNF VKWSSCGMLR MSCEANNELF QPTVSGIIQR IEMLLAKPEV OGVKLLFLVG GFAESAVLQH AVQEAIGNRG Rat 508 CMILERHVG TTILKGAVLF GLDFTVRVE KCPLTYGVGV LMRFVEGRHE HDKLLIKDGR EMCTDILDRF VSVDQSVALG Zebrafish
508 LRVVVPHDVG LTILKGAVLF CQAPGVVRVF RSPLITYGVGV LMRFVPGRHF PEKLLVRDGR RMCIDVFERF VAAEQSVALG Human
508 LRVVVPHDVG LTILKGAVLF CQAPGYVRVF NSPLIYGVGV LMRFVPGHHE PEKLLVRDGR RMCTDVFERF VAAEQSVALG Mouse
558 LRVVVPHDVG LTILKGAVLF CQAPGYVRVF RSPLIYGVGV LMRFVPGHHE PEKLLVRDGR RMCTDVFERF VAAEQSVALG Rat 588 EVVRSYTPA FMGQRKIIEN IKCSDTDDIT YSDFGVRKG GATTIDILES GEASASTGDN DKGSAFERRE LRTTMQFGII Zebrafish
588 EEVKRSYCPA RPGORRVLIN LYCCAAEDAR FTTDPGVRKG GALSLELE-- ----BADCGQD TAGAPFGRRE LRAAMQFGII Human
588 EEVKRSYCPA RFGQRRVLIN LYCCAAEDAR FTTDPGVRKG GALSLELE-- ----EEGC-PE NIGTSPSRRE LRAAMQFGII Mouse
638 EEVKRSYCPA RFGQRRVLIN LYCCAAEDAR FTTDPGVRKC GALSLELE-- ----EEGS-PE NIGTSPSRRE LRAAMQFGII Rat 668 EIKVTAVDVA IGRLVRASID FLSN Zebrafish
663 EIKVTAVDVS INRSVRASID FLSN Human
662 EIKVTAVDVS INRSVRAAID FLSN Mouse
712 EIKVTAVDVS INRSVRAAID FLSN Rat
```

C

| Human HspA12B | Mouse HspA12B | Rat HspA12B | Chimpanzee HspA12B | Human HspA12A | |
|---|---|---|---|---|---|
| 0.694 | 0.682 | 0.643 | 0.509 | 0.324 | Zebrafish HspA12B |
| | 0.933 | 0.875 | 0.739 | 0.321 | Human HspA12B |
| | | 0.917 | 0.691 | 0.317 | Mouse HspA12B |
| | | | 0.678 | 0.307 | Rat HspA12B |
| | | | | 0.278 | Chimpanzee HspA12B |

D

SEQUENCE LISTING

```
<160> NUMBER OF SEQ ID NOS: 25

<210> SEQ ID NO 1
<211> LENGTH: 685
<212> TYPE: PRT
<213> ORGANISM: Homo sapiens

<400> SEQUENCE: 1

Met Leu Ala Val Pro Glu Met Gly Leu Gln Gly Leu Tyr Ile Gly Ser
1               5                   10                  15

Ser Pro Glu Arg Ser Pro Val Pro Ser Pro Pro Gly Ser Pro Arg Thr
            20                  25                  30

Gln Glu Ser Cys Gly Ile Ala Pro Leu Thr Pro Ser Gln Ser Pro Lys
        35                  40                  45

Pro Glu Val Arg Ala Pro Gln Gln Ala Ser Phe Ser Val Val Val Ala
    50                  55                  60

Ile Asp Phe Gly Thr Thr Ser Ser Gly Tyr Ala Phe Ser Phe Ala Ser
65                  70                  75                  80

Asp Pro Glu Ala Ile His Met Met Arg Lys Trp Glu Gly Gly Asp Pro
```

```
                        85                  90                  95
Gly Val Ala His Gln Lys Thr Pro Thr Cys Leu Leu Leu Thr Pro Glu
                100                 105                 110
Gly Ala Phe His Ser Phe Gly Tyr Thr Ala Arg Asp Tyr Tyr His Asp
                115                 120                 125
Leu Asp Pro Glu Glu Ala Arg Asp Trp Leu Tyr Phe Glu Lys Phe Lys
            130                 135                 140
Met Lys Ile His Ser Ala Thr Asp Leu Thr Leu Lys Thr Gln Leu Glu
145                 150                 155                 160
Ala Val Asn Gly Lys Thr Met Pro Ala Leu Glu Val Phe Ala His Ala
                165                 170                 175
Leu Arg Phe Phe Arg Glu His Ala Leu Gln Glu Leu Arg Glu Gln Ser
            180                 185                 190
Pro Ser Leu Pro Glu Lys Asp Thr Val Arg Trp Val Leu Thr Val Pro
        195                 200                 205
Ala Ile Trp Lys Gln Pro Ala Lys Gln Phe Met Arg Glu Ala Ala Tyr
        210                 215                 220
Leu Ala Gly Leu Val Ser Arg Glu Asn Ala Glu Gln Leu Leu Ile Ala
225                 230                 235                 240
Leu Glu Pro Glu Ala Ala Ser Val Tyr Cys Arg Lys Leu Arg Leu His
                245                 250                 255
Gln Leu Leu Asp Leu Ser Gly Arg Ala Pro Gly Gly Arg Leu Gly
            260                 265                 270
Glu Arg Arg Ser Ile Asp Ser Ser Phe Arg Gln Ala Arg Glu Gln Leu
        275                 280                 285
Arg Arg Ser Arg His Ser Arg Thr Phe Leu Val Glu Ser Gly Val Gly
    290                 295                 300
Glu Leu Trp Ala Glu Met Gln Ala Gly Asp Arg Tyr Val Val Ala Asp
305                 310                 315                 320
Cys Gly Gly Gly Thr Val Asp Leu Thr Val His Gln Leu Glu Gln Pro
                325                 330                 335
His Gly Thr Leu Lys Glu Leu Tyr Lys Ala Ser Gly Gly Pro Tyr Gly
            340                 345                 350
Ala Val Gly Val Asp Leu Ala Phe Glu Gln Leu Leu Cys Arg Ile Phe
        355                 360                 365
Gly Glu Asp Phe Ile Ala Thr Phe Lys Arg Gln Arg Pro Ala Ala Trp
        370                 375                 380
Val Asp Leu Thr Ile Ala Phe Glu Ala Arg Lys Arg Thr Ala Gly Pro
385                 390                 395                 400
His Arg Ala Gly Ala Leu Asn Ile Ser Leu Pro Phe Ser Phe Ile Asp
                405                 410                 415
Phe Tyr Arg Lys Gln Arg Gly His Asn Val Glu Thr Ala Leu Arg Arg
            420                 425                 430
Ser Ser Val Asn Phe Val Lys Trp Ser Ser Gln Gly Met Leu Arg Met
        435                 440                 445
Ser Cys Glu Ala Met Asn Glu Leu Phe Gln Pro Thr Val Ser Gly Ile
    450                 455                 460
Ile Gln His Ile Glu Ala Leu Leu Ala Arg Pro Glu Val Gln Gly Val
465                 470                 475                 480
Lys Leu Leu Phe Leu Val Gly Gly Phe Ala Glu Ser Ala Val Leu Gln
                485                 490                 495
His Ala Val Gln Ala Ala Leu Gly Ala Arg Gly Leu Arg Val Val Val
            500                 505                 510
```

```
Pro His Asp Val Gly Leu Thr Ile Leu Lys Gly Ala Val Leu Phe Gly
        515                 520                 525
Gln Ala Pro Gly Val Val Arg Val Arg Arg Ser Pro Leu Thr Tyr Gly
        530                 535                 540
Val Gly Val Leu Asn Arg Phe Val Pro Gly Arg His Pro Pro Glu Lys
545                 550                 555                 560
Leu Leu Val Arg Asp Gly Arg Trp Cys Thr Asp Val Phe Glu Arg Phe
                565                 570                 575
Val Ala Ala Glu Gln Ser Val Ala Leu Gly Glu Val Arg Arg Ser
            580                 585                 590
Tyr Cys Pro Ala Arg Pro Gly Gln Arg Val Leu Ile Asn Leu Tyr
        595                 600                 605
Cys Cys Ala Ala Glu Asp Ala Arg Phe Ile Thr Asp Pro Gly Val Arg
        610                 615                 620
Lys Cys Gly Ala Leu Ser Leu Glu Leu Glu Pro Ala Asp Cys Gly Gln
625                 630                 635                 640
Asp Thr Ala Gly Ala Pro Pro Gly Arg Arg Glu Ile Arg Ala Ala Met
                645                 650                 655
Gln Phe Gly Asp Thr Glu Ile Lys Val Thr Ala Val Asp Val Ser Thr
            660                 665                 670
Asn Arg Ser Val Arg Ala Ser Ile Asp Phe Leu Ser Asn
        675                 680                 685

<210> SEQ ID NO 2
<211> LENGTH: 3109
<212> TYPE: DNA
<213> ORGANISM: Homo sapiens

<400> SEQUENCE: 2
gcggccgccg cagcgggcac ggccaacgag ctgcgggccc gggatcgcgg cggctggacg      60
gggctggagc tgtcgggagg gcggagctac agggcctgca aggatgttgg ctgtcccgga     120
gatgggcctg caggggctgt acatcggctc cagcccggag cggtccccag tgcctagccc     180
acccggctcc ccgaggaccc aggaaagctg cggcattgcc ccctcacac cctcgcagtc      240 tccaaaaccc gaggtccgag ccccccagca ggcctccttc tctgtggtgg tggccattga     300
cttcggcacc acgtctagtg ctatgctttt cagctttgcc agtgaccctg aggccatcca     360
catgatgagg aaatgggagg cggagaccc gggcgtggcc accagaaga ccccgacctg       420 cctgctgctg actccggagg cgccttcca cagctttggc tacaccgccc gcgattacta      480
ccatgacctg gaccccgaag aggcgcggga ctggctctac ttcgagaagt tcaagatgaa     540
gatccacagc gccacggatc tcaccttgaa gacccagcta gaggcagtaa atggaaagac     600
gatgcccgcc ctggaggtgt cgcccatgc cctgcgcttc ttcagggagc acgcccttca     660
ggagctgagg gagcagagcc atcgctgcc agagaaggac actgtgcgct gggtgttgac      720
ggtgcctgcc atctggaaac agccagccaa gcagttcatg cgggaggctg cctacctggc     780
tggactagtg tcccgagaga atgcagagca gctactcatc gccctggagc cgaggccgc      840 ctcggtatac tgccgcaagc tgcgcctgca ccagctcctg acctgagtg gccgggcccc     900 aggtggtggg cgcctgggtg agcgccgctc catcgactcc agcttccgtc aggctcggga     960
gcagctgcga aggtcccgcc acagccgcac gttcctggtg gagtcaggcg taggagagct    1020
gtgggcagag atgcaagcag gagaccgcta cgtggtggcc gactgcggcg gaggcaccgt    1080 ggaccctgacg tgcaccagc tggagcagcc ccatggcacc ctcaaggagc tctacaaggc    1140
atctgggggc ccttatggcg cggtgggcgt ggacctggcc ttcgagcagc tgctgtgccg    1200
```

```
catcttcggc gaggacttca tcgccacctt caaaaggcaa cggccggcag cctgggtaga    1260
tctgaccatc gccttcgagg ctcgcaagcg cactgctggc ccacaccgtg cagggcgct     1320 caacatctcg ctgcccttct ccttcattga cttctaccgc aagcagcggg gccacaacgt    1380
ggagaccgct ctgcgcagga gcagcgtgaa cttcgtgaag tggtcctcac agggatgct    1440 ccgaatgtct tgtgaagcca tgaacgagct ctttcagccc accgtcagcg ggatcatcca    1500
gcacatagag gccctgctgg cacggccgga ggtgcagggt gtgaagctgc tgttcctagt    1560
gggcggcttc gccgagtcag cggtgctgca gcacgcggtg caggcggcgc tgggcgcccg    1620
cggtctgcgt gtcgtggtcc cgcacgacgt gggcctcacc atcctcaaag gcgcggtgct    1680
gttcggccag gcgccgggcg tggtgcgggt ccgccgctcg ccgctcacct atggcgtggg    1740
cgtgctcaac cgctttgtgc ctgggcgcca cccgcccgaa aagctgctgg ttcgcgacgg    1800
ccgccgctgg tgcaccgacg tcttcgagcg cttcgtggcc gccgagcagt cggtggccct    1860
gggcgaggag gtgcggcgca gctactgccc ggcgcgtccc ggccagcggc gcgtactcat    1920
caacctgtac tgctgcgcgg cagaggatgc gcgcttcatc accgaccccg gcgtgcgcaa    1980
atgcggcgcg ctcagcctcg agcttgagcc cgccgactgc ggccaggaca ccgcggcgc     2040 gcctccggc cgccgcgaga tccgcgccgc catgcagttt ggcgacaccg aaattaaggt     2100
caccgccgtc gacgtcagca ccaatcgctc cgtgcgcgcg tccatcgact ttctttccaa    2160
ctgagggcgc gccggcgcgg tgccagcgcc gtctgcccgg ccccgccctc tttcggttca    2220
ggggcctgcg gagcgggttg gggcggggga acgatagtt ctgcagtctg cgcctttcca    2280
cgccctccag ccccggggga gataaggtca tgggagagtg ggtggggaca cacccagaga    2340
ctggctttgg gattgggcac tggtccgctg actgccaggc tgaagggacc cgccaaggac    2400
tgaacgggta agagaagagg tttgcaagac agagcgcgca gcccggcaag gggcatgtga    2460 cccccgaagga agaacgcaac agaagagtcc tggtctgaac ttggccgagt aggggtgggg   2520
gtgggatggc aggaggagcc gcaggaggaa ggaggttgtg cagggtctgg acctgcaggg    2580
ctgaagttca ctcatcgacc gactcagccc caaccgggag ccaggcagaa aaaccctgtg    2640
ccgtaggaaa gtgactggaa gtggactcca gagggacagg tgtggtggca cagtcctggt    2700
gtggtgctga ccacccaaat atgactgtga attgtggaaa gggcagtaga tctctaatgt    2760
ggaggtggga acattattgt ggtggaggca attatgaggg tagcatttct ttcgagacaa    2820 aacaccgtc tgggaaggcc ccaaggtcag cttatgaagg accccacttg cacccacccc    2880
cagccatgga agagcagctg gagggtggat ggggaggcca gagggagcaa tgagggttgg   2940
tcccagctct gctattgact cggtatgcct ttaggacatt ctcttaccgc tcatgggcct    3000
cagtttccta aagtgtgaaa tgtcaggcac ttccctctaa ctggcatgca acagccccac    3060
ctgcctgaga gccctgaggt gacaataaaa catttatgct caaggggaa                3109

<210> SEQ ID NO 3
<211> LENGTH: 691
<212> TYPE: PRT
<213> ORGANISM: Zebrafish

<400> SEQUENCE: 3

Met Ala Asp Val Leu Gln Leu Ser Ile Asn Ser Leu Gln Val Pro Gly
1               5                   10                  15

Glu Asp Lys Ser Asp Ser Thr Ser Pro Ser Gly Ser Pro Phe Pro Ser
            20                  25                  30

Arg Asn Glu Cys Ser Ile Thr Pro Leu Thr Pro Ser Pro Ser Pro Arg
```

```
                  35                  40                  45
Thr Glu Val Arg Pro Arg Leu Ala Arg Pro Phe Tyr Val Val Ala
 50                  55                  60

Ile Asp Phe Gly Thr Thr Ser Ser Gly Tyr Ala Phe Ser Phe Ile Glu
 65                  70                  75                  80

Asp Pro Glu Thr Ile His Met Met Arg Arg Trp Glu Gly Gly Asp Pro
                     85                  90                  95

Gly Val Ala Asn Gln Lys Ser Pro Thr Cys Leu Leu Leu Thr Pro Asp
                100                 105                 110

Leu Arg Phe His Ser Phe Gly Phe Ala Ala Arg Asp Ser Tyr His Asp
                115                 120                 125

Leu Asp Pro Glu Glu Ala Arg His Trp Leu Tyr Phe Asp Lys Phe Lys
130                 135                 140

Met Lys Ile His Ser Thr Ser Asp Leu Thr Met Glu Thr Glu Leu Glu
145                 150                 155                 160

Ser Val Ser Gly Arg Arg Val Gln Ala Ile Glu Val Phe Ala His Ala
                165                 170                 175

Leu Arg Phe Phe Arg Glu His Ala Leu Lys Glu Val Lys Asp Gln Ser
                180                 185                 190

Ser Ser Val Leu Glu Gly Asn Glu Val Arg Trp Val Ile Thr Val Pro
                195                 200                 205

Ala Val Trp Arg Gln Pro Ala Lys Gln Phe Met Arg Glu Ala Ala Tyr
                210                 215                 220

Leu Ala Gly Leu Val Pro Pro Asp Ser Pro Glu Gln Leu Leu Ile Ala
225                 230                 235                 240

Leu Glu Pro Glu Ala Ala Ser Ile Tyr Cys Arg Lys Leu Arg Leu His
                245                 250                 255

Gln Val Thr Asp Leu Ser Gln Arg Pro Val Thr Asn Gly Phe Asp Ile
                260                 265                 270

Asp Gly Ser Arg Pro Phe Asp Ser Ser Phe Arg Gln Ala Arg Glu Gln
                275                 280                 285

Leu Arg Arg Ala Arg His Ser Arg Thr Phe Leu Val Glu Ser Gly Thr
290                 295                 300

Gly Glu Leu Trp Ser Glu Met Gln Thr Gly Asp Arg Tyr Ile Val Ala
305                 310                 315                 320

Asp Cys Gly Gly Gly Thr Val Asp Leu Thr Val His Gln Ile Glu Gln
                325                 330                 335

Pro Gln Gly Thr Leu Lys Glu Leu Tyr Lys Ala Ser Gly Gly Pro Tyr
                340                 345                 350

Gly Ala Val Gly Val Asp Leu Ala Phe Glu Thr Met Leu Cys Gln Ile
                355                 360                 365

Phe Gly Thr Asp Phe Ile Asp Ser Phe Lys Ala Lys Arg Pro Ala Ala
370                 375                 380

Trp Val Asp Leu Thr Ile Ala Phe Glu Ala Arg Lys Thr Ala Ala
385                 390                 395                 400

Pro Gly Arg Ala Asn Thr Leu Asn Ile Ser Leu Pro Phe Ser Phe Ile
                405                 410                 415

Asp Phe Tyr Lys Gln His Arg Gly Gln Ser Val Glu Thr Ala Leu Arg
                420                 425                 430

Lys Ser Asn Met Asn Phe Ile Lys Trp Ser Ser Gln Gly Met Leu Arg
                435                 440                 445

Leu Ser Thr Glu Ala Thr Asn Glu Leu Phe Gln Pro Thr Ile Asn Asn
                450                 455                 460
```

```
Ile Ile Lys His Ile Glu Asn Val Met Gln Lys Glu Val Lys Gly
465                 470                 475                 480

Val Arg Phe Leu Phe Leu Val Gly Gly Phe Ala Glu Ser Pro Met Leu
                485                 490                 495

Gln Arg Ala Ile Gln Asn Thr Leu Gly Arg Asn Cys Arg Ile Ile Ile
            500                 505                 510

Pro His Asp Val Gly Leu Thr Ile Leu Lys Gly Ala Val Leu Phe Gly
            515                 520                 525

Leu Asp Pro Thr Val Val Arg Val Arg Cys Pro Leu Thr Tyr Gly
530                 535                 540

Val Gly Val Leu Asn Arg Phe Val Glu Gly Arg His Pro His Asp Lys
545                 550                 555                 560

Leu Leu Ile Lys Asp Gly Arg Glu Trp Cys Thr Asp Ile Leu Asp Arg
                565                 570                 575

Phe Val Ser Val Asp Gln Ser Val Ala Leu Gly Glu Val Val Arg Arg
            580                 585                 590

Ser Tyr Thr Pro Ala Arg Met Gly Gln Arg Lys Ile Ile Asn Ile
            595                 600                 605

Tyr Cys Ser Asp Thr Asp Asp Ile Thr Tyr Ile Thr Asp Pro Gly Val
610                 615                 620

Arg Lys Cys Gly Ala Ile Thr Leu Asp Leu Leu Glu Ser Gly Glu Ala
625                 630                 635                 640

Ser Ala Ser Thr Gly Asp Asn Asp Lys Gly Ser Ala Phe Glu Arg Arg
                645                 650                 655

Glu Ile Arg Thr Thr Met Gln Phe Gly Asp Thr Glu Ile Lys Val Thr
            660                 665                 670

Ala Val Asp Val Ala Thr Gly Arg Leu Val Arg Ala Ser Ile Asp Phe
675                 680                 685

Leu Ser Asn
    690

<210> SEQ ID NO 4
<211> LENGTH: 685
<212> TYPE: PRT
<213> ORGANISM: Mus musculus

<400> SEQUENCE: 4

Met Leu Thr Val Pro Glu Met Gly Leu Gln Gly Leu Tyr Ile Ser Ser
1               5                   10                  15

Ser Pro Glu Arg Ser Pro Val Pro Ser Pro Pro Gly Ser Pro Arg Thr
            20                  25                  30

Gln Glu Ser Cys Gly Ile Ala Pro Leu Thr Pro Ser Gln Ser Pro Lys
        35                  40                  45

Pro Glu Ala Arg Ala Leu Gln Gln Ala Ser Phe Ser Val Val Ala
    50                  55                  60

Ile Asp Phe Gly Thr Thr Ser Ser Gly Tyr Ala Phe Ser Phe Ala Ser
65                  70                  75                  80

Asp Pro Glu Ala Ile His Met Met Arg Lys Trp Glu Gly Gly Asp Pro
                85                  90                  95

Gly Val Ala His Gln Lys Thr Pro Thr Cys Leu Leu Leu Thr Pro Glu
            100                 105                 110

Gly Ile Phe His Ser Phe Gly Tyr Thr Ala Arg Asp Tyr His Asp
        115                 120                 125

Leu Asp Pro Glu Glu Ala Arg Asp Trp Leu Tyr Phe Glu Lys Phe Lys
130                 135                 140
```

```
Met Lys Ile His Ser Ala Thr Asp Leu Thr Leu Lys Thr Gln Leu Glu
145                 150                 155                 160

Ala Val Asn Gly Lys Lys Met Leu Ala Leu Glu Val Phe Ala His Ala
            165                 170                 175

Leu Arg Phe Phe Lys Glu His Ala Leu Gln Glu Leu Arg Glu Gln Ser
            180                 185                 190

Glu Cys Met Leu Glu Lys Gly Ala Val Arg Trp Val Leu Thr Val Pro
        195                 200                 205

Ala Ile Trp Lys Gln Pro Ala Lys Gln Phe Met Arg Glu Ala Ala Tyr
        210                 215                 220

Leu Ala Gly Leu Val Ser Arg Glu Asp Ala Glu Lys Leu Leu Ile Ala
225                 230                 235                 240

Leu Glu Pro Glu Ala Ala Ser Val Tyr Cys Arg Lys Leu Arg Leu His
                245                 250                 255

Gln Leu Met Asp Leu Ser Ser Arg Thr Ala Gly Arg Gly Arg Leu Gly
                260                 265                 270

Glu Arg Arg Ser Ile Asp Ser Ser Phe Arg His Ala Arg Glu Gln Leu
            275                 280                 285

Arg Arg Ser Arg His Ser Arg Thr Phe Leu Val Glu Ala Gly Val Gly
290                 295                 300

Glu Leu Trp Ala Glu Met Gln Glu Gly Asp Arg Tyr Met Val Ala Asp
305                 310                 315                 320

Cys Gly Gly Gly Thr Val Asp Leu Thr Val His Gln Leu Glu Gln Pro
                325                 330                 335

His Gly Thr Leu Lys Glu Leu Tyr Lys Ala Ser Gly Gly Pro Tyr Gly
            340                 345                 350

Ala Val Gly Val Asp Leu Ala Phe Glu Gln Leu Leu Cys Arg Ile Phe
            355                 360                 365

Gly Glu Asp Phe Ile Ala Lys Phe Lys Arg Gln Arg Pro Ala Ala Trp
370                 375                 380

Val Asp Leu Thr Ile Ala Phe Glu Ala Arg Lys Arg Thr Ala Gly Pro
385                 390                 395                 400

His Arg Ala Gly Ala Leu Asn Ile Ser Leu Pro Phe Ser Phe Ile Asp
                405                 410                 415

Phe Tyr Arg Lys Gln Arg Gly His Asn Val Glu Thr Ala Leu Arg Arg
            420                 425                 430

Ser Ser Val Asn Leu Val Lys Trp Ser Ser Gln Gly Met Leu Arg Met
        435                 440                 445

Ser Cys Glu Ala Met Asn Glu Leu Phe Gln Pro Thr Val Ser Gly Ile
        450                 455                 460

Ile Gln His Ile Glu Met Leu Leu Ala Lys Pro Glu Val Gln Gly Val
465                 470                 475                 480

Lys Leu Leu Phe Leu Val Gly Phe Ala Glu Ser Ala Val Leu Gln
                485                 490                 495

His Ala Val Gln Glu Ala Leu Gly Thr Arg Gly Leu Arg Val Val Val
            500                 505                 510

Pro His Asp Val Gly Leu Thr Ile Leu Lys Gly Ala Val Leu Phe Gly
            515                 520                 525

Gln Ala Pro Gly Val Val Arg Val Arg Arg Ser Pro Leu Thr Tyr Gly
        530                 535                 540

Val Gly Val Leu Asn Arg Phe Val Pro Gly His His Pro Pro Glu Lys
545                 550                 555                 560

Leu Leu Val Arg Asp Gly Arg Arg Trp Cys Thr Asp Val Phe Glu Arg
                565                 570                 575
```

```
Phe Val Ala Ala Glu Gln Ser Val Ala Leu Gly Glu Val Arg Arg
            580                 585                 590

Ser Tyr Cys Pro Ala Arg Pro Gly Gln Arg Arg Val Leu Ile Asn Leu
            595                 600                 605

Tyr Cys Cys Ala Ala Glu Asp Ala Arg Phe Ile Thr Asp Pro Gly Val
        610                 615                 620

Arg Lys Cys Gly Ala Leu Ser Leu Glu Leu Glu Pro Glu Gly Cys Pro
625                 630                 635                 640

Glu Asn Thr Gly Thr Ser Pro Ser Arg Glu Ile Arg Ala Ala Met
            645                 650                 655

Gln Phe Gly Asp Thr Glu Ile Lys Val Thr Ala Val Asp Val Ser Thr
            660                 665                 670

Asn Arg Ser Val Arg Ala Ile Asp Phe Leu Ser Asn
            675                 680                 685
```

<210> SEQ ID NO 5
<211> LENGTH: 735
<212> TYPE: PRT
<213> ORGANISM: Rattus norgivicus

<400> SEQUENCE: 5

```
Met Leu Thr Val Pro Glu Met Gly Leu Gln Gly Leu Tyr Ile Ser Ser
1               5                   10                  15

Ser Pro Glu Arg Ser Pro Val Pro Ser Pro Gly Ser Pro Arg Thr
            20                  25                  30

Gln Glu Ser Cys Gly Ile Ala Pro Leu Thr Pro Ser Gln Ser Pro Lys
            35                  40                  45

Pro Glu Val Arg Ala Pro Gln Arg Ala Ser Phe Ser Val Val Ala
        50                  55                  60

Ile Asp Phe Gly Thr Thr Ser Ser Gly Tyr Ala Phe Ser Phe Ala Thr
65                  70                  75                  80

Asp Pro Glu Ala Ile His Met Met Arg Lys Trp Glu Gly Gly Asp Pro
            85                  90                  95

Gly Val Ala His Gln Lys Thr Pro Thr Cys Leu Leu Leu Thr Pro Glu
            100                 105                 110

Gly Ile Phe His Ser Phe Gly Tyr Thr Ala Arg Asp Tyr Tyr His Asp
            115                 120                 125

Leu Asp Pro Glu Glu Ala Arg Asp Trp Leu Tyr Phe Glu Lys Phe Lys
    130                 135                 140

Met Lys Ile His Ser Ala Thr Asp Leu Thr Leu Lys Thr Gln Leu Glu
145                 150                 155                 160

Ala Val Asn Gly Lys Lys Met Leu Ala Leu Glu Val Phe Ala His Ala
            165                 170                 175

Leu Arg Phe Phe Lys Glu His Ala Leu Gln Leu Pro Glu Arg Ala Glu
            180                 185                 190

Asn Ala Ser Asp Gln Leu Ser Pro Tyr Gly Pro Phe Pro Thr Pro Pro
        195                 200                 205

Thr Leu Gln Glu Leu Arg Glu Gln Ser Glu Cys Met Leu Glu Lys Asp
    210                 215                 220

Ala Val Arg Trp Val Leu Thr Val Pro Ala Ile Trp Lys Gln Pro Ala
225                 230                 235                 240

Lys Gln Phe Met Arg Glu Ala Ala Tyr Leu Lys Arg Trp Glu Gln Pro
            245                 250                 255

Asp Pro Arg Ala Pro Ser Tyr Met Thr Val Tyr Gly Ala Gly His Thr
            260                 265                 270
```

-continued

```
Tyr Pro Gln Ala Gly Leu Val Ser Arg Glu Asp Ala Glu Lys Leu Leu
        275                 280                 285

Ile Ala Leu Glu Pro Glu Ala Ala Ser Val Tyr Cys Arg Lys Leu Arg
290                 295                 300

Leu His Gln Leu Met Asp Leu Ser Ser Arg Thr Ala Gly Gly Arg
305                 310                 315                 320

Leu Gly Glu Arg Arg Ser Ile Asp Ser Ser Phe Arg His Ala Arg Glu
                325                 330                 335

Gln Leu Arg Arg Ser Arg His Ser Arg Thr Phe Leu Val Glu Ser Gly
                340                 345                 350

Val Gly Glu Leu Trp Ser Glu Met Gln Glu Gly Asp Arg Tyr Met Val
        355                 360                 365

Ala Asp Cys Gly Gly Gly Thr Val Asp Leu Thr Val His Gln Leu Glu
370                 375                 380

Gln Pro His Gly Thr Leu Lys Glu Leu Tyr Lys Ala Ser Gly Gly Pro
385                 390                 395                 400

Tyr Gly Ala Val Gly Val Asp Leu Ala Phe Glu Gln Leu Leu Cys Arg
                405                 410                 415

Ile Phe Gly Glu Asp Phe Ile Ala Lys Phe Lys Arg Gln Arg Pro Ala
                420                 425                 430

Ala Trp Val Asp Leu Thr Ile Ala Phe Glu Ala Arg Lys Arg Thr Ala
        435                 440                 445

Gly Pro His Arg Ala Gly Ala Leu Asn Ile Ser Leu Pro Phe Ser Phe
        450                 455                 460

Ile Asp Phe Tyr Arg Lys Gln Arg Gly His Asn Val Glu Thr Ala Leu
465                 470                 475                 480

Arg Arg Ser Ser Val Asn Phe Val Lys Trp Ser Ser Gln Gly Met Leu
                485                 490                 495

Arg Met Ser Cys Glu Ala Met Asn Glu Leu Phe Gln Pro Thr Val Ser
                500                 505                 510

Gly Ile Ile Gln His Ile Glu Met Leu Leu Ala Lys Pro Glu Val Gln
        515                 520                 525

Gly Val Lys Leu Leu Phe Leu Val Gly Gly Phe Ala Glu Ser Ala Val
        530                 535                 540

Leu Gln His Ala Val Gln Glu Ala Leu Gly Asn Arg Gly Leu Arg Val
545                 550                 555                 560

Val Val Pro His Asp Val Gly Leu Thr Ile Leu Lys Gly Ala Val Leu
                565                 570                 575

Phe Gly Gln Ala Pro Gly Val Val Arg Val Arg Arg Ser Pro Leu Thr
                580                 585                 590

Tyr Gly Val Gly Val Leu Asn Arg Phe Val Pro Gly His His Pro Pro
        595                 600                 605

Glu Lys Leu Leu Val Arg Asp Gly Arg Arg Trp Cys Thr Asp Val Phe
610                 615                 620

Glu Arg Phe Val Ala Ala Glu Gln Ser Val Ala Leu Gly Glu Glu Val
625                 630                 635                 640

Arg Arg Ser Tyr Cys Pro Ala Arg Pro Gly Gln Arg Val Leu Ile
                645                 650                 655

Asn Leu Tyr Cys Cys Ala Ala Glu Asp Ala Arg Phe Ile Thr Asp Pro
                660                 665                 670

Gly Val Arg Lys Cys Gly Ala Leu Ser Leu Glu Leu Glu Pro Glu Gly
        675                 680                 685

Ser Pro Glu Asn Thr Gly Thr Ser Pro Ser Arg Arg Glu Ile Arg Ala
```

```
            690             695             700
Ala Met Gln Phe Gly Asp Thr Glu Ile Lys Val Thr Ala Val Asp Val
705                 710                 715                 720

Ser Thr Asn Arg Ser Val Arg Ala Ala Ile Asp Phe Leu Ser Asn
                725                 730                 735

<210> SEQ ID NO 6
<211> LENGTH: 25
<212> TYPE: DNA
<213> ORGANISM: Artificial Sequence
<220> FEATURE:
<223> OTHER INFORMATION: synthetic

<400> SEQUENCE: 6
atattacagg actttcacag cccga                                         25

<210> SEQ ID NO 7
<211> LENGTH: 25
<212> TYPE: DNA
<213> ORGANISM: Artificial Sequence
<220> FEATURE:
<223> OTHER INFORMATION: synthetic

<400> SEQUENCE: 7
attttagagg agtttcacac ccgga                                         25

<210> SEQ ID NO 8
<211> LENGTH: 25
<212> TYPE: DNA
<213> ORGANISM: Artificial Sequence
<220> FEATURE:
<223> OTHER INFORMATION: synthetic

<400> SEQUENCE: 8
acagacataa atacctcatc atgtg                                         25

<210> SEQ ID NO 9
<211> LENGTH: 20
<212> TYPE: DNA
<213> ORGANISM: Artificial Sequence
<220> FEATURE:
<223> OTHER INFORMATION: synthetic

<400> SEQUENCE: 9
gctgtgaaag tcctgtaata                                               20

<210> SEQ ID NO 10
<211> LENGTH: 20
<212> TYPE: DNA
<213> ORGANISM: Artificial Sequence
<220> FEATURE:
<223> OTHER INFORMATION: synthetic

<400> SEQUENCE: 10
aaagtatagc caatgtctgg                                               20

<210> SEQ ID NO 11
<211> LENGTH: 33
<212> TYPE: DNA
<213> ORGANISM: Artificial Sequence
<220> FEATURE:
<223> OTHER INFORMATION: synthetic

<400> SEQUENCE: 11
acaggatcca ccatgttggc tgtcccggag atg                                33
```

```
<210> SEQ ID NO 12
<211> LENGTH: 24
<212> TYPE: DNA
<213> ORGANISM: Artificial Sequence
<220> FEATURE:
<223> OTHER INFORMATION: synthetic

<400> SEQUENCE: 12
tcagttggaa agaaagtcga tgga                                          24

<210> SEQ ID NO 13
<211> LENGTH: 19
<212> TYPE: DNA
<213> ORGANISM: Artificial Sequence
<220> FEATURE:
<223> OTHER INFORMATION: synthetic

<400> SEQUENCE: 13
cttcttcagg gagcacgcc                                                19

<210> SEQ ID NO 14
<211> LENGTH: 19
<212> TYPE: DNA
<213> ORGANISM: Artificial Sequence
<220> FEATURE:
<223> OTHER INFORMATION: synthetic

<400> SEQUENCE: 14
tgtccttctc tggcagcga                                                19

<210> SEQ ID NO 15
<211> LENGTH: 24
<212> TYPE: DNA
<213> ORGANISM: Artificial Sequence
<220> FEATURE:
<223> OTHER INFORMATION: synthetic

<400> SEQUENCE: 15
tcaggagctg agggagcaga gccc                                          24

<210> SEQ ID NO 16
<211> LENGTH: 20
<212> TYPE: DNA
<213> ORGANISM: Artificial Sequence
<220> FEATURE:
<223> OTHER INFORMATION: synthetic

<400> SEQUENCE: 16
caggaataac gcctctgtcc                                               20

<210> SEQ ID NO 17
<211> LENGTH: 20
<212> TYPE: DNA
<213> ORGANISM: Artificial Sequence
<220> FEATURE:
<223> OTHER INFORMATION: synthetic

<400> SEQUENCE: 17
caccacgaga aatgactgct                                               20

<210> SEQ ID NO 18
<211> LENGTH: 26
<212> TYPE: DNA
<213> ORGANISM: Artificial Sequence
<220> FEATURE:
<223> OTHER INFORMATION: synthetic
```

```
<400> SEQUENCE: 18
ccctcccata ttgtgaacga cactga                                     26

<210> SEQ ID NO 19
<211> LENGTH: 19
<212> TYPE: PRT
<213> ORGANISM: Mus musculus

<400> SEQUENCE: 19

Cys Val Asp Val Ser Thr Asn Arg Ser Val Arg Ala Ala Ile Asp Phe
1               5                   10                  15

Leu Ser Asn

<210> SEQ ID NO 20
<211> LENGTH: 33
<212> TYPE: DNA
<213> ORGANISM: Artificial Sequence
<220> FEATURE:
<223> OTHER INFORMATION: synthetic

<400> SEQUENCE: 20
acaggatcca ccatgttggc tgtcccggag atg                             33

<210> SEQ ID NO 21
<211> LENGTH: 57
<212> TYPE: DNA
<213> ORGANISM: Artificial Sequence
<220> FEATURE:
<223> OTHER INFORMATION: synthetic

<400> SEQUENCE: 21
aaactcgagt cacttatcgt cgtcatcctt gtaatcgttg aaagaaagt cgatgga    57

<210> SEQ ID NO 22
<211> LENGTH: 21
<212> TYPE: RNA
<213> ORGANISM: Artificial Sequence
<220> FEATURE:
<223> OTHER INFORMATION: synthetic

<400> SEQUENCE: 22
ccacggaucu caccuugaau u                                          21

<210> SEQ ID NO 23
<211> LENGTH: 21
<212> TYPE: RNA
<213> ORGANISM: Artificial Sequence
<220> FEATURE:
<223> OTHER INFORMATION: synthetic

<400> SEQUENCE: 23
cgacuuucuu uccaacugau u                                          21

<210> SEQ ID NO 24
<211> LENGTH: 21
<212> TYPE: RNA
<213> ORGANISM: Artificial Sequence
<220> FEATURE:
<223> OTHER INFORMATION: synthetic

<400> SEQUENCE: 24
gggacuggcu cuacuucgau u                                          21

<210> SEQ ID NO 25
<211> LENGTH: 21
```

```
<212> TYPE: RNA
<213> ORGANISM: Artificial Sequence
<220> FEATURE:
<223> OTHER INFORMATION: synthetic

<400> SEQUENCE: 25
ccagcuagag gcaguaaauu u                                              21
```

METHODS AND COMPOSITIONS FOR THE TREATMENT AND DIAGNOSIS OF ENDOTHELIAL CELL DISORDERS AND ANGIOGENIC DISORDERS

CROSS REFERENCE TO RELATED APPLICATIONS

This application is the U.S. National Stage of International Application No. PCT/US2006/032497, filed Aug. 18, 2006, which claims benefit of U.S. Provisional Application No. 60/711,579, filed Aug. 26, 2005, each of which is hereby incorporated by reference.

BACKGROUND OF THE INVENTION

In general, the invention relates to methods and compositions for the treatment and diagnosis of endothelial disorders and angiogenic disorders.

Angiogenesis is the formation of new blood vessels from pre-existing vessels. This multi-step process involves signaling to endothelial cells, which results in (1) dissolution of the membrane of the originating vessel, (2) migration and proliferation of the endothelial cells, and (3) formation of a new vascular tube by the migrating cells. While this process is employed by the body in beneficial physiological events such as wound healing, the cyclic build-up of the endometrial lining after menses, and myocardial infarction repair, it is also involved in pathological conditions such as cancer and cancer metastasis; atherosclerosis; inflammatory conditions, such as chronic inflammation and rheumatoid arthritis; pathologic dermatological processes, such as dermatitis, psoriasis, hemangiomas, and Kaposi's sarcoma; as well as eye diseases such as ocular neovascular diseases, diabetic retinopathy, and macular degeneration.

In addition to their role in angiogenesis, endothelial cells are also involved in maintaining vascular health. Endothelial cells form flat, pavement-like patterns on the inside of the vessels and at the junctions between cells there are overlapping regions of endothelial cells, which help to seal the vessel. Endothelial cells are selective filters which regulate the passage of gases, fluid and various molecules across their cell membranes. Different organs have different types of endothelium: some leaky and some very tightly bound.

Endothelial cell health is critical to the maintenance of vascular health and vascular diseases are often caused by injury to the endothelial cells. Once the endothelium is injured, large molecules (e.g., macrophages, lipid, and cholesterol) are allowed to escape through the endothelium and form deposits in the smooth muscle cells in the arterial wall. Macrophages also pass through and accumulate fat (lipid and cholesterol) deposits. The most common form of endothelial cell disease is arteriosclerosis, where the deposition of cholesterol in the sub-endothelial layer of arteries contributes to the pathogenesis of the disease. This process is very slow, but there is a gradual accumulation of this fatty and fibrous material which not only makes the normally elastic artery sclerotic but the deposits, known as "plaques" may lead to a narrowing of the artery and facilitate the formation of a blood clot or a thrombosis. Myocardial infarction and stroke are additional consequences that result from endothelial cell injury or a disruption to the endothelial layers of the arteries.

Endothelial cells are also involved in regulation of inflammatory pathways via regulation of cytokines and the cytokine pathways. For example, during rheumatoid arthritis, endothelial cells become activated and express adhesion molecules and chemokines, leading to leukocyte migration from the blood into the tissue. Endothelial cell permeability increases, leading to edema formation and swelling of the joints.

Maintenance of endothelial cell health and the angiogenic balance is critical to the prevention of diseases and disorders that are caused by or related to endothelial disorders or inappropriate angiogenesis. Therefore, methods that maintain and promote endothelial cell health and that maintain the angiogenic balance within an organism are needed for the treatment and prevention of a variety of pathogenic processes associated with inappropriate angiogenesis and endothelial cell injury or dysfunction.

SUMMARY OF THE INVENTION

We have discovered that HspA12B, the mammalian orthologue of the zebrafish GA2692 protein and distant member of the heat shock 70 (HSP70) family, is a highly endothelial cell specific protein that is critical for angiogenesis and endothelial cell function during development. We have also discovered that reducing the levels of HspA12B in human cells blocked wound healing, migration, and tube formation while overexpression of HspA12B enhanced migration and hastened wound healing. Accordingly, the present invention features HspA12B agonist compounds and the use of HspA12B agonist compounds for promoting endothelial cell health and for treating and preventing endothelial cell disorders in a subject. The present invention also features HspA12B antagonist compounds and the use of HspA12B antagonist compounds for the treating or preventing angiogenic disorders in a subject. The invention also features diagnostic methods that include the use of HspA12B nucleic acid molecules, polypeptides, and antibodies for the diagnosis of angiogenic disorders or endothelial cell disorders.

Accordingly, in a first aspect, the invention features a method of treating or preventing an angiogenic disorder in a subject (e.g., a mammal), that includes administering to the subject a therapeutically effective amount of an HspA12B antagonist compound in an amount and for a time sufficient to treat or prevent the angiogenic disorder in the subject. Preferred HspA12B antagonist compounds can reduce or inhibit (e.g., by at least 10%, 20%, 30%, 40%, 50%, 60%, 70%, 80%, 90% or more) the expression levels or biological activity of an HspA12B protein or nucleic acid. HspA12B polypeptide biological activity includes ATPase activity, heat shock protein or chaperone activity, substrate binding, HspA12B-mediated phosphorylation of Akt, HspA12B-mediated activation of nitric oxide, and promoting endothelial cell health.

In preferred embodiments the HspA12B antagonist compounds specifically binds HspA12B, for example at the ATP binding domain or the substrate-binding domain of HspA12B. In one example, the compound is an antibody or antigen-binding fragment thereof that specifically binds HspA12B. The antibody or antigen-binding fragment can be a monoclonal antibody, a polyclonal antibody, a single-chain antibody, a chimeric antibody, a humanized antibody, a fully humanized antibody, a human antibody, a bispecific antibody, or any other antibody, fragment, or derivative thereof that specifically binds to HspA12B.

In another preferred embodiment, the HspA12B antagonist compound is an antisense nucleobase oligomer complementary to at least a portion of an HspA12B nucleic acid molecule (e.g., the human HspA12B sequence as set forth in SEQ ID NO: 2). Desirably, the antisense nucleobase oligomer is 8 to 30 nucleotides in length and is complementary to at least 8, preferably 10, 12, 14, 16, 18, 20, 22, 24, 26, 28, or 30 nucleotides of HspA12B.

In yet another preferred embodiment, the HspA12B antagonist compound is a morpholino oligomer that is complementary to at least a portion of an HspA12B nucleic acid molecule (e.g., the human HspA12B sequence as set forth in SEQ ID NO: 2).

In yet another preferred embodiment, the HspA12B antagonist compound is a small RNA having at least one strand that is at least 80%, preferably 85%, 90%, 95%, 99%, or 100% complementary to at least a portion of an HspA12B nucleic acid sequence (e.g., the human HspA12B sequence as set forth in SEQ ID NO: 2), or a complementary sequence thereof. The small RNA can be either single-stranded or double-stranded and is at least 15 nucleotides, preferably, 17, 18, 19, 20, 21, 22, 23, 24, 25, 26, 27, 28, 29, 30, 31, 32, 33, 34, or 35, nucleotides in length and even up to 50 or 100 nucleotides in length (inclusive of all integers in between). Preferably, the small RNA is 19 to 25 nucleotides in length and is capable of mediating RNAi. Small RNA includes siRNA, microRNA, or shRNA molecules.

In preferred embodiments of the first aspect, the angiogenic disorder is characterized by excessive proliferation, migration, or excess survival of endothelial cells.

Non-limiting examples of angiogenic disorders that can be treated or prevented by the methods of the invention include cancer, infectious diseases, autoimmune disorders, vascular malformations, DiGeorge syndrome, HHT, cavernous hemangioma, atherosclerosis, transplant arteriopathy, vascular access stenosis associated with hemodialysis, vasculitis, vasculitidis, obesity, psoriasis, warts, allergic dermatitis, scar keloids, pyogenic granulomas, blistering disease, Kaposi sarcoma, persistent hyperplastic vitreous syndrome, retinopathy of prematurity, choroidal neovascularization, macular degeneration, diabetic retinopathy, ocular neovascularization, primary pulmonary hypertension, states of reduced blood pressure, asthma, nasal polyps, inflammatory bowel and periodontal disease, ascites, peritoneal adhesions, contraception, endometriosis, uterine bleeding, ovarian cysts, ovarian hyperstimulation, arthritis, rheumatoid arthritis, synovitis, osteomyelitis, and osteophyte formation.

In a second aspect, the invention features a method for treating or preventing an endothelial cell disorder in a subject (e.g., a mammal) in need thereof, that includes administering to the subject a therapeutically effective amount of an HspA12B agonist compound in an amount and for a time sufficient to treat or prevent the endothelial cell disorder in the subject. HspA12B agonist compounds useful in this aspect of the invention will increase, by at least 10%, 20%, 30%, 40%, 50%, 60%, 70%, 80%, 90% or more) the expression levels or biological activity of an HspA12B protein or nucleic acid. HspA12B polypeptide biological activity includes ATPase activity, heat shock protein or chaperone activity, substrate binding, HspA12B-mediated phosphorylation of Akt, HspA12B-mediated activation of nitric oxide biological activity or expression levels, and promoting endothelial cell health.

In one embodiment, the HspA12B agonist compound is a purified HspA12B polypeptide or biologically active fragment thereof. Preferably the biologically active fragment of HspA12B includes the ATP binding domain or the substrate binding domain of HspA12B.

In another embodiment, the HspA12B agonist compound is an isolated HspA12B nucleic acid molecule, or fragment thereof, encoding an HspA12B polypeptide, or a biologically active fragment thereof.

In yet another embodiment, the HspA12B agonist compound is a growth factor (e.g., VEGF, Ang-1, Ang-2, bFGF, or PlGF) that increases the biological activity or expression level of HspA12B.

Endothelial disorders that can be treated or prevented by the methods of the invention include any endothelial disorder that is characterized by insufficient angiogenesis, hypertension, vasoconstriction, vascular leak, altered vasomotor tone, hypercoagulation, anti-inflammatory properties, and poor endothelial cell health. Non-limiting examples of endothelial disorders include Alzheimer's disease, amyotrophic lateral sclerosis, diabetic neuropathy, stroke, atherosclerosis, diabetes, restenosis, coronary artery disease, peripheral vascular disease, vascular leak, vasculitis, vasculitidis, Wegner's disease, gastric or oral ulcerations, cirrhosis, hepatorenal syndrome, Crohn's disease, hair loss, skin purpura, telangiectasia, venous lake formation, delayed wound healing, preeclampsia, sepsis, ischemia-reperfusion injury, hypertension, chronic or acute infection, menorrhagia, neonatal respiratory distress, pulmonary fibrosis, emphysema, nephropathy, glomerulonephritis, sclerodoma, and vascular abnormalities.

In a third aspect, the invention features a method for promoting endothelial cell heath in a subject (e.g., a mammal) in need thereof, that includes administering to the subject a therapeutically effective amount of an HspA12B agonist compound in an amount and for a time sufficient to promote endothelial cell health in the subject. Endothelial cell health can be measured by any of the following criteria: endothelial cell proliferation, prevention or inhibition of endothelial cell death or senescence, the ability to form a barrier and prevent the movement of molecules and cells through the barrier, the ability to maintain anti-coagulation function, and the ability to maintain vascular tone. An HspA12B agonist compound useful in this aspect of the invention is any HspA12B compound that can increase or that can bring to levels comparable to those found for a normal endothelial cell any of the criteria for endothelial cell health. Preferably, the HspA12B agonist compound promotes neovascularization in the subject.

In one embodiment, the HspA12B agonist compound is a purified HspA12B polypeptide or biologically active fragment thereof. Preferably the biologically active fragment of HspA12B includes the ATP binding domain or the substrate binding domain of HspA12B.

In another embodiment, the HspA12B agonist compound is an isolated HspA12B nucleic acid molecule encoding an HspA12B polypeptide, or a biologically active fragment thereof.

In yet another embodiment, the HspA12B agonist compound is a growth factor (e.g., VEGF, Ang-1, Ang-2, bFGF, or PlGF) that increases the biological activity or expression level of HspA12B.

In a fourth aspect, the invention features a method of diagnosing a subject as having or having a propensity to develop an angiogenic or endothelial cell disorder, that includes determining the level of an HspA12B polypeptide, HspA12B nucleic acid, or fragments thereof, in a sample from the subject relative to a reference sample or level, wherein an alteration in the subject levels relative to the reference sample or level is diagnostic of an angiogenic or endothelial cell disorder or a propensity to develop an angiogenic or endothelial cell disorder in the subject. An increase in the level of an HspA12B polypeptide, HspA12B nucleic acid, or fragments thereof, is an indicator of an angiogenic disorder in the subject. A decrease in the level of an HspA12B polypeptide, HspA12B nucleic acid, or fragments thereof, is an indicator of an endothelial cell disorder in the subject.

In one embodiment, the level of an HspA12B polypeptide is measured using an immunological assay, enzymatic assay, or colorimetric assay.

In a fifth aspect, the invention features a method of diagnosing a subject as having or having a propensity to develop an angiogenic disorder or an endothelial cell disorder, that includes determining the level of an antibody, or a fragment thereof, that specifically binds HspA12B in a blood or serum sample from the subject relative to a reference level, wherein an alteration in the subject levels compared to the reference level is diagnostic of an angiogenic disorder or an endothelial cell disorder or a propensity to develop an angiogenic disorder or an endothelial cell disorder in the subject. An increase in the level of an antibody that specifically binds HspA12B, or antigen-binding fragments thereof, is an indicator of an angiogenic disorder in the subject. A decrease in the level of an antibody that specifically binds HspA12B, or antigen-binding fragments thereof, is an indicator of an endothelial cell disorder in the subject.

In one embodiment, the level of the antibody, or fragment thereof, that specifically binds HspA12B includes the use of an immunological assay and an HspA12B polypeptide, or fragment thereof, as a substrate.

In a sixth aspect, the invention features a method of monitoring the endothelial cell health of a subject, that includes measuring the level of an HspA12B polypeptide, nucleic acid, HspA12B specific antibody, or fragments thereof in a sample from the subject, and comparing the level to a reference sample or level, wherein an alteration in the level is an indicator of a change in the endothelial cell health of the subject.

In one embodiment, the method is used to monitor a subject during treatment for an angiogenic or endothelial cell disorder. In another embodiment, the method is used to monitor a subject at risk for an angiogenic or endothelial cell disorder (e.g., atherosclerosis).

In preferred embodiments of any of the diagnostic or monitoring aspects of the invention, the sample is a bodily fluid (e.g., serum, blood, plasma, or urine) a tissue, or a cell from the subject.

In a seventh aspect, the invention features a kit for the diagnosis of an angiogenic disorder or an endothelial cell disorder, that includes an HspA12B binding protein and instructions for the use of the HspA12B binding protein for the diagnosis of an angiogenic disorder or an endothelial cell disorder in a subject. In one embodiment, the HspA12B binding protein is an antibody, or an antigen binding fragment thereof. In another embodiment, the kit also includes components for measuring the level of the HspA12B protein, such as components for an ELISA or immunoassay.

In an eighth aspect, the invention features a kit for the diagnosis of an angiogenic disorder or an endothelial cell disorder, that includes a nucleic acid complementary to at least a portion of HspA12B, wherein the nucleic acid molecules hybridizes at high stringency to HspA12B, and instructions for the use of the nucleic acid for the diagnosis of an angiogenic disorder or an endothelial cell disorder in a subject.

In a ninth aspect, the invention features a kit for the diagnosis of an angiogenic disorder or an endothelial cell disorder, that includes a polypeptide that specifically binds an HspA12B antibody or fragment thereof, and instructions for the use of said nucleic acid for the diagnosis of an angiogenic disorder or an endothelial cell disorder in a subject.

In one embodiment of the above aspects, the kit is used to monitor an angiogenic disorder or an endothelial cell disorder in a subject. In another embodiment, the kit is used to monitor the treatment of a subject for an angiogenic disorder or an endothelial cell disorder.

In a tenth aspect, the invention features a method of identifying a compound for the treatment of an angiogenic disorder or an endothelial cell disorder, that includes contacting a cell that expresses an HspA12B polypeptide with a candidate compound, and comparing the level of expression of the polypeptide in the cell contacted by the compound with the level of expression in a control cell not contacted by the candidate compound, wherein an alteration in expression of the HspA12B polypeptide identifies the candidate compound as a compound for the treatment of an angiogenic disorder or an endothelial cell disorder.

An increase in the expression of the HspA12B polypeptide identifies the compound as a compound useful for the treatment of an endothelial cell disorder. A decrease in the expression of the HspA12B polypeptide identifies the compound as a compound useful for the treatment of an angiogenic disorder.

In an eleventh aspect, the invention features a method of identifying a compound for the treatment of an angiogenic disorder or an endothelial cell disorder, that includes contacting a cell that expresses an HspA12B nucleic acid with a candidate compound, and comparing the level of expression of the HspA12B nucleic acid in the cell contacted by the compound with the level of expression in a control cell not contacted by the candidate compound, wherein an alteration in expression of the HspA12B nucleic acid identifies the candidate compound as a compound for the treatment of an angiogenic disorder or an endothelial cell disorder.

An increase in the expression of the HspA12B nucleic acid molecule identifies the compound as a compound useful for the treatment of an endothelial cell disorder. A decrease in the expression of the HspA12B nucleic acid molecule identifies the compound as a compound useful for the treatment of an angiogenic disorder.

In a twelfth aspect, the invention features a method of identifying a compound for the treatment of an angiogenic disorder or an endothelial cell disorder, that includes contacting a cell that expresses an HspA12B polypeptide with a candidate compound, and comparing the biological activity of the HspA12B polypeptide in the cell contacted by the compound with the biological activity in a control cell not contacted by the candidate compound, wherein an alteration in the biological activity of the HspA12B polypeptide identifies the candidate compound as a compound for the treatment of an angiogenic disorder or an endothelial cell disorder. An increase in the biological activity of the HspA12B polypeptide identifies the compound as a compound useful for the treatment of an endothelial cell disorder. A decrease in the biological activity of the HspA12B polypeptide identifies the compound as a compound useful for the treatment of an angiogenic disorder.

Desirably, the HspA12B biological activity includes one or more of the following: ATPase activity, heat shock protein or chaperone activity, substrate binding, HspA12B-mediated phosphorylation of Akt, HspA12B-mediated activation of nitric oxide, and promoting endothelial cell health.

By "angiogenesis" is meant the formation of new blood vessels and/or the increase in the volume, diameter, length, or permeability of existing blood vessels, such as blood vessels in a tumor or between a tumor and surrounding tissue. Angiogenesis is associated with a variety of neoplastic and non-neoplastic disorders.

By "angiogenic disorder" is meant a disease associated with excessive or insufficient blood vessel growth, an abnormal blood vessel network, and/or abnormal blood vessel remodeling. For example, insufficient vascular growth can lead to decreased levels of oxygen and nutrients, which are required for cell survival. Non-limiting examples of angiogenic disorders are cancers which require neovascularization to support tumor growth, infectious diseases, autoimmune disorders, vascular malformations, DiGeorge syndrome, HHT, cavernous hemangioma, atherosclerosis, transplant arteriopathy, vascular access stenosis associated with hemodialysis, vasculitis, vasculitidis, obesity, psoriasis, warts, allergic dermatitis, scar keloids, pyogenic granulomas, blistering disease, Kaposi sarcoma, persistent hyperplastic vitreous syndrome, retinopathy of prematurity, choroidal neovascularization, macular degeneration, diabetic retinopathy, ocular neovascularization, primary pulmonary hypertension, asthma, nasal polyps, inflammatory bowel and periodontal disease, ascites, peritoneal adhesions, contraception, endometriosis, uterine bleeding, ovarian cysts, ovarian hyperstimulation, arthritis, rheumatoid arthritis, chronic articular rheumatism, synovitis, osteoarthritis, osteomyelitis, and osteophyte formation.

By "anti-cancer therapy" is meant any therapy intended to prevent, slow arrest or reverse the growth of a cancer or a cancer metastases. Generally, an anti-cancer therapy will reduce or reverse any of the characteristics that define the cancer cell (see Hanahan et al., *Cell* 100:57-50, 2000). Most cancer therapies target the cancer cell by slowing, arresting, reversing, decreasing the invasive capabilities, or decreasing the ability of the cell to survive the growth of a cancer cell. Additional anti-cancer therapies can target non-cancer cells including immune cells, endothelial cells, fibroblasts, immune and inflammatory cells or the extracellular matrix in the tumor microenvironment. Anti-cancer therapies include, without limitation, surgery, radiation therapy (radiotherapy), biotherapy, immunotherapy, chemotherapy, or a combination of these therapies.

By "antisense nucleobase oligomer" is meant a nucleobase oligomer, regardless of length, that is complementary to at least a portion of the coding strand or mRNA of an HSPA12B gene. By a "nucleobase oligomer" is meant a compound that includes a chain of at least eight nucleobases, preferably at least twelve, and most preferably at least sixteen bases, joined together by linkage groups. Included in this definition are natural and non-natural oligonucleotides, both modified and unmodified, as well as oligonucleotide mimetics such as Protein Nucleic Acids, locked nucleic acids, and arabinonucleic acids. Numerous nucleobases and linkage groups may be employed in the nucleobase oligomers of the invention, including those described in U.S. Patent Publication Nos. 20030114412 (see for example paragraphs 27-45 of the publication) and 20030114407 (see for example paragraphs 35-52 of the publication), incorporated herein by reference. The nucleobase oligomer can also be targeted to the translational start and stop sites. Preferably the antisense nucleobase oligomer comprises from about 8 to 30 nucleotides. The antisense nucleobase oligomer can also contain at least 40, 60, 85, 120, or more consecutive nucleotides that are complementary to HspA12B mRNA or DNA, and may be as long as the full-length mRNA or gene.

By "chemotherapy" is meant the use of a chemical agent to destroy a cancer cell, or to slow, arrest, or reverse the growth of a cancer cell.

By "chemotherapeutic agent" is meant a chemical that may be used to destroy a cancer cell, or to slow, arrest, or reverse the growth of a cancer cell. Chemotherapeutic agents include, without limitation, asparaginase, bleomycin, busulfan carmustine (commonly referred to as BCNU), chlorambucil, cladribine (commonly referred to as 2-CdA), CPT11, cyclophosphamide, cytarabine (commonly referred to as Ara-C), dacarbazine, daunorubicin, dexamethasone, doxorubicin (commonly referred to as Adriamycin), etoposide, fludarabine, 5-fluorouracil (commonly referred to as 5FU), hydroxyurea, idarubicin, ifosfamide, interferon-α (native or recombinant), levamisole, lomustine (commonly referred to as CCNU), mechlorethamine (commonly referred to as nitrogen mustard), melphalan, mercaptopurine, methotrexate, mitomycin, mitoxantrone, paclitaxel, pentostatin, prednisone, procarbazine, tamoxifen, taxol-related compounds, 6-thiogaunine, topotecan, vinblastine, and vincristine.

By "compound" is meant any small molecule chemical compound, antibody, nucleic acid molecule, polypeptide, or fragments thereof.

By "endothelial cell disorder" is meant a condition or disease associated with any one or more of the following: insufficient angiogenesis, hypertension, vascular leak, altered vasomotor tone, vasoconstriction, hypercoagulation, and anti-inflammatory properties. Non-limiting examples of endothelial cell disorders include Alzheimer's disease, amyotrophic lateral sclerosis, diabetic neuropathy, stroke, atherosclerosis, diabetes, restenosis, coronary artery disease, peripheral vascular disease, vascular leak, vasculitis, vasculitidis, Wegner's disease, gastric or oral ulcerations, cirrhosis, hepatorenal syndrome, Crohn's disease, hair loss, skin purpura, telangiectasia, venous lake formation, delayed wound healing, pre-eclampsia, sepsis, ischemia-reperfusion injury, hypertension, chronic or acute infection, menorrhagia, neonatal respiratory distress, pulmonary fibrosis, emphysema, nephropathy, glomerulonephritis, sclerodoma, and vascular abnormalities. Endothelial cell health is measured by any of the following criteria: endothelial cell proliferation and prevention or inhibition of senescence or endothelial cell death; the ability to form a barrier and prevent the movement of molecules and cells through the barrier; the ability to maintains anti-coagulation function; and the ability to maintain vascular tone. An endothelial cell that is considered healthy will have normal levels (i.e., a level equivalent to that found in a normal endothelial cell) of any of the above parameters for endothelial cell function.

By "effective amount" is meant an amount sufficient to prevent or reduce any of the disorders of the invention including angiogenic disorders, endothelial cell disorders or any symptom associated with the disorder. It will be appreciated that there will be many ways known in the art to determine the therapeutic amount for a given application. For example, the pharmacological methods for dosage determination may be used in the therapeutic context.

By "expression" is meant the detection of a gene or polypeptide by standard art known methods. For example, polypeptide expression is often detected by western blotting or ELISA; DNA expression is often detected by Southern blotting or polymerase chain reaction (PCR); and RNA expression is often detected by Northern blotting, PCR, or RNAse protection assays.

By "fragment" is meant a portion of a polypeptide or nucleic acid molecule that contains, preferably, at least 10%, 20%, 30%, 40%, 50%, 60%, 70%, 80%, 90%, 95%, or more of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1100, 1200, 1500, 1800, 2000, 2100, 2200, 2500, 2600, 2700, 2800, 3000, or more nucleotides or 10, 20, 30, 40, 50, 60, 70, 80, 90, 100, 120, 140, 160, 180, 190, 200, 250, 300, 350, 400, 450, 500, 550, 600, 650, or more up to 686 amino acids. Preferred fragments of HspA12B useful as HspA12B agonist compounds will have HspA12B biological activity (e.g., substrate binding, ATPase activity, promoting endothelial cell migration, promoting endothelial cell tube formation, activation of nitric oxide, and inducing phosphorylation Akt) and may include, for example, the substrate binding domain or the ATP binding domain. (Han et al., *Proc. Natl. Acad. Sci.* 100:1256-1261 (2003)). Preferred fragments of HspA12B useful as HspA12B antagonist compounds will reduce or inhibit HspA12B biological activity (see above).

By "heterologous" is meant any two or more nucleic acid or polypeptide sequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous polypeptide will often refer to two or more subsequences that are not found in the same relationship to each other in nature (e.g., a fusion protein).

By "homologous" is meant any gene or polypeptide sequence that bears at least 30% homology, more preferably 40%, 50%, 60%, 70%, 80%, and most preferably 90%, 95%, 96%, 97%, 98%, 99%, or more homology to a known gene or polypeptide sequence over the length of the comparison sequence. A "homologous" polypeptide can also have at least one biological activity of the comparison polypeptide. For polypeptides, the length of comparison sequences will generally be at least 16 amino acids, preferably at least 20 amino acids, more preferably at least 30, 40, 50, 60, 70, 80, 90, 100, 120, 140, 160, 180, 190, 200, 250, 300, 350, 400, 450, 500, 550, 600, 650, 686 amino acids or more. For nucleic acids, the length of comparison sequences will generally be at least 50 nucleotides, preferably at least 60, 70, 80, 90, 100, 150, 200, 250, 300, 350, 400, 450, 500, 550, 600, 700, 800, 900, 1000, 1100, 1200, 1500, 1800, 2000, 2100, 2200, 2500, 2600, 2800, 3000 or more nucleotides or more. "Homology" can also refer to a substantial similarity between an epitope used to generate antibodies and the protein or fragment thereof to which the antibodies are directed. In this case, homology refers to a similarity sufficient to elicit the production of antibodies that can specifically recognize the protein or polypeptide.

By "HspA12B" is meant a polypeptide, or a nucleic acid sequence that encodes it, or fragments or derivatives thereof, that is substantially identical or homologous to or encodes any of the following amino acid sequences: amino acid sequence of human HspA12B (SEQ ID NO: 1), mouse (SEQ ID NO: 4), and rat (SEQ ID NO: 5). Preferred HspA12B polypeptides will have HspA12B biological activity as described below. HspA12B nucleic acid molecules encode an HspA12B polypeptide and preferably have substantial identity to the nucleic acid sequence of SED ID NO: 2 (human). Accession numbers for exemplary HspA12B nucleic acid and polypeptide sequences are GenBank Accession Numbers BC011103 (mouse), BC110881 (human), BC117284 (human), and NM_052970 (human). HspA12B can also include fragments, derivatives, homologs, or analogs of HspA12B that retain at least 25%, 30%, 40%, 50%, 60%, 70%, 80%, 90%, 95%, 96%, 97%, 98%, 99%, or more HspA12B biological activity.

The HspA12B polypeptides may be isolated from a variety of sources, such as from mammalian tissue or cells (e.g., endothelial cells such as HUVEC cells) or from another source, or prepared by recombinant or synthetic methods. The term "HspA12B" also encompasses modifications to the polypeptide, fragments, derivatives, analogs, and variants of the HspA12B polypeptide.

By "HspA12B biological activity" is meant the any of the following activities: heat shock protein or chaperone activity (e.g., binding to short stretches of hydrophobic peptides and preventing the substrate from irreversible aggregation), ATPase activity, substrate binding, (Han et al., *Proc. Natl. Acad. Sci.* 100:1256-1261 (2003)), Akt phosphorylation, activation of nitric oxide, and promoting endothelial cell health. Assays for HspA12B biological activity include assays for chaperone activity, substrate binding, ATPase activity, endothelial cell migration, matrigel tube formation assays (for example, as described in U.S. Patent Application Publication No. 20050025762 and PCT publication No. WO2005/077007), Akt phosphorylation assays, nitric oxide activation assays as known in the art or described herein, microangiograpy or visualization of circulation in an animal model such as the zebrafish model described herein. Such assays are described herein or known in the art (see for example Carrello et al., *Cell Stress Chaperones* 9:167-181 (2004) and McLaughlin et al., *J. Mol. Biol.* 315:787-798 (2002)). "Endothelial cell health" is measured by any of the following criteria: endothelial cell proliferation; prevention or inhibition of senescence or cell death; endothelial cell migration; ability to form a barrier and prevent the movement of molecules and cells through the barrier; the ability to maintain anti-coagulation function, and the ability to maintain vascular tone. An endothelial cell that is considered healthy will have normal levels (i.e., a level equivalent to that found in a normal endothelial cell) of any of the above parameters for endothelial cell function. Assays for endothelial cell health include the following: endothelial cell survival assays, cell proliferation assays (e.g., $^3$H labeling assays, cell counting assays), senescent β-galactosidase assays to measure the percent of the endothelial cells that are senescent, and barrier function assays that include, for example, creating an endothelial cell monolayer using normal cells and cells where an HspA12B antagonist has been added and then measuring the leakiness in the monolayer of HspA12B cells as compared to the normal cells using, for example, labeled dextran, or by showing a decrease in VE-cadherin. Additional assays include anti-coagulation assays for anti-coagulation function and assays for markers of vascular tone, for example, activation of nitric oxide (e.g., phosphorylation of Ser1177 or dephosphorylation of Thr495 by phosphoinositide 3-kinase (PI3K), Akt, VEGF, TGF-β1). (See for example, Parikh et al., *PloS Med.* 3:e46 (2006) e-publication ahead of print).

By "HspA12B agonist compound" is meant any small molecule chemical compound (peptidyl or non-peptidyl), agonistic antibody, nucleic acid molecule, polypeptide, or fragments thereof that increases the levels or biological activity of HspA12B by at least 10%, 20%, 30%, 40%, 50%, 60%, 70%, 80%, 90% or more. Non-limiting examples of HspA12B agonist compounds include HspA12B polypeptides or nucleic acid molecules, or fragments, derivatives, homologs, or analogs thereof; agonistic antibodies; growth factors that increase the biological activity or expression levels of HspA12B (e.g., VEGF, angiopoietin 1, or angiopoietin 2); compounds that increase the half-life of HspA12B mRNA or protein; compounds that increase the transcription or translation of HsPA12B; compounds that decrease the degradation of HspA12B mRNA or protein; compounds that modify the activity of HspA12B, for example to increase HspA12B binding to ATP or HspA12B binding to substrate or to increase HspA12B-mediated phosphorylation of Akt or activation of nitric oxide. HspA12B agonist compounds that increase the biological activity of HspA12B can be identified using the compound in any of the assays described above for HspA12B biological activity and identifying a compound that shows at least a 10%, 20%, 30%, 40%, 50%, 60%, 70%, 80%, 90% or more increase in HspA12B activity as compared to a control where the compound has not been added.

By "HspA12B antagonist compound" is meant any small molecule chemical compound (peptidyl or non-peptidyl), antibody, nucleic acid molecule, polypeptide, or fragments thereof that reduces or inhibits the levels or biological activity of HspA12B by at least 10%, 20%, 30%, 40%, 50%, 60%, 70%, 80%, 90% or more. Non-limiting examples of HspA12B antagonist compounds include fragments of HspA12B (e.g., dominant negative fragments or fragments that are unable to bind ATP or substrate); peptidyl or non-peptidyl compounds that specifically bind HspA12B (e.g., antibodies or antigen-binding fragments thereof), for example at the ATP binding domain or substrate binding domain of HspA12B; antisense nucleobase oligomers; small RNA; small molecule inhibitors; compounds that decrease the half-life of HspA12B mRNA or protein; compounds that decrease transcription or translation of HspA12B; compounds that reduce or inhibit the expression levels (e.g., in bodily fluids such as blood, serum, urine, plasma, etc.) of HspA12B polypeptides or decrease the biological activity of HspA12B polypeptides; compounds that increase the expression or biological activity of a HspA12B inhibitor (e.g., an inhibitor that blocks binding to a substrate or ATP); and compounds that block HspA12B-mediated phosphorylation of Akt or activation of nitric oxide. HspA12B antagonist compounds can be identified using the compound in any of the assays described above for HspA12B biological activity and identifying a compound that shows at least a 10%, 20%, 30%, 40%, 50%, 60%, 70%, 80%, 90% or more decrease in HspA12B activity as compared to a control where the compound has not been added.

By "increase" is meant to augment, preferably by at least 20%, more preferably by at least 50%, and most preferably by at least 70%, 75%, 80%, 85%, 90%, 95% or more. Increase can refer, for example, to the symptoms of the disorder being treated or to the levels or biological activity of HspA12B.

By "metric" is meant a measure. A metric may be used, for example, to compare the levels of a polypeptide or nucleic acid molecule of interest. Exemplary metrics include, but are not limited to, mathematical formulas or algorithms, such as ratios. The metric to be used is that which best discriminates between levels of HspA12B polypeptide in a subject having an angiogenic disorder or an endothelial disorder and a normal reference. Depending on the metric that is used, the diagnostic indicator of an angiogenic disorder or an endothelial disorder may be significantly above or below a reference (e.g., from a control subject not having an angiogenic disorder or an endothelial disorder).

By "pharmaceutically acceptable carrier" is meant a carrier that is physiologically acceptable to the treated mammal while retaining the therapeutic properties of the compound with which it is administered. One exemplary pharmaceutically acceptable carrier substance is physiological saline. Other physiologically acceptable carriers and their formulations are known to one skilled in the art and described, for example, in Remington's Pharmaceutical Sciences, (20$^{th}$ edition), ed. A. Gennaro, 2000, Lippincott, Williams & Wilkins, Philadelphia, Pa.

By "preventing" is meant prophylactic treatment of a subject who is not yet ill, but who is susceptible to, or otherwise at risk of, developing a particular disease. Preferably a subject is determined to be at risk of developing an angiogenic disorder or endothelial disorder using the diagnostic methods known in the art or described herein.

By "promoting endothelial cell health" is meant administering a compound in an amount and for a time sufficient to increase, or bring to the level of a normal endothelial cell, any of the parameters of endothelial cell health described above.

By "protein," "polypeptide," or "polypeptide fragment" is meant any chain of more than two amino acids, regardless of post-translational modification (e.g., glycosylation or phosphorylation), constituting all or part of a naturally occurring polypeptide or peptide, or constituting a non-naturally occurring polypeptide or peptide.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

By "reduce or inhibit" is meant the ability to cause an overall decrease preferably of 20% or greater, more preferably of 50% or greater, and most preferably of 75%, 80%, 85%, 90%, 95%, or greater. Reduce or inhibit can refer to the symptoms of the disorder being treated. For diagnostic or monitoring applications, reduce or inhibit can refer to the level of protein or nucleic acid, detected by the aforementioned assays (see "expression").

By "reference" is meant any sample, standard, or level that is used for comparison purposes. A "normal reference sample" can be a prior sample taken from the same subject; a sample from a subject not having an angiogenic disorder or an endothelial disorder; a subject that is diagnosed with a propensity to develop an angiogenic disorder or an endothelial disorder but does not yet show symptoms of the disorder; a subject that has been treated for an angiogenic disorder or an endothelial disorder; or a sample of a purified reference HSPA12B polypeptide or nucleic acid molecule at a known normal concentration. By "reference standard or level" is meant a value or number derived from a reference sample. A normal reference standard or level can be a value or number derived from a normal subject who does not have an angiogenic disorder or an endothelial disorder that is matched to the sample subject by at least one of the following criteria: age, weight, disease stage, and overall health. A "positive reference" sample, standard or value is a sample or value or number derived from a subject that is known to have an angiogenic disorder or an endothelial disorder, that is matched to the sample subject by at least one of the following criteria: age, weight, disease stage, overall health, prior diagnosis of an angiogenic disorder or an endothelial disorder, and a family history of an angiogenic disorder or an endothelial disorder. A standard curve of levels of purified protein within the normal or positive reference range can also be used as a reference.

By "sample" is meant a bodily fluid (e.g., urine, blood, serum, plasma, or cerebrospinal fluid), tissue, or cell in which the HspA12B polypeptide or nucleic acid molecule is normally detectable.

By "small RNA" is meant any RNA molecule, either single-stranded or double-stranded" that is at least 15 nucleotides, preferably, 17, 18, 19, 20, 21, 22, 23, 24, 25, 26, 27, 28, 29, 30, 31, 32, 33, 34, or 35, nucleotides in length and even up to 50 or 100 nucleotides in length (inclusive of all integers in between). Preferably, the small RNA is capable of mediating RNAi. As used herein the phrase "mediates RNAi" refers to the ability to distinguish which RNAs are to be degraded by the RNAi machinery or process. Included within the term small RNA are "small interfering RNAs" and "microRNA." In general, microRNAs (miRNAs) are small (e.g., 17-26 nucleotides), single-stranded noncoding RNAs that are processed from approximately 70 nucleotide hairpin precursor RNAs by Dicer. Small interfering RNAs (siRNAs) are of a similar size and are also non-coding, however, siRNAs are processed from long dsRNAs and are usually double stranded. siRNAs can also include short hairpin RNAs in which both strands of an siRNA duplex are included within a single RNA molecule. Small RNAs can be used to describe both types of RNA. These terms include double-stranded RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the small RNA or internally (at one or more nucleotides of the RNA). Nucleotides in the RNA molecules of the present invention can also comprise non-standard nucleotides, including non-naturally occurring nucleotides or deoxyribonucleotides. See "nucleobase oligomers" above for additional modifications to the nucleic acid molecule. In a preferred embodiment, the RNA molecules contain a 3' hydroxyl group.

By "specifically binds" is meant a compound or antibody which recognizes and binds a polypeptide of the invention but that does not substantially recognize and bind other molecules in a sample, for example, a biological sample, which naturally includes a polypeptide of the invention. In one example, an antibody that specifically binds HspA12B does not bind other heat shock family members.

By "subject" is meant a mammal, including, but not limited to, a human or non-human mammal, such as a bovine, equine, canine, ovine, or feline.

By "substantially identical" is meant a nucleic acid or amino acid sequence that, when optimally aligned, for example using the methods described below, share at least 65%, 70%, 75%, 80%, 85%, 90%, 95%, 96%, 97%, 98%, 99%, or 100% sequence identity with a second nucleic acid or amino acid sequence, e.g., a HSPA12B sequence. "Substantial identity" may be used to refer to various types and lengths of sequence, such as full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith and Waterman *J. Mol. Biol.* 147:195-7, 1981); "Best-Fit" (Smith and Waterman, Advances in Applied Mathematics, 482-489, 1981) as incorporated into GeneMatcher Plus™, Schwarz and Dayhof "Atlas of Protein Sequence and Structure," Dayhof, M. O., Ed pp 353-358, 1979; BLAST program (Basic Local Aligmnent Search Tool; (Altschul, S. F., W. Gish, et al., *J. Mol. Biol.* 215: 403-410, 1990), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins, the length of comparison sequences will be at least 16 amino acids, preferably at least 20 amino acids, more preferably at least 30, 40, 50, 60, 70, 80, 90, 100, 120, 140, 160, 180, 190, 200, 250, 300, 350, 400, 450, 500, 550, 600, 650, or 686 amino acids or more. For nucleic acids, the length of comparison sequences will generally be at least 50 nucleotides, preferably at least 60, 70, 80, 90, 100, 150, 200, 250, 300, 350, 400, 450, 500, 550, 600, 700, 800, 900, 1000, 1100, 1200, 1500, 1800, 2000, 2100, 2200, 2500, 2600, 2800, 3000 or more nucleotides. It is understood that for the purposes of determining sequence identity when comparing a DNA sequence to an RNA sequence, a thymine nucleotide is equivalent to a uracil nucleotide. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "treating" is meant administering a compound or a pharmaceutical composition for prophylactic and/or therapeutic purposes or administering treatment to a subject already suffering from a disease to improve the subject's condition or to a subject who is at risk of developing a disease. When HspA12B agonist compounds are used to treat a subject with an endothelial cell disorder, it is generally provided in a therapeutically effective amount to achieve any one or more of the following: an increase in endothelial cell migration, an increase in endothelial cell proliferation, a decrease in endothelial cell death, or a decrease in endothelial cell senescence, an increase in endothelial tube formation, a reduction in blood pressure, a decrease in vascular permeability or vascular leak, and an increase in the diameter of a blood vessel or a decrease in the occlusion of a previously clogged blood vessel. When HspA12B antagonist compounds are used to treat a subject with an angiogenic disorder, it is generally provided in a therapeutically effective amount to achieve any one or more of the following: an increase in blood pressure, a reduction or inhibition in the formation of new blood vessels and/or modulating the volume, diameter, length, permeability, or number of existing blood vessels to within the normal reference ranges. In preferred embodiments, an initial or subsequent occurrence of an angiogenic disorder is prevented or an adverse symptom associated with an angiogenic disorder is reduced. Preferably, for the angiogenesis applications, the methods of the present invention result in a reduction or inhibition of 20, 40, 60, 80, or even 100% in the volume, diameter, length, permeability, and/or number of blood vessels as determined using standard methods. Preferably, at least 20, 40, 60, 80, 90, or 95% of the treated subjects have a complete remission in which all evidence of the disease disappears. In another preferred embodiment, the length of time a patient survives after being diagnosed with an angiogenic disorder or an endothelial disorder and treated with a therapy of the invention is at least 20, 40, 60, 80, 100, 200, or even 500% greater than (i) the average amount of time an untreated patient survives or (ii) the average amount of time a patient treated with another therapy survives.

By "vector" is meant a DNA molecule, usually derived from a plasmid or bacteriophage, into which fragments of DNA may be inserted or cloned. A recombinant vector will contain one or more unique restriction sites, and may be capable of autonomous replication in a defined host or vehicle organism such that the cloned sequence is reproducible. A vector contains a promoter operably linked to a gene or coding region such that, upon transfection into a recipient cell, an RNA is expressed.

Other features and advantages of the invention will be apparent from the following Detailed Description, the drawings, and the claims.

BRIEF DESCRIPTION OF THE DRAWINGS

FIGS. 1A-1O are a series of photomicrographs showing HspA12B whole-mount in situ hybridization at different zebrafish developmental stages. FIGS. 1A through 1I are middle somite stages. FIGS. 1A, 1B and 1C are dorsal view of head, trunk and tail, respectively, showing staining in ventral hematopoietic and vasculogenic mesoderm. FIG. 1D is a lateral view. FIG. 1E is a enlarged lateral view of head region showing expression in rhombomeres. FIG. 1F is a lateral view showing expression in first somite. FIG. 1G is a dorsal view of ear showing staining in the anterior part of the otic vesicle. FIGS. 1H, 1I and 1J are embryos at 24 hpf; FIG. 1H is a dorsal view of head region. FIG. 1I is a dorsal view of the whole embryo; FIG. 1J is a JB4 cross section in the truck region of a 24 hpf embryos. Arrowheads point to arterial and venous structures. NT, neural tube; NO, notochord; FIGS. 1K to 1N are 36 hpf embryos; FIG. 1K is an enlarged lateral view of the head; FIG. 1L is a front view showing staining in the heart; FIG. 1M is the dorsal view of the head region; arrow head indicates duct of Cuvier; FIG. 1N is the lateral view of trunk showing staining in both axial vessels and ISVs. FIG. 1O is a lateral view of embryo at 48 hpf.

FIG. 2A shows the in vitro transcription and translation in the absence of MOATG or in the presence of various concentrations of MOATG or MM, demonstrating the efficiency of MOATG in blocking the translation of HspA12B. FIG. 2B shows the results of RT-PCR of zebrafish HspA12B from zebrafish embryos injected with various amounts of MOs3rd. FIGS. 2C, 2D, and 2E are a series of photomicrographs showing 48 hpf embryos injected with 1.0 mM and 2.0 mM MOATG or 1.0 mM MM. FIG. 2F is a graph showing the percentage of normal circulation in morphants injected with 1.0 mM MOATG or MM at 26 hpf. Data were presented as Mean±s.e.m. from three or more independent experiments, difference between MM and MOATG was significant ($p<0.01$) as accessed by two tailed student's t-Test.

FIGS. 3A and 3B are photomicrographs showing an angiogram of fish injected with 1 mM MM (FIG. 3A) or MOATG (FIG. 3B) at 48 hpf. FIG. 3C-3H are photomicrographs showing AP staining and statistical analysis of morphants treated with various concentrations of MM or MOATG. FIGS. 3C, D, E show SIVs. FIGS. 3F, G, H show pectoral fin vessels. FIGS. 3I-J show statistical analysis. FIGS. 3A, C, and E show embryos injected with 1.0 mM MM. In FIGS. 3D and G, morphants were treated with 0.5 mM MOATG. In FIGS. 3B, E, and H, morphants were treated with 1.0 mM MOATG.

FIGS. 4A, 4C, 4E, 4G, and 4I show morphants injected with 1 mM MM. FIGS. 4B, 4D, 4F, 4H, and 4J show morphants injected with 1 mM MOATG. FIGS. 4A, 4B, 4G, 4H show morphants at 27 hpf. FIGS. 4C and 4D show morphants at 36 hpf. FIGS. 4E and 4F show morphants at 54 hpf. FIGS. 4I and 4J show morphants at 24 hpf. In FIGS. 4G, 4H, and 4I the rostral is to the left.

FIG. 5A is an autoradiogram showing detection of HspA12B mRNA in human cell lines by northern blot. Signal is evident only in the HUVEC lane (upper panel), 28S and 18S staining is shown as equal loading control (lower panel). FIG. 5B is a graph showing the comparison of HspA12A and HspA12B mRNA levels in cell lines using real-time PCR. Data from two independent experiments were normalized with the expression levels in HUVECs and presented as mean±s.e.m.; the difference of expression levels between HUVECs and other cell lines were all significant ($p<0.05$) as tested by two tailed student's t-Test.

FIG. 6A shows HEK 293 cells cultured in 6-well plate transfected with 0.1 μg pCS2+-HspA12B-Flag and various siRNAs at 62.5 nM final concentration. Cell lysates were collected after 48 hours and the expression level of HspA12B-Flag was checked by western blot using anti-FLAG antibody. P represents a pool of si1, si2, si3 and si4. FIG. 6B shows the GAPDH loading control for FIG. 6A. FIG. 6C shows HUVECs transfected with si1 and si3 at 62.5 nM final concentration in 6-well plate and endogenous HspA12B expression and examined after 48 hours by western blot using Ab4112 antibody; Lane 4 was loaded with lysate from HUVECs infected with HspA12B-C-FLAG adenovirus. FIG. 6D shows the GAPDH loading control for FIG. 6C.

In FIG. 7A, HUVECs were infected with empty control or HspA12B adenoviruses and migration assay was done with 0.5% serum DMEM or 0.5% serum DMEM plus VEGF (10 ng/ml) in the lower chamber. In FIG. 7B, HUVECs were transfected with NC, si1 and si3. Data from three experiments were shown as mean±s.d. All comparison were tested for statistic significance using two tailed student's t-Test. *, $p<0.05$.

In FIGS. 8A-8B, HUVECs infected with empty control and sense adenoviruses were grown to confluence. Wounds were made using 200 μl pipette tips in the cell lawn 48 hours after infection and media was changed to EBM-2 with 1% serum after the injury. Pictures were taken at 0 and 48 hours. In FIGS. 8C-8D, HUVECs infected with the same adenoviruses were grown to confluence. After making the wound, EBM-2 with 1% serum plus VEGF (10 ng/ml) was added. Pictures were taken at 0 and 30 hours post injury. In FIGS. 8E-8F, HUVECs transfected with NC, si1 and si3 were grown to confluence and wounds were made in the cell monolayer 48 hours after transfection. EBM-2 with 1% serum plus VEGF (10 ng/ml) was added. Pictures were taken at 0 and 24 hours post injury. Representative pictures were shown from at least three independent experiments.

In FIG. 10A, HUVECs in 6-well plate were transfected with NC, si1 and si3 on day 0, split on day 1, serum starved with 0.5% serum EBM-2 on day 2 and stimulated with VEGF (5 ng/ml) in 0.5% serum EBM-2 or EGM-2 MV for 30 minutes on day 3. In FIG. 10B. HUVECs in 10 cm plates were transfected with NC, si1 and si3 on day 0, split onto 2 plates in the early morning of day 1 and infected with myr-Akt adenovirus in the late afternoon and EGM-2 MV was changed 6 hours thereafter; EBM-2 with 2.5% serum was changed in the evening of day 2 and migration assay was done on day 3 with the stimulation of VEGF (10 ng/ml) in 0.5% serum DMEM.

Data from three experiments are shown as mean±s.d. All indicated p values for the comparisons were obtained using two tailed student's t-Test.

Figure 11:
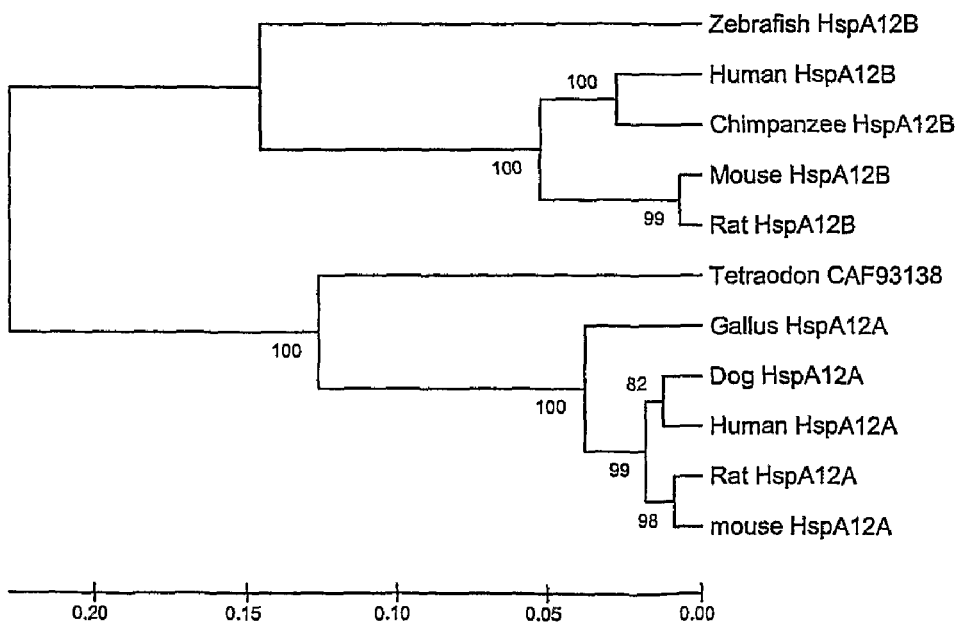

FIGS. 11A-D shows the cloning of zebrafish GA2692/HspA12B. FIG. 11A shows the amino acid (SEQ ID NO: 1) and cDNA (SEQ ID NO: 2) sequence of human HspA12B. FIG. 11B shows a comparison of deduced amino acid sequences of zebrafish (SEQ ID NO: 3) GA2692/HspA12B with human (SEQ ID NO: 1), mouse (SEQ ID NO: 4) and rat (SEQ ID NO: 5) HspA12B. FIG. 11C shows an identity matrix for HspA12Bs from zebrafish, human, mouse, rat and chimpanzee and HspA12A (human). FIG. 11D shows a phylogenetic dendrogram showing the relationship of zebrafish HspA12B in different species.

DETAILED DESCRIPTION OF THE INVENTION

We have discovered that HSPA12B, the mammalian orthologue of the zebrafish GA2692 protein and distant member of the heat shock 70 (HSP70) family, is a highly endothelial cell specific protein that is critical for angiogenesis and endothelial cell function during development. We have shown that a reduction of GA2692 in zebrafish embryos resulted in multiple defects in vasculature, particularly, at sites undergoing active capillary sprouting: the intersegmental vessels, sub-intestinal vessels and the capillary sprouts of the pectoral fin vessel. We have also shown by a combination of northern blot and real-time PCR analysis, that HspA12B is highly expressed in human endothelial cells in vitro. Knockdown of HspA12B by small interfering RNAs in human umbilical vein endothelial cells blocked wound healing, migration and tube formation while overexpression of HspA12B enhanced migration and hastened wound healing. Furthermore, phosphorylation of Akt, known to effect endothelial cell migration was consistently reduced by siRNAs against HspA12B while overexpression of a constitutively active form of Akt rescued the inhibitory effects of knockdown of HspA12B on migration of human umbilical vein endothelial cells. Collectively, we have discovered that HspA12B is a highly endothelial cell specific distant member of the Hsp70 family that plays a significant role in endothelial cells during development and angiogenesis in vitro, at least partially attributable to modulation of Akt phosphorylation.

Accordingly, the present invention features the use of HSPA12B agonist compounds for promoting endothelial cell health and for treating endothelial cell disorders including but not limited to, atherosclerosis, vascular leak, sepsis, inflammatory disorders, or pre-eclampsia. The present invention also features the use of HSPA12B antagonist compounds for the treatment of patients suffering from angiogenic disorders, including but not limited to cancer, psoriasis, inflammatory disorders, or ocular neovascularization processes. The invention also features diagnostic methods that include the use of HSPA12B nucleic acid molecules, polypeptides, and antibodies for the diagnosis of angiogenic disorders or endothelial cell disorders.

HspA12B Agonists

We have discovered that overexpression of HspA12B enhanced migration and proliferation of endothelial cells and hastened wound healing. Therefore, the invention features HspA12B agonist compounds and the use of HspA12B agonist compounds for the treatment of endothelial cell disorders or to promote endothelial cell health. HspA12B agonist compounds useful in the methods of the invention include, but are not limited to, HspA12B polypeptides or nucleic acid molecules, or fragments, derivatives, homologs, or analogs thereof; agonistic antibodies; growth factors (e.g., VEGF, angiopoietin 1, or angiopoietin 2) that increase the biological activity or expression levels (e.g., in bodily fluids such as blood, serum, urine, plasma, etc.) of HspA12B; compounds that increase the half-life of HspA12B mRNA or protein; compounds that increase the transcription or translation of HspA12B; compounds that decrease the degradation of HspA12B mRNA or protein; compounds that modify the activity of HspA12B, for example to increase HspA12B binding to ATP or HspA12B binding to substrate or to increase HspA12B-mediated phosphorylation of Akt or activation of nitric oxide.

Preferred HspA12B agonist compounds (e.g., polypeptides, fragments or derivatives thereof, or non-peptidyl HspA12B compounds) will have or will induce at least 10%, 25%, 30%, 40%, 50%, 60%, 70%, 80%, 90%, 95%, 96%, 97%, 98%, 99%, or more HspA12B biological activity as described above. Preferably, the HspA12B compound can increase endothelial cell migration or proliferation, decrease endothelial cell death or senescence, reduce blood pressure, decrease vascular permeability, increase endothelial tube formation, increase HspA12B-mediated Akt phosphorylation, or increase HspA12B-mediated nitric oxide activation by at least 10%, 25%, 30%, 40%, 50%, 60%, 70%, 80%, 90%, 95%, 96%, 97%, 98%, 99%, or more as compared to the levels in a cell or a subject not treated with the HspA12B agonist compound.

HspA12B Polypeptides

HspA12B polypeptides, or fragments, analogs, homologs, or derivatives thereof, can be produced by any of a variety of methods for protein production known in the art such as purification of naturally occurring HspA12B products, products of chemical synthetic procedures, and products produced by recombinant techniques from a prokaryotic or eukaryotic host, including, for example, bacterial, fungus, higher plant, insect and mammalian cells. In one example, HspA12B is produced by recombinant DNA methods by inserting a DNA sequence encoding HspA12B, or fragments or derivatives thereof, into a recombinant expression vector and expressing the DNA sequence under conditions promoting expression. General techniques for nucleic acid manipulation are described, for example, by Sambrook et al., in "Molecular Cloning: A Laboratory Manual," 2nd Edition, Cold Spring Harbor Laboratory press, 1989; Goeddel et al., in "Gene Expression Technology: Methods in Enzymology," Academic Press, San Diego, Calif., 1990; Ausubel et al., in "Current Protocols in Molecular Biology," John Wiley & Sons, New York, N.Y., 1998; Watson et al., "Recombinant DNA," Chapter 12, 2nd edition, Scientific American Books, 1992; and other laboratory textbooks. The DNA encoding HspA12B is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences which control the termination of transcription and translation. The ability to replicate in a host, usually conferred by an origin of replication, and a selection gene to facilitate recognition of transformants may additionally be incorporated.

Appropriate cloning and expression vectors for use with bacterial, fungal, yeast, and mammalian cellular hosts can be found, for example, in "Cloning Vectors: A Laboratory Manual," Elsevier, N.Y., 1985, the relevant disclosure of which is hereby incorporated by reference.

Purified HspA12B, or fragments or derivatives thereof, are prepared by culturing suitable host/vector systems to express the recombinant proteins.

In addition to the methods employing recombinant DNA, HspA12B polypeptides, or fragments, homologs, or analogs thereof, can be purified from sources that naturally produce the soluble form of the protein. Examples of these sources include any mammalian tissue or cells, such as endothelial cell lines, endothelial tissue, and vascular tissue. The HspA12B from these sources can be purified and concentrated using any of the methods known in the art or described above.

After purification, HspA12B may be exchanged into different buffers and/or concentrated by any of a variety of methods known to the art, including, but not limited to, filtration and dialysis. The purified HspA12B is preferably at least 85% pure, more preferably at least 95% pure, and most preferably at least 98% pure. Regardless of the exact numerical value of the purity, the HspA112B is sufficiently pure for use as a pharmaceutical product.

HspA12B polypeptides, or fragments or analogs thereof, can also be produced by chemical synthesis (e.g., by the methods described in "Solid Phase Peptide Synthesis," $2^{nd}$ ed., The Pierce Chemical Co., Rockford, Ill., 1984). Modifications to the protein, such as those described below, can also be produced by chemical synthesis.

HspA12B Modifications

The invention encompasses HspA12B polypeptides, or fragments, homologs, analogs, or derivatives thereof, which are modified during or after synthesis or translation. Modifications may provide additional advantages such as increased affinity, decreased off-rate, solubility, stability and in vivo or in vitro circulating time of the polypeptide, or decreased immunogenicity and include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Creighton, "Proteins: Structures and Molecular Properties," 2d Ed., W. H. Freeman and Co., N.Y., 1992; "Postranslational Covalent Modification of Proteins," Johnson, ed., Academic Press, New York, 1983; Seifter et al., *Meth. Enzymol.*, 182:626-646, 1990; Rattan et al., *Ann. NY Acad. Sci.*, 663:48-62, 1992). Additionally, the HSPA12B polypeptide may contain one or more non-classical amino acids. Non-classical amino acids include, but are not limited to, to the D-isomers of the common amino acids, 2,4-diaminobutyric acid, α-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Ca-methyl amino acids, Na-methyl amino acids, and amino acid analogs in general. Furthermore, the amino acid can be D (dextrorotary) or L (levorotary).

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression or truncation of the protein.

As described above, the invention also includes chemically modified derivatives of HspA12B, which may provide additional advantages such as increased solubility, stability and circulating time of the polypeptide, or decreased immunogenicity (see U.S. Pat. No. 4,179,337). The chemical moieties for derivitization may be selected from water soluble polymers such as, for example, polyethylene glycol, ethylene glycol/propylene glycol copolymers, carboxymethylcellulose, dextran, polyvinyl alcohol and the like. The HspA12B polypeptide may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72, (1996); Vorobjev et al., *Nucleosides Nucleotides* 18:2745-2750, (1999); and Caliceti et al., *Bioconjug. Chem.* 10:638-646, (1999), the disclosures of each of which are incorporated by reference.

The polyethylene glycol molecules (or other chemical moieties) should be attached to the HSPA12B polypeptide with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028-1035, (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group. The number of polyethylene glycol moieties attached to each polypeptide of the invention (i.e., the degree of substitution) may also vary. For example, the pegylated HspA12B may be linked, on average, to 1, 2, 3, 4, 5, 6, 7, 8, 9, 10, 12, 15, 17, 20, or more polyethylene glycol molecules. Similarly, the average degree of substitution may range within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per polypeptide molecule. Methods for determining the degree of substitution are discussed, for example, in Delgado et al., *Crit. Rev. Thera. Drug Carrier Sys.*, 9:249-304, 1992.

The HspA12B polypeptides may also be modified with a detectable label, including, but not limited to, an enzyme, prosthetic group, fluorescent material, luminescent material, bioluminescent material, radioactive material, positron emitting metal, nonradioactive paramagnetic metal ion, and affinity label for detection and isolation of a HspA12B target. The detectable substance may be coupled or conjugated either directly to the polypeptides of the invention or indirectly, through an intermediate (such as, for example, a linker known in the art) using techniques known in the art. Examples of suitable enzymes include horseradish peroxidase, alkaline phosphatase, beta-galactosidase, glucose oxidase or acetylcholinesterase; examples of suitable prosthetic group complexes include streptavidin/biotin and avidin/biotin; examples of suitable fluorescent materials include biotin, umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include a radioactive metal ion, e.g., alpha-emitters or other radioisotopes such as, for example, iodine ($^{131}$I, $^{125}$I, $^{123}$I, $^{121}$I), carbon ($^{14}$C), sulfur ($^{35}$S), tritium ($^{3}$H), indium ($^{115}$mIn, $^{113}$mIn, $^{112}$In, $^{111}$In), and technetium ($^{99}$Tc, $^{99}$mTc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, Lu, $^{159}$Gd, $^{149}$Pm, $^{140}$La, $^{175}$Yb, $^{166}$Ho, $^{90}$Y, $^{47}$Sc, $^{186}$R $^{188}$Re, $^{142}$Pr, $^{105}$Rh, $^{97}$Ru, $^{68}$Ge, $^{57}$Co, $^{65}$Zn, $^{85}$Sr, $^{32}$P, $^{53}$Gd, $^{169}$Yb, $^{51}$Cr, $^{54}$Mn, $^{75}$Se, $^{113}$Sn, and $^{117}$Tin. The detectable substance may be coupled or conjugated either directly to the HspA12B polypeptide or indirectly, through an intermediate (such as, for example, a linker known in the art) using techniques known in the art. See, for example, U.S. Pat. No. 4,741,900 for metal ions, which can be conjugated to the HspA12B polypeptide for use as diagnostics according to the present invention.

The HspA12B polypeptide can also be modified by conjugation to another protein or therapeutic compound. Such conjugation can be used, for example, to enhance the stability or solubility of the protein, to reduce the antigenicity, or to enhance the therapeutic effects of the protein. A preferred fusion protein comprises a heterologous region from immunoglobulin (e.g., all or part of the Fc region) that is useful to solubilize proteins (EP-A 0232 262).

A HspA12B polypeptide of the invention may be conjugated to a therapeutic moiety such as a cytotoxin, e.g., a cytostatic or cytocidal agent, a chemotherapeutic agent, a radiotherapeutic agent or a radioactive metal ion.

Techniques known in the art may be applied to label HspA12B polypeptides of the invention. Such techniques include, but are not limited to, the use of bifunctional conjugating agents (see, e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the relevant disclosures of each of which are hereby incorporated by reference in its entirety) and direct coupling reactions (e.g., Bolton-Hunter and Chloramine-T reaction).

Therapeutic Nucleic Acids

The present invention also features HspA12B nucleic acid molecules and the use of HspA12B nucleic acid molecules as agonist compounds. Recent work has shown that the delivery of nucleic acid (DNA or RNA) capable of expressing an endothelial cell mitogen such as VEGF to the site of a blood vessel injury will induce proliferation and reendothelialization of the injured vessel. These general techniques for the delivery of nucleic acid to endothelial cells can be used in the present invention for the delivery of HSPA12B nucleic acids or nucleic acids encoding HSPA12B proteins. These general techniques are described in U.S. Pat. Nos. 5,830,879 and 6,258,787 and are incorporated herein by reference.

In the present invention the nucleic acid may be any HSPA12B nucleic acid (DNA or RNA) including genomic DNA, cDNA, and mRNA, encoding an HSPA12B polypeptide. The nucleic acids encoding the desired protein may be obtained using routine procedures in the art, e.g. recombinant DNA, PCR amplification. For any of the nucleic acid applications described herein, standard methods for administering nucleic acids can be used. Examples are described in U.S. Patent Application Publication No. 20060067937 and PCT Publication No. WO 06/034507.

Compounds that Increase the Levels or Biological Activity of HspA12B

Also included in the present invention as an HspA12B agonist is any compound, such as growth factors, that induce the expression or biological activities of HspA12B polypeptides or nucleic acid molecules as HspA12B agonist compounds. Angiopoietin-1 (Ang-1) and Angiopoietin-2 (Ang-2) are examples of growth factors useful in the methods and compositions of the inventions. Ang-1 is a secreted protein that is approximately 55 kDa in size and the glycosylated forms can be approximately 70 kDa. Ang-2 is a secreted protein that is approximately 55 kDa in size and the glycosylated forms can be approximately 70 kDa. (See, for example, Maisonpierre et al. *Science* 277:55 (1997)). Ang-1 and Ang-2, originally described as mediators of developmental angiogenesis, are peptide ligands that bind the Tie-2 receptor tyrosine kinase found primarily on endothelial cells. Ang-1 and Ang-2 are thought to function as a competitive agonist/antagonist pair for Tie-2 receptor signaling although this dichotomous action appears to be context, dose, and duration specific. Ang-1 appears to promote vessel stability by recruiting pericytes to nascent blood vessels and preserving cell-cell contacts.

VEGF is another example of a growth factor useful in the methods and compositions of the invention (see for example U.S. Pat. Nos. 5,332,671; 5,240,848; 5,194,596; and Charnock-Jones et al. (*Biol. Reproduction*, 48: 1120-1128, 1993). VEGF exists as a glycosylated homodimer and includes at least four different alternatively spliced isoforms. The biological activity of native VEGF includes the promotion of selective growth of vascular endothelial cells or umbilical vein endothelial cells and induction of angiogenesis. As used herein, VEGF includes any VEGF family member or isoform (e.g., VEGF-A, VEGF-B, VEGF-C, VEGF-D, VEGF-E, VEGF189, VEGF165, or VEGF 121). Preferably, VEGF is the VEGF121 or VEGF165 isoform (Tischer et al., *J. Biol. Chem.* 266, 11947-11954, 1991; Neufed et al. *Cancer Metastasis* 15:153-158, 1996), which is described in U.S. Pat. Nos. 6,447,768; 5,219,739; and 5,194,596, hereby incorporated by reference. Also included are mutant forms of VEGF such as the KDR-selective VEGF and Flt-selective VEGF described in Gille et al. (*J. Biol. Chem.* 276:3222-3230, 2001). As used herein VEGF also includes any modified forms of VEGF such as those described in LeCouter et al. (*Science* 299:890-893, 2003).

The growth factors used in the methods of the invention can include any mammalian form of the growth factor or any fragment, homolog, analog, derivative, or modification thereof. The methods described herein for purification and modification of the HspA12B proteins can also apply to the purification and modification of the growth factors as HspA12B agonist compounds.

HspA12B Antagonist Compounds

We have discovered that reduction of HspA12B levels inhibits migration of endothelial cells and reduces endothelial tube formation. Therefore, the invention features HspA12B antagonist compounds for the treatment of angiogenic disorders. HspA12B antagonist compounds useful in the methods of the invention include, but are not limited to, fragments of HspA12B (e.g., dominant negative fragments or fragments that are unable to bind ATP or substrate); peptidyl or non-peptidyl compounds that specifically bind HspA12B (e.g., antibodies or antigen-binding fragments thereof), for example at the ATP binding domain or substrate binding domain of HspA12B; antisense nucleobase oligomers; small RNA; small molecule inhibitors; compounds that decrease the half-life of HspA12B mRNA or protein; compounds that decrease transcription or translation of HspA12B; compounds that reduce or inhibit the expression levels (e.g., in bodily fluids such as blood, serum, urine, plasma, etc.) of HspA12B polypeptides or decrease the biological activity of HspA12B polypeptides; compounds that increase the expression or biological activity of a HspA12B inhibitor (e.g., an inhibitor that blocks binding to a substrate or ATP); and compounds that block HspA12B-mediated phosphorylation of Akt or activation of nitric oxide.

Preferred HspA12B antagonist compounds will reduce or inhibit HspA12B biological activity or expression levels by at least 10% 25%, 30%, 40%, 50%, 60%, 70%, 80%, 90%, 95%, 96%, 97%, 98%, 99%, or more. Preferably, the HspA12B compound can reduce or inhibit endothelial cell migration or proliferation, increase endothelial cell death or senescence, reduce or inhibit endothelial tube formation, reduce or inhibit heat shock protein or chaperone activity, reduce or inhibit ATP binding ability, reduce or inhibit HspA12B-mediated phosphorylation of Akt, and reduce or inhibit HspA12B-mediated activation of nitric oxide by at least 25%, 30%, 40%, 50%, 60%, 70%, 80%, 90%, 95%, 96%, 97%, 98%, 99%, or more.

Antagonistic Polypeptides

Polypeptides that specifically bind to HspA12B and inhibit the biological activity of HspA12B are included in the invention and can be used in the methods and compositions of the invention that require HspA12B antagonist compounds. Preferred polypeptides include dominant negative fragments of HspA12B or polypeptides that bind to functional regions of the HSPA12B protein, for example, the ATP binding domain or the substrate-binding domain. By binding to the functional domain, the polypeptide can inhibit the activity of HSPA12B, presumably by steric interference. Any polypeptide that is used as an antagonist compound can be produced, purified, and/or modified using any of the methods and modifications described herein.

Antibodies

Antibodies that specifically bind to HspA12B, have a high affinity for HspA12B and/or neutralize or prevent HspA12B activity are useful in the therapeutic methods of the invention. In one embodiment, the antibody, or fragment or derivative thereof, binds to the ATP binding domain or substrate binding domain of HspA12B.

Compositions, for example including excipients, of any of the above antibodies are also included in the invention. Methods for the preparation and use of antibodies for therapeutic purposes are described in several patents including U.S. Pat. Nos. 6,054,297; 5,821,337; 6,365,157; and 6,165,464 and are incorporated herein by reference. Antibodies can be polyclonal or monoclonal; monoclonal antibodies are preferred.

Anti-HspA12B antibodies may be produced by methods known in the art. These methods include the immunological method described by Kohler and Milstein (*Nature*, 256: 495-497, 1975), Kohler and Milstein (*Eur. J. Immunol*, 6, 511-519, 1976), and Campbell ("Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam, 1985), as well as by the recombinant DNA method described by Huse et al. (*Science*, 246, 1275-1281, 1989). For example, antibodies can be screened using standard art-known methods such as ELISA against the HspA12B peptide antigen or western blot analysis. Non-limiting examples of such techniques are described in Examples II and III of U.S. Pat. No. 6,365,157, herein incorporated by reference.

The antibody may be prepared in any mammal, including mice, camels, rats, rabbits, goats, and humans. The antibody may be a member of one of the following immunoglobulin classes: IgG, IgM, IgA, IgD, or IgE, and the subclasses thereof, and preferably is an IgG antibody.

In one example the following amino acid sequence from the mouse HspA12B was used to generate an anti-HspA12B antibody: CVDVSTNRSVRAAIDFLSN (SEQ ID NO: 19).

While the preferred animal for producing monoclonal antibodies is mouse, the invention is not so limited; in fact, human antibodies may be used and may prove to be preferable. Such antibodies can be obtained by using human hybridomas (Cole et al., "Monoclonal Antibodies and Cancer Therapy", Alan R. Liss Inc., p. 77-96, 1985). Techniques developed for the production of antibodies of the invention, including chimeric antibodies are described, for example, in Morrison et al., *Proc. Natl. Acad. Sci.* 81, 6851-6855, 1984; Neuberger et al., *Nature* 312, 604-608, 1984; Takeda et al., *Nature* 314, 452-454, 1985; Crawford et al., *J. Gen. Virol.*, 64:697-700, 1983; Kozbor and Roder, *J. Immunol.*, 4:1275-1280, 1981; Kozbor et al., *Methods Enzymol.*, 121:120-140, 1986).

The invention also includes functional equivalents or derivatives of the antibodies described in this specification. Functional equivalents or derivatives include polypeptides with amino acid sequences substantially identical to the amino acid sequence of the variable or hypervariable regions of the antibodies of the invention. Functional equivalents have binding characteristics comparable to those of the antibodies, and include, for example, chimerized, humanized and single chain antibodies, antibody fragments, and antibodies, or fragments thereof, fused to a second protein, or fragment thereof. Methods of producing such functional equivalents are disclosed, for example, in PCT Publication No. WO93/21319; European Patent No. 0 239 400 B 1; PCT Publication No. WO89/09622; European Patent Application No. 0338,745; European Patent Application No. 0332424; and U.S. Pat. No. 4,816,567; Morrison et al., *Proc. Natl. Acad. Sci. USA*, 81:6851-6855, 1984; Boulianne et al., *Nature*, 312:643-646, 1984; Neuberger et al., *Nature*, 314:268-270, 1985, each of which is herein incorporated by reference.

Chimerized antibodies preferably have constant regions derived substantially or exclusively from human antibody constant regions and variable regions derived substantially or exclusively from the sequence of the variable region from a mammal other than a human. Such humanized antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Methods for humanizing non-human antibodies are well known in the art (for reviews see Vaswani and Hamilton, *Ann. Allergy Asthma Immunol.*, 81:105-119, 1998 and Carter, *Nature Reviews Cancer*, 1:118-129, 2001). Generally, a humanized antibody has one or more amino acid residues introduced into it from a source that is non-human. These non-human amino acid residues are often referred to as import residues, which are typically taken from an import variable domain. Humanization can be essentially performed following the methods known in the art (Jones et al., *Nature,* 321:522-525, 1986; Riechmann et al., *Nature,* 332:323-329, 1988; and Verhoeyen et al., *Science,* 239:1534-1536 1988), by substituting rodent CDRs or other CDR sequences for the corresponding sequences of a human antibody. Accordingly, such humanized antibodies are chimeric antibodies wherein substantially less than an intact human variable domain has been substituted by the corresponding sequence from a non-human species (see for example, U.S. Pat. No. 4,816,567). In practice, humanized antibodies are typically human antibodies in which some CDR residues and possibly some FR residues are substituted by residues from analogous sites in rodent antibodies (Presta, *Curr. Op. Struct. Biol.,* 2:593-596, 1992).

Additional methods for the preparation of humanized antibodies can be found in U.S. Pat. Nos. 5,821,337, and 6,054, 297, and Carter, (supra) which are all incorporated herein by reference. The humanized antibody is selected from any class of immunoglobulins, including IgM, IgG, IgD, IgA and IgE, and any isotype, including $IgG_1$, $IgG_2$, $IgG_3$, and $IgG_4$. Where cytotoxic activity is not needed, such as in the present invention, the constant domain is preferably of the $IgG_2$ class. The humanized antibody may comprise sequences from more than one class or isotype, and selecting particular constant domains to optimize desired effector functions is within the ordinary skill in the art.

Human antibodies can also be produced using various techniques known in the art, including phage display libraries (Marks et al., *J. Mol. Biol.,* 222:581-597, 1991 and Winter et al. *Annu. Rev. Immunol.,* 12:433-455, 1994). The techniques of Cole et al. and Boerner et al. are also useful for the preparation of human monoclonal antibodies (Cole et al., supra; Boerner et al., *J. Immunol.,* 147: 86-95, 1991).

Functional equivalents of antibodies also include single-chain antibody fragments, also known as single-chain antibodies (scFvs) and fragments of antibodies that have the same or comparable binding characteristics to those of the whole antibody. Such fragments may contain one or both Fab fragments or the $F(ab')_2$ fragment. Preferably the antibody fragments contain all six CDRs of the whole antibody, although fragments containing fewer than all of such regions, such as three, four or five CDRs, are also functional.

Functional equivalents may be or may combine members of any one of the following immunoglobulin classes: IgG, IgM, IgA, IgD, or IgE, and the subclasses thereof. Equivalents of antibodies are prepared by methods known in the art. For example, fragments of antibodies may be prepared enzymatically from whole antibodies. Preferably, equivalents of antibodies are prepared from DNA encoding such equivalents. DNA encoding fragments of antibodies may be prepared by deleting all but the desired portion of the DNA that encodes the full-length antibody.

DNA encoding chimerized antibodies may be prepared by recombining DNA substantially or exclusively encoding human constant regions and DNA encoding variable regions derived substantially or exclusively from the sequence of the variable region of a mammal other than a human. DNA encoding humanized antibodies may be prepared by recombining DNA encoding constant regions and variable regions other than the CDRs derived substantially or exclusively from the corresponding human antibody regions and DNA encoding CDRs derived substantially or exclusively from a manual other than a human.

Antagonistic Nucleic Acid Molecules

The present invention also features antisense nucleobase oligomers to HspA12B and the use of such oligomers to downregulate expression of HspA12B mRNA. By binding to the complementary nucleic acid sequence (the sense or coding strand), antisense nucleobase oligomers are able to inhibit protein expression presumably through the enzymatic cleavage of the RNA strand by RNAse H. Preferably the antisense nucleobase oligomer is capable of reducing HspA12B protein expression in a cell that expresses increased levels of HspA12B. Preferably the decrease in HspA12B protein expression is at least 10% relative to cells treated with a control oligonucleotide, preferably 20% or greater, more preferably 40%, 50%, 60%, 70%, 80%, 90% or greater. Methods for selecting and preparing antisense nucleobase oligomers are well known in the art. Methods for assaying levels of protein expression are also well known in the art and include western blotting, immunoprecipitation, and ELISA.

One example of an antisense nucleobase oligomer particularly useful in the methods and compositions of the invention is a morpholino oligomer. Morpholinos are used to block access of other molecules to specific sequences within nucleic acid molecules. They can block access of other molecules to small (~25 base) regions of ribonucleic acid (RNA). Morpholinos are sometimes referred to as PMO, an acronym for phosphorodiamidate morpholino oligo.

Morpholinos are used to knock down gene function by preventing cells from making a targeted protein or by modifying the splicing of pre-mRNA. Morpholinos are synthetic molecules that bind to complementary sequences of RNA by standard nucleic acid base-pairing. While morpholinos have standard nucleic acid bases, those bases are bound to morpholine rings instead of deoxyribose rings and linked through phosphorodiamidate groups instead of phosphates. Replacement of anionic phosphates with the uncharged phosphorodiamidate groups eliminates ionization in the usual physiological pH range, so morpholinos in organisms or cells are uncharged molecules.

Morpholinos act by "steric blocking" or binding to a target sequence within an RNA and blocking molecules which might otherwise interact with the RNA. Because of their completely unnatural backbones, morpholinos are not recognized by cellular proteins. Nucleases do not degrade morpholinos and morpholinos do not activate toll-like receptors and so they do not activate innate immune responses such as the interferon system or the NF-κB mediated inflammation response. Morpholinos are also not known to modify methylation of DNA. Therefore, morpholinos directed to any part of HspA12B and that reduce or inhibit the expression levels or biological activity of HspA12B are particularly useful in the methods and compositions of the invention that require the use of HspA12B antagonistic compounds.

The present invention also features the use of RNA interference (RNAi) to inhibit expression of HspA12B. RNAi is a form of post-transcriptional gene silencing initiated by the introduction of double-stranded RNA (dsRNA). Short 15 to 32 nucleotide double-stranded RNAs, known generally as "siRNAs," "small RNAs," or "microRNAs" are effective at down-regulating gene expression in nematodes (Zamore et al., *Cell* 101: 25-33) and in mammalian tissue culture cell lines (Elbashir et al., *Nature* 411:494-498, 2001, hereby incorporated by reference). The further therapeutic effectiveness of this approach in mammals was demonstrated in vivo by McCaffrey et al. (*Nature* 418:38-39. 2002). The small RNAs are at least 15 nucleotides, preferably, 17, 18, 19, 20, 21, 22, 23, 24, 25, 26, 27, 28, 29, 30, 31, 32, 33, 34, 35, nucleotides in length and even up to 50 or 100 nucleotides in length (inclusive of all integers in between). Such small RNAs that are substantially identical to or complementary to any region of HspA12B, are included in the invention.

Therefore, the invention includes any small RNA substantially identical to at least 15 nucleotides, preferably, 17, 18, 19, 20, 21, 22, 23, 24, 25, 26, 27, 28, 29, 30, 31, 32, 33, 34, or 35, nucleotides in length and even up to 50 or 100 nucleotides in length (inclusive of all integers in between) of any region of HspA12B. It should be noted that longer dsRNA fragments can be used that are processed into such small RNAs. Useful small RNAs can be identified by their ability to decrease HspA12B expression levels or biological activity. Small RNAs can also include short hairpin RNAs in which both strands of an siRNA duplex are included within a single RNA molecule.

The specific requirements and modifications of small RNA are known in the art and are described, for example, in PCT Publication No. WO01/75164, and U.S. Application Publication Numbers 20060134787, 20050153918, 20050058982, 20050037988, and 20040203145, the relevant portions of which are herein incorporated by reference. In particular embodiments, siRNAs can be synthesized or generated by processing longer double-stranded RNAs, for example, in the presence of the enzyme dicer under conditions in which the dsRNA is processed to RNA molecules of about 17 to about 26 nucleotides. siRNAs can also be generated by expression of the corresponding DNA fragment (e.g., a hairpin DNA construct). Generally, the siRNA has a characteristic 2- to 3-nucleotide 3' overhanging ends, preferably these are (2'-deoxy)thymidine or uracil. The siRNAs typically comprise a 3' hydroxyl group. In some embodiments, single stranded siRNAs or blunt ended dsRNA are used. In order to further enhance the stability of the RNA, the 3' overhangs are stabilized against degradation. In one embodiment, the RNA is stabilized by including purine nucleotides, such as adenosine or guanosine. Alternatively, substitution of pyrimidine nucleotides by modified analogs e.g. substitution of uridine 2-nucleotide overhangs by (2'-deoxy)thymide is tolerated and does not affect the efficiency of RNAi. The absence of a 2' hydroxyl group significantly enhances the nuclease resistance of the overhang in tissue culture medium.

siRNA molecules can be obtained through a variety of protocols including chemical synthesis or recombinant production using a Drosophila in vitro system. They can be commercially obtained from companies such as Dharmacon Research Inc. or Xeragon Inc., or they can be synthesized using commercially available kits such as the Silencer™ siRNA Construction Kit from Ambion (catalog number 1620) or HiScribe™ RNAi Transcription Kit from New England BioLabs (catalog number E2000S).

Alternatively siRNA can be prepared using standard procedures for in vitro transcription of RNA and dsRNA annealing procedures such as those described in Elbashir et al. (*Genes & Dev.*, 15:188-200, 2001), Girard et al., (*Nature* Jun. 4, 2006, e-publication ahead of print), Aravin et al., (*Nature* Jun. 4, 2006, e-publication ahead of print), Grivna et al., (*Genes Dev.* Jun. 9, 2006, e-publication ahead of print), and Lau et al., (*Science* Jun. 15, 2006, e-publication ahead of print). siRNAs are also obtained by incubation of dsRNA that corresponds to a sequence of the target gene in a cell-free Drosophila lysate from syncytial blastoderm Drosophila embryos under conditions in which the dsRNA is processed to generate siRNAs of about 21 to about 23 nucleotides, which are then isolated using techniques known to those of skill in the art. For example, gel electrophoresis can be used to separate the 21-23 nt RNAs and the RNAs can then be eluted from the gel slices. In addition, chromatography (e.g. size exclusion chromatography), glycerol gradient centrifugation, and affinity purification with antibody can be used to isolate the small RNAs.

Short hairpin RNAs (shRNAs), as described in Yu et al. or Paddison et al. (*Proc. Natl. Acad. Sci. USA*, 99:6047-6052, 2002; *Genes & Dev,* 16:948-958, 2002; incorporated herein by reference), can also be used in the methods of the invention. shRNAs are designed such that both the sense and antisense strands are included within a single RNA molecule and connected by a loop of nucleotides (3 or more). shRNAs can be synthesized and purified using standard in vitro T7 transcription synthesis as described above and in Yu et al. (supra). shRNAs can also be subcloned into an expression vector that has the mouse U6 promoter sequences which can then be transfected into cells and used for in vivo expression of the shRNA.

A variety of methods are available for transfection, or introduction, of dsRNA into mammalian cells. For example, there are several commercially available transfection reagents useful for lipid-based transfection of siRNAs including but not limited to: TransIT-TKO™ (Mirus, Cat. # MIR 2150), Transmessenger™ (Qiagen, Cat. #301525), Oligofectamine™ and Lipofectamine™ (Invitrogen, Cat. #MIR 12252-011 and Cat. #13778-075), siPORT™ (Ambion, Cat. #1631), DharmaFECT™ (Fisher Scientific, Cat. #T-2001-01). Agents are also commercially available for electroporation-based methods for transfection of siRNA, such as siPORTer™ (Ambion Inc. Cat. #1629). Microinjection techniques can also be used. The small RNA can also be transcribed from an expression construct introduced into the cells, where the expression construct includes a coding sequence for transcribing the small RNA operably linked to one or more transcriptional regulatory sequences. Where desired, plasmids, vectors, or viral vectors can also be used for the delivery of dsRNA or siRNA and such vectors are known in the art. Protocols for each transfection reagent are available from the manufacturer. Additional methods are known in the art and are described, for example in U.S. Patent Application Publication No. 20060058255.

Therapeutic Methods

We have discovered that HspA12B agonist compounds can be used to treat or prevent endothelial cell disorders or to promote endothelial cell health in a subject and that HspA12B antagonist compounds can be used to treat or prevent angiogenic disorders in a subject. The various disorders that can be treated or prevented using the methods of the invention are described below.

Treatment of Angiogenic Disorders

Any of the HspA12B antagonist compounds described herein can be used to treat or prevent an angiogenic disorder in a subject. Angiogenesis is a complex, combinatorial process that is regulated by a balance between pro- and anti-angiogenic molecules. Angiogenic stimuli (e.g. hypoxia or inflammatory cytokines) result in the induced expression and release of angiogenic growth factors such as vascular endothelial growth factor (VEGF) or fibroblast growth factor (FGF). These growth factors stimulate endothelial cells in the existing vasculature to proliferate and migrate through the tissue to form new endothelialized channels. There are a variety of diseases in which angiogenesis is believed to be important, referred to as angiogenic diseases or disorders, including but not limited to cancer, particularly cancers which require neovascularization to support tumor growth, infectious diseases, autoimmune disorders, vascular malformations, DiGeorge syndrome, HHT, cavernous hemangioma, atherosclerosis, transplant arteriopathy, vascular access stenosis associated with hemodialysis, vasculitis, vasculitidis, obesity, psoriasis, warts, allergic dermatitis, scar keloids, pyogenic granulomas, blistering disease, Kaposi sarcoma, persistent hyperplastic vitreous syndrome, retinopathy of prematurity, choroidal neovascularization, macular degeneration, diabetic retinopathy, ocular neovascularization, primary pulmonary hypertension, asthma, nasal polyps, inflammatory bowel and periodontal disease, ascites, peritoneal adhesions, contraception, endometriosis, uterine bleeding, ovarian cysts, ovarian hyperstimulation, arthritis, rheumatoid arthritis, chronic articular rheumatism, synovitis, osteoarthritis, osteomyelitis, and osteophyte formation.

We have found that overexpression of HSPA12B can increase the migration of endothelial cells and cause cells to become more angiogenic. Thus, HSPA12B antagonist compounds can be used as a therapeutic to block blood vessel formation and to treat angiogenic disorders.

Angiogenic disorders can be diagnosed using standard techniques known in the art, such as detection of markers of angiogenesis (e.g., increased VEGF and other pro-angiogenic molecules or decreased anti-angiogenic molecules). The therapeutic effectiveness of HspA12B antagonist compounds, including fragments or derivatives thereof, can be measured using in vitro and in vivo assays well known in the art. (See for example Heeschen et al., *J. Clin. Invest.* 110:527-536, (2002)). Assays include any of the assays for HspA12B biological activity as described herein wherein a compound that reduces or inhibits HspA12B biological activity is considered a compound useful for the treatment or prevention of an angiogenic disorder.

In addition, assays can include angiogenesis assays known in the art. One particular assay measures angiogenesis in the chick chorioallantoic membrane (CAM) and is referred to as the CAM assay. See Ausprunk et al., *Am. J. Pathol.*, 79:597-618, 1975; and Ossonski et al., *Cancer Res.*, 40:2300-2309, 1980. The CAM assay is a well recognized assay model for in vivo angiogenesis because neovascularization of whole tissue is occurring, and actual chick embryo blood vessels are growing into the CAM or into the tissue grown on the CAM.

Another assay for measuring angiogenesis is the in vivo rabbit eye model and is referred to as the rabbit eye assay. The rabbit eye assay has been described in detail by others, and further has been used to measure both angiogenesis and neovascularization in the presence of angiogenic inhibitors such as thalidomide. See D'Amato et al., *Proc. Natl. Acad. Sci.* 91:4082-4085, 1994. The rabbit eye assay is a well recognized assay model for in vivo angiogenesis because the neovascularization process, exemplified by rabbit blood vessels growing from the rim of the cornea into the cornea, is easily visualized through the naturally transparent cornea of the eye. Additionally, both the extent and the amount of inhibition of neovascularization or regression of neovascularization can easily be monitored over time.

A further assay for measuring angiogenesis in the chimeric mouse:human mouse model and is referred to as the chimeric mouse assay. The assay has been described in detail by others, and further has been described herein to measure angiogenesis, neovascularization, and regression of tumor tissues. See Yan, et al., *J. Clin. Invest.* 91:986-996, 1993. The chimeric mouse assay is a useful assay model for in vivo angiogenesis because the transplanted skin grafts closely resemble normal human skin histologically and neovascularization of whole tissue is occurring wherein actual human blood vessels are growing from the grafted human skin into the human tumor tissue on the surface of the grafted human skin. The origin of the neovascularization into the human graft can be demonstrated by immunohistochemical staining of the neovasculature with human-specific endothelial cell markers. The chimeric mouse assay demonstrates regression of neovascularization based on both the amount and extent of regression of new vessel growth. Furthermore, it is easy to monitor effects on the growth of any tissue transplanted upon the grafted skin, such as a tumor tissue.

In addition, the zebrafish assays described herein (e.g., microangiopathy and visualization of circulation defects) are useful assays for identifying HspA12B antagonist compounds.

HspA12B antagonist compounds useful in the methods of the invention can be identified using any of the assays described above. Preferred HspA12B antagonist compounds will generally reduce or inhibit angiogenesis by at least 10%, 20%, 30%, 40%, 50%, 60%, 70%, 80%, 90%, or more.

Combination Therapies

In various embodiments HspA12B antagonist compounds can be provided in conjunction (e.g., before, during, or after) with additional therapies for reducing or inhibiting angiogenesis or for treating or preventing an angiogenic disorder.

Angiogenesis inhibitors, also known as anti-angiogenic agents, that may be used in combination with any of the HspA12B antagonist compounds include an anti-angiogenic antibody, an antibody that binds VEGF-A, an antibody that binds a VEGF receptor and blocks VEGF binding, avastin, endostatin, angiostatin, restin, tumstatin, TNP-470, 2-methoxyestradiol, lucentis, macugen, thalidomide, a peptide fragment of an anti-angiogenic protein, canstatin, arrestin, a VEGF kinase inhibitor, CPTK787, SFH-1, an anti-angiogenic protein, thrombospondin-1, platelet factor-4, interferon-α, an agent that blocks TIE-1 or TIE-2 signaling, or PIH12 signaling, an agent that blocks an extracellular vascular endothelial (VE) cadherin domain, an antibody that binds to an extracellular VE-cadherin domain, tetracycline, penicillamine, vinblastine, cytoxan, edelfosine, tegafur or uracil, curcumin, green tea, genistein, resveratrol, N-acetyl cysteine, captopril, a cox-2 inhibitor, celecoxib, and rofecoxib.

The dosage of the angiogenesis inhibitor will depend on other clinical factors such as weight and condition of the human or animal and the route of administration of the compound. For treating humans or animals, between approximately 0.5 mg/kg to 500 mg/kg body weight of the angiogenesis inhibitor can be administered. A more preferable range is 1 mg/kg to 100 mg/kg body weight with the most preferable range being from 2 mg/kg to 50 mg/kg body weight. Depending upon the half-life of the angiogenesis inhibitor in the particular animal or human, the angiogenesis inhibitor can be administered between several times per day to once a week. The methods of the present invention provide for single as well as multiple administrations, given either simultaneously or over an extended period of time.

For therapeutic applications that are used for the treatment of angiogenic disorders that include cancer, the HspA12B antagonist compound can be provided in conjunction (e.g., before, during, or after) with additional therapies for treating or preventing tumor growth or metastasis. Treatment therapies include but are not limited to surgery, radiation therapy, chemotherapy, biologic therapy (e.g., cytokines, immunotherapy, and interferons), differentiating therapy, immune therapy, anti-angiogenic therapy, hormone therapies, or hyperthermia. HspA12B antagonist compounds may be formulated alone or in combination with any additional cancer therapies in a variety of ways that are known in the art. Such additional cancer therapies can be administered before, during, or after the administration of HspA12B antagonist compounds.

Treatment of Endothelial Cell Disorders and Promotion of Endothelial Cell Health Any of the HspA12B agonist compounds described herein can be used to treat or prevent an endothelial cell disorder in a subject or to promote endothelial cell health in a subject. Endothelial cell health is measured by any of the following criteria: endothelial cell proliferation and prevention or inhibition of endothelial cell death or senescence; endothelial cell migration; the ability to form a barrier and prevent the movement of molecules and cells through the barrier; the ability to maintain anti-coagulation function; and the ability to maintain vascular tone. An endothelial cell that is considered healthy will have normal levels (i.e., a level equivalent to that found in a normal endothelial cell) of any of the above parameters for endothelial cell function.

There are a variety of diseases in which endothelial cell health is believed to be important, referred to as endothelial cell diseases or disorders. In general, endothelial disease is characterized by insufficient angiogenesis, vascular leak, altered vasomotor tone, anti-coagulation properties, hypertension, vasoconstriction, and anti-inflammatory properties. Examples of such disorders include, but are not limited to Alzheimer's disease, amyotrophic lateral sclerosis, diabetic neuropathy, stroke, atherosclerosis, diabetes, restenosis, coronary artery disease, peripheral vascular disease, vascular leak, vasculitis, vasculitidis, Wegner's disease, gastric or oral ulcerations, cirrhosis, hepatorenal syndrome, Crohn's disease, hair loss, skin purpura, telangiectasia, venous lake formation, delayed wound healing, pre-eclampsia, sepsis, ischemia-reperfusion injury, hypertension, chronic or acute infection, menorrhagia, neonatal respiratory distress, pulmonary fibrosis, emphysema, nephropathy, glomerulonephritis, sclerodoma, and vascular abnormalities.

We have found that a reduction in the expression of HspA12B can decrease the migration of endothelial cells, can cause poor endothelial tube formation and can block Akt phosphorylation which is involved in endothelial cell migration. Thus, HspA12B agonists can be used as a therapeutic to promote endothelial cell health, to promote neovascularization, and to prevent vascular leakage.

Endothelial cell disorders can be diagnosed using standard techniques known in the art, including, for example, diagnostic methods for pre-eclampsia (as described in U.S. Patent Application Publication No. 20050170444), and blood pressure measurement, assessment of the arm brachial index, ultrasonic scanning, angiography, CT, and MRI to detect circulatory obstruction. The therapeutic effectiveness of HspA12B agonist compounds can be measured using in vitro and in vivo assays well known in the art including any of the assays for HspA12B biological activity or for endothelial cell health, as described herein. In one example, measurements of total circulating endothelial cells or measurement of endothelial precursor cells are used as an indicator of endothelial cell health. (See for example, Goon et al., *Neoplasia* 8:79-88 (2006), Aicher et al., *Hypertension* 45:321-325 (2005), and Ingram et al., *Blood* 106:1525-1531 (2005)).

HspA12B agonist compounds useful in the methods of the invention can be identified using any of the assays described above. Preferred HspA12B agonist compounds will generally increase HspA12B biological activity or expression levels by at least 10%, 20%, 30%, 40%, 50%, 60%, 70%, 80%, 90%, or more.

Combination Therapies

In various embodiments HspA12B agonist compounds can be provided in conjunction (e.g., before, during, or after) with additional therapies for promoting endothelial cell health or for treating or preventing an endothelial cell disorder. Such therapies are known in the art and include the administration of pro-angiogenic factors such as VEGF (including all isoforms), Ang-1, and growth factors such as PDGF, TGF-β, and bFGF.

HspA12B Antagonists for the Induction of Vascular Leak

For certain applications, a temporary state of vascular leak is desired. Such applications include the need to break down the blood-brain barrier to treat diseases such as brain diseases or brain tumors, in which CNS penetration is needed. Other therapeutic applications of vascular leak include localized breakdown of the capillary permeability barrier to promote fluid and phagocyte extravasation (to clear infection from poorly perfused areas such as synovial cavities), and to promote loss of proteins and other molecules into urine by increasing renal capillary permeability. For such applications, an HspA12B antagonist can be used to induce the state of vascular leak. Any of the HspA12B antagonist compounds can be prepared and administered using any of the methods described.

Therapeutic Formulations

The invention includes the use of HspA12B antagonists to treat, prevent or reduce angiogenic disorders in a subject. The HspA12B antagonist can be administered at anytime, for example, after diagnosis or detection of an angiogenic disorder, or for prevention of an angiogenic disorder in subjects that have not yet been diagnosed with an angiogenic disorder but are at risk of developing such a disorder, or after a risk of developing an angiogenic disorder is determined. The invention also includes the use of HspA12B agonist compounds to treat, prevent, or reduce endothelial cell disorders in a subject. The HspA12B agonist compound can be administered at anytime, for example, after diagnosis or detection of an endothelial cell disorder, or for prevention of an endothelial cell disorder in subjects that have not yet been diagnosed with an endothelial cell disorder but are at risk of developing such a disorder, or after a risk of developing an endothelial cell disorder is determined, or to promote neovascularization or endothelial cell health in an individual in need of such a therapy.

An HspA12B agonist or antagonist compound of the invention may be formulated within a pharmaceutically-acceptable diluent, carrier, or excipient, in unit dosage form. Conventional pharmaceutical practice may be employed to provide suitable formulations or compositions to administer HspA12B agonist or antagonist compound of the invention to patients suffering from an angiogenic disorder or an epithelial cell disorder. Administration may begin before the patient is symptomatic. The HspA12B agonist and antagonist compounds of the present invention can be formulated and administered in a variety of ways, e.g., those routes known for specific indications, including, but not limited to, topically, orally, subcutaneously, bronchioscopic injection, intravenously, intracerebrally, intranasally, transdermally, intraperitoneally, intramuscularly, intrapulmonary, vaginally, rectally, intraarterially, intralesionally, parenterally, intraventricularly in the brain, or intraocularly. The HspA12B agonist or antagonist compound can be in the form of a pill, tablet, capsule, liquid, or sustained release tablet for oral administration; or a liquid for intravenous administration, subcutaneous administration, or injection; for intranasal formulations, in the form of powders, nasal drops, or aerosols; or a polymer or other sustained release vehicle for local administration.

Therapeutic formulations are prepared using standard methods known in the art by mixing the active ingredient having the desired degree of purity with optional physiologically acceptable carriers, excipients or stabilizers (Remington's Pharmaceutical Sciences (20$^{th}$ edition), ed. A. Gennaro, 2000, Lippincott, Williams & Wilkins, Philadelphia, Pa.), in the form of lyophilized formulations or aqueous solutions. Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant. Preferred surfactants are non-ionic detergents.

For parenteral administration, the HspA12B agonist or antagonist compounds are formulated in a unit dosage injectable form (solution, suspension, emulsion) in association with a pharmaceutically acceptable parenteral vehicle. Such vehicles are inherently nontoxic, and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives.

The dosage required depends on the choice of the route of administration; the nature of the formulation; the nature of the subject's illness; the subject's size, weight, surface area, age, and sex; other drugs being administered; and the judgment of the attending physician. Wide variations in the needed dosage are to be expected in view of the variety of polypeptides and fragments available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 6-, 8-, 10-, 20-, 50-, 100-, 150-, or more). Encapsulation of the polypeptide in a suitable delivery vehicle (e.g., polymeric microparticles or implantable devices) may increase the efficiency of delivery, particularly for oral delivery.

As described above, the dosage of the HspA12B agonist or antagonist compound will depend on other clinical factors such as weight and condition of the subject and the route of administration of the compound. For treating subjects, between approximately 0.01 mg/kg to 500 mg/kg body weight of the HspA12B agonist or antagonist compound can be administered. A more preferable range is 0.01 mg/kg to 50 mg/kg body weight with the most preferable range being from 1 mg/kg to 25 mg/kg body weight. Depending upon the half-life of the HspA12B agonist or antagonist compound in the particular subject, the HspA12B agonist or antagonist compound can be administered between several times per day to once a week. The methods of the present invention provide for single as well as multiple administrations, given either simultaneously or over an extended period of time.

Alternatively, a polynucleotide containing a nucleic acid sequence encoding an HspA12B agonist or antagonist compound can be delivered to the appropriate cells in the subject. Expression of the coding sequence can be directed to any cell in the body of the subject, preferably an endothelial cell. This can be achieved by, for example, the use of polymeric, biodegradable microparticle or microcapsule delivery devices known in the art.

The nucleic acid can be introduced into the cells by any means appropriate for the vector employed. Many such methods are well known in the art (Sambrook et al., supra, and Watson et al., Recombinant DNA, Chapter 12, 2d edition, Scientific American Books, 1992). Examples of methods of gene delivery include liposome mediated transfection, electroporation, calcium phosphate/DEAE dextran methods, gene gun, and microinjection.

In gene therapy applications, genes are introduced into cells in order to achieve in vivo synthesis of a therapeutically effective genetic product. "Gene therapy" includes both conventional gene therapy where a lasting effect is achieved by a single treatment, and the administration of gene therapeutic agents, which involves the one time or repeated administration of a therapeutically effective DNA or mRNA. Standard gene therapy methods typically allow for transient protein expression at the target site ranging from several hours to several weeks. Re-application of the nucleic acid can be utilized as needed to provide additional periods of expression of HspA12B agonist or antagonist compounds.

Alternatively, tissue specific targeting can be achieved by the use of tissue- or cell-specific transcriptional regulatory elements which are known in the art (e.g., endothelial cell specific promoters or enhancers). Delivery of "naked DNA" (i.e., without a delivery vehicle) to an intramuscular, intradermal, or subcutaneous site is another means to achieve in vivo expression.

Gene delivery using viral vectors such as adenoviral, retroviral, lentiviral, or adeno-associated viral vectors can also be used. Numerous vectors useful for this purpose are generally known and have been described. In the relevant polynucleotides (e.g., expression vectors), the nucleic acid sequence encoding the HspA12B agonist or antagonist polypeptide (including an initiator methionine and optionally a targeting sequence) is operatively linked to a promoter or enhancer-promoter combination. Short amino acid sequences can act as signals to direct proteins to specific intracellular compartments. Such signal sequences are described in detail in U.S. Pat. No. 5,827,516, incorporated herein by reference in its entirety.

An ex vivo strategy can also be used for therapeutic applications. Ex vivo strategies involve transfecting or transducing cells obtained from the subject with a polynucleotide encoding an HspA12B agonist or antagonist compound. The transfected or transduced cells are then returned to the subject. Such cells act as a source of the HspA12B agonist or antagonist compound for as long as they survive in the subject.

The HspA12B agonist or antagonist compound for use in the present invention may also be modified in a way to form a chimeric molecule comprising HspA12B agonist or antagonist compound fused to another, heterologous polypeptide or amino acid sequence, such as an Fc sequence or an additional therapeutic molecule (e.g., a chemotherapeutic or cytotoxic agent).

The HspA12B agonist or antagonist compound can be packaged alone or in combination with other therapeutic compounds as a kit. Non-limiting examples include kits that contain, e.g., two pills, a pill, and a powder, a suppository and a liquid in a vial, two topical creams, etc.

The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Diagnostic Methods

The present invention features methods and compositions for the diagnosis of an angiogenic disorder or an endothelial cell disorder or the propensity to develop such a condition using HspA12B polypeptides, nucleic acid molecules, and antibodies. The methods and compositions can include the measurement of HspA12B polypeptides, either free or bound to another molecule, or any fragments or derivatives thereof. Alterations in HspA12B expression or biological activity in a test sample as compared to a normal reference can be used to diagnose any of the disorders of the invention.

A subject having an endothelial cell disorder or an angiogenic disorder, or a propensity to develop such a condition, will show an alteration (e.g., an increase or a decrease of 10%, 20%, 30%, 40%, 50%, 60%, 70%, 80%, 90%, or more) in the expression of a HspA12B polypeptide. For example, a decrease in the HspA12B polypeptide levels compared to a normal reference is diagnostic for endothelial cell disorders or a propensity to develop an endothelial cell disorder. An increase in the HspA12B polypeptide levels compared to a normal reference is diagnostic of an angiogenic disorder or a propensity to develop an angiogenic disorder. The HspA12B polypeptide can include full-length HspA12B polypeptide, degradation products, alternatively spliced isoforms of HspA12B polypeptide, enzymatic cleavage products of HspA12B polypeptide, and the like.

Standard methods may be used to measure levels of HspA12B polypeptide in any bodily fluid, including, but not limited to, urine, blood, serum, plasma, saliva, amniotic fluid, or cerebrospinal fluid. Such methods include immunoassay, ELISA, western blotting using antibodies directed to HspA12B polypeptide, and quantitative enzyme immunoassay techniques. ELISA assays are the preferred method for measuring levels of HspA12B polypeptide. In one example, an HspA12B binding protein, for example an antibody that specifically binds a HspA12B polypeptide, is used in an immunoassay for the detection of HspA12B and the diagnosis of any of the disorders described herein or the identification of a subject at risk of developing such disorders.

HspA12B nucleic acid molecules, or fragments or oligonucleotides of HspA12B that hybridize to HspA12B at high stringency may be used as a probe to monitor expression of HspA12B nucleic acid molecules in the diagnostic methods of the invention. Any of the HspA12B nucleic acid molecules above can also be used to identify subjects having a genetic variation, mutation, or polymorphism in a HspA12B nucleic acid molecule that are indicative of a predisposition to develop the conditions. These polymorphisms may affect HspA12B nucleic acid or polypeptide expression levels or biological activity. Detection of genetic variation, mutation, or polymorphism relative to a normal, reference sample can be used as a diagnostic indicator of a metastatic disease, or the propensity to develop such a condition.

Such genetic alterations may be present in the promoter sequence, an open reading frame, intronic sequence, or untranslated 3' region of a HspA12B gene. As noted throughout, specific alterations in the levels of biological activity of HspA12B can be correlated with the likelihood of an angiogenic disorder or an endothelial cell disorder, or the predisposition to the same. As a result, one skilled in the art, having detected a given mutation, can then assay one or more metrics of the biological activity of the protein to determine if the mutation causes or increases the likelihood of an angiogenic disorder or an endothelial cell disorder, or the predisposition to the same.

In one embodiment, a subject having an endothelial cell disorder, or the predisposition to the same, or a propensity to develop such a condition will show a decrease in the expression of a nucleic acid encoding HspA12B. In another embodiment, a subject having an angiogenic disorder, or a predisposition to the same, will show an increase in the expression of a nucleic acid encoding HspA12B. Methods for detecting such alterations are standard in the art and are described in Ausubel et al., supra. In one example Northern blotting or real-time PCR is used to detect HspA12B mRNA levels.

In another embodiment, hybridization at high stringency with PCR probes that are capable of detecting a HspA12B nucleic acid molecule, including genomic sequences, or closely related molecules, may be used to hybridize to a nucleic acid sequence derived from a subject having an endothelial cell disorder, an angiogenic disorder, or at risk of developing either disorder. The specificity of the probe, whether it is made from a highly specific region, e.g., the 5' regulatory region, or from a less specific region, e.g., a conserved motif, and the stringency of the hybridization or amplification (maximal, high, intermediate, or low), determine whether the probe hybridizes to a naturally occurring sequence, allelic variants, or other related sequences. Hybridization techniques may be used to identify mutations in an HspA12B nucleic acid molecule, or may be used to monitor expression levels of a gene encoding an HspA12B polypeptide (for example, by Northern analysis, Ausubel et al., supra).

Another method of detecting HspA12B useful in the diagnostic methods of the invention includes the detection of antibodies that specifically bind to HspA12B in the blood or serum of a subject. For such a diagnostic methods, an HspA12B polypeptide, or fragment thereof, is used to detect the presence of HspA12B antibodies in the blood or serum of a subject. The subject sample can be compared to a reference, preferably a normal reference and an increase in the level of anti-HspA12B antibodies present is indicative of an angiogenic disorder and a decrease in the level of anti-HspA12B antibodies present is indicative of an endothelial cell disorder.

Diagnostic methods can include measurement of absolute levels of HspA12B polypeptide, nucleic acid, or antibody, or relative levels of HspA12B polypeptide, nucleic acid, or antibody as compared to a reference sample. In one example, alterations in the levels of HspA12B polypeptide, nucleic acid, or antibody as compared to a normal reference, are considered a positive indicator of an angiogenic disorder, an endothelial cell disorder, or the propensity to develop such a disorder (an increase in the levels is indicative of an angiogenic disorder and a decrease in the levels relative to a normal reference is indicative of an endothelial cell disorder).

In any of the diagnostic methods, the level of HspA12B polypeptide, nucleic acid, or antibody, or any combination thereof, is measured at least two different times from the same subject and an alteration in the levels (e.g., by 10%, 20%, 30%, 40%, 50%, 60%, 70%, 80%, 90%, or more) over time is used as an indicator of an angiogenic disorder or an endothelial disorder, or the propensity to develop such a condition. It will be understood by the skilled artisan that for diagnostic methods that include the comparing of the HspA12B polypeptide, nucleic acid, or antibody level to a reference level, particularly a prior sample taken from the same subject, a change in time with respect to the baseline level can be used as a diagnostic indicator of an angiogenic disorder or an endothelial cell disorder, or a predisposition to either condition. The level of HspA12B polypeptide, nucleic acid, or antibody in the bodily fluids of a subject having a angiogenic disorder, or the propensity to develop such a condition may be altered, e.g., increased by as little as 10%, 20%, 30%, or 40%, or by as much as 50%, 60%, 70%, 80%, or 90% or more, relative to the level of HspA12B polypeptide, nucleic acid, or antibody in a prior sample or samples. The level of HspA12B polypeptide, nucleic acid, or antibody in the bodily fluids of a subject having an endothelial cell disorder, or the propensity to develop such a condition may be altered, e.g., decreased by as little as 10%, 20%, 30%, or 40%, or by as much as 50%, 60%, 70%, 80%, or 90% or more, relative to the level of HspA12B polypeptide, nucleic acid, or antibody in a prior sample or samples.

The diagnostic methods described herein can be used individually or in combination with any other diagnostic method described herein for a more accurate diagnosis of the presence of, severity of, or predisposition to an angiogenic disorder or an endothelial cell disorder.

Diagnostic Kits

The invention also provides for a diagnostic test kit. For example, a diagnostic test kit can include antibodies that specifically bind to HspA12B polypeptide, and components for detecting, and more preferably evaluating binding between the antibodies and the HspA12B polypeptide. In another example, the kit can include an HspA12B polypeptide or fragment thereof for the detection of HspA12B antibodies in the serum or blood of a subject sample. For detection, either the antibody or the HspA12B polypeptide is labeled, and either the antibody or the HspA12B polypeptide is substrate-bound, such that the HspA12B polypeptide-antibody interaction can be established by determining the amount of label attached to the substrate following binding between the antibody and the HspA12B polypeptide. A conventional ELISA is a common, art-known method for detecting antibody-substrate interaction and can be provided with the kit of the invention. HspA12B polypeptides can be detected in virtually any bodily fluid, such as urine, plasma, blood serum, semen, or cerebrospinal fluid. A kit that determines an alteration in the level of HspA12B polypeptide relative to a reference, such as the level present in a normal control, is useful as a diagnostic kit in the methods of the invention.

Desirably, the kit will contain instructions for the use of the kit. In one example, the kit contains instructions for the use of the kit for the diagnosis of an angiogenic disorder, or the propensity to develop an angiogenic disorder. In another example, the kit contains instructions for the diagnosis of endothelial cell disorder. In yet another example, the kit contains instructions for the use of the kit to monitor therapeutic treatment or dosage regimens.

The kit can also contain a standard curve indicating levels of HspA12B that fall within the normal range and levels that would be considered diagnostic of an endothelial cell disorder, an angiogenic disorder, or the propensity to develop any such disorder.

Subject Monitoring

The diagnostic methods described herein can also be used to monitor an endothelial disorder or an angiogenic disorder during therapy or to determine the dosages of therapeutic compounds. For example, alterations (e.g., a decrease as compared to the positive reference sample for an angiogenic disorder indicates an improvement in or the absence of an angiogenic disorder and an increase as compared to the positive reference sample for endothelial cell disorders indicates an improvement in or the absence of an endothelial cell disorder). In this embodiment, the levels of HspA12B polypeptide, nucleic acid, or antibodies are measured repeatedly as a method of not only diagnosing disease but also monitoring the treatment, prevention, or management of the disease. In order to monitor the progression of an angiogenic disorder or an endothelial cell disorder in a subject, subject samples are compared to reference samples taken early in the diagnosis of the disorder. Such monitoring may be useful, for example, in assessing the efficacy of a particular drug in a subject, determining dosages, or in assessing disease progression or status. For example, HspA12B levels can be monitored in a patient having an angiogenic disorder and as levels of HspA12B decrease, drug dosages may be decreased as well. HspA12B levels can also be monitored in a patient having an endothelial disorder and as levels of HspA12B increase, drug dosages may be decreased as well.

In addition, the diagnostic methods of the invention can be used to monitor a subject that has risk factors indicative of an angiogenic disorder or an endothelial disorder. For example a subject having a family history of an endothelial cell disorder or the early indications for such a disorder (e.g., increase in blood pressure or blood vessel thickening or blockage). In such an example, the therapeutic methods of the invention or those known in the art can then be used proactively to promote endothelial cell health and to prevent the disorder from developing or from developing further. In another example, a subject having a primary tumor can be treated with the therapeutic methods of the invention for angiogenic disorders to prevent metastasis of the tumor.

Screening Assays

As discussed above, we have discovered that HspA12B is an endothelial cell specific distant member of the HSP70 family of heat shock proteins that is critical for endothelial cell function and angiogenesis. Reductions in HspA12B levels or biological activity results in an inhibition of wound healing, endothelial cell migration, and tube formation; therefore, compounds that increase the levels or biological activity of HspA12B are useful for promoting endothelial cell health and for treating endothelial cell disorders. Conversely, increases in HspA12B levels or biological activity results in increased cell migration and angiogenesis; therefore, compounds that decrease the levels or biological activity of HspA12B are useful for treating angiogenic disorders. Based on these discoveries, HspA12B compositions of the invention are useful for the high-throughput low-cost screening of candidate compounds to identify those that modulate, or increase or decrease (e.g., by at least 10%, 20%, 30%, 40%, 50%, 60%, 70%, 80%, 90%, 95%, or more), the expression or biological activity of HSPA12B. Compounds that increase the expression or biological activity of HSPA12B can be used for the treatment of endothelial disorders or to promote vascular health. Compounds that decrease the expression or biological activity of HSPA12B can be used for the treatment of angiogenic disorders.

Any number of methods are available for carrying out screening assays to identify new candidate compounds that modulate (e.g., increase or decrease) the expression of an HspA12B polypeptide or nucleic acid molecule. In one working example, candidate compounds are added at varying concentrations to the culture medium of cultured cells expressing an HspA12B nucleic acid molecule. Gene expression is then measured, for example, by microarray analysis, Northern blot analysis (Ausubel et al., *Current Protocols in Molecular Biology*, Wiley Interscience, New York, 2001), or RT-PCR, using any appropriate fragment prepared from the HspA12B nucleic acid molecule as a hybridization probe. The level of gene expression in the presence of the candidate compound is compared to the level measured in a control culture medium lacking the candidate compound. A compound that promotes an increase or a decrease in the expression of an HspA12B gene or nucleic acid molecule, or a functional equivalent thereof, is considered useful in the invention. If the compound promotes an increase in the levels of the HspA12B gene or nucleic acid molecule; such a molecule may be used, for example, as a therapeutic to promote endothelial health in a subject. If the compound promotes a decrease in the levels of the HspA12B gene or nucleic acid molecule; such a molecule may be used, for example, as a therapeutic to treat an angiogenic disorder.

In another working example, an HspA12B nucleic acid molecule is expressed as a transcriptional or translational fusion with a detectable reporter, and expressed in an isolated cell (e.g., mammalian or insect cell) under the control of a heterologous promoter, such as an inducible promoter. The cell expressing the fusion molecule is then contacted with a candidate compound, and the expression of the detectable reporter in that cell is compared to the expression of the detectable reporter in an untreated control cell. A candidate compound that increases the expression of an HspA12B detectable reporter fusion is a compound that is useful as a therapeutic to promote endothelial health in a subject. A candidate compound that decreases the expression of an HspA12B detectable reporter fusion is a compound that is useful as a therapeutic to treat an angiogenic disorder in a subject.

In another working example, the effect of candidate compounds may be measured at the level of polypeptide expression using the same general approach and standard immunological techniques, such as Western blotting or immunoprecipitation with an antibody specific for an HspA12B polypeptide. For example, immunoassays may be used to detect or monitor the expression of HspA12B polypeptides in an organism. Polyclonal or monoclonal antibodies that are capable of binding to such a polypeptide may be used in any standard immunoassay format (e.g., ELISA, Western blot, or RIA assay) to measure the level of the polypeptide. In some embodiments, a compound that promotes an alteration, such as an increase or a decrease, in the expression or biological activity of an HspA12B polypeptide is considered particularly useful. Again, a candidate compound that increases the expression level or biological activity of an HspA12B polypeptide is a compound that is useful as a therapeutic to promote endothelial health in a subject. A candidate compound that decreases the expression level or biological activity of an HspA12B polypeptide is a compound that is useful as a therapeutic to treat an angiogenic disorder in a subject.

In yet another working example, candidate compounds may be screened to identify those that specifically bind to an HspA12B polypeptide, preferably one that specifically binds to the ATPase domain or the substrate-binding domain. The efficacy of such a candidate compound is dependent upon its ability to interact with such a polypeptide or a functional equivalent thereof. Such an interaction can be readily assayed using any number of standard binding techniques and functional assays (e.g., those described in Ausubel et al., supra). In one embodiment, a candidate compound may be tested in vitro for its ability to specifically bind to an HspA12B polypeptide. Compounds that specifically bind to HspA12B and preferably act as an antagonist toHspA12B can be used for the treatment of an angiogenic disorder.

In one particular working example, a candidate compound that binds to an HspA12B polypeptide may be identified using a chromatography-based technique. For example, a recombinant HspA12B may be purified by standard techniques from cells engineered to express HspA12B and may be immobilized on a column. A solution of candidate compounds is then passed through the column, and a compound specific for the HspA12B polypeptide is identified on the basis of its ability to bind to the polypeptide and be immobilized on the column. To isolate the compound, the column is washed to remove non-specifically bound molecules, and the compound of interest is then released from the column and collected. Similar methods may be used to isolate a compound bound to a polypeptide microarray. Compounds isolated by this method (or any other appropriate method) may, if desired, be further purified (e.g., by high performance liquid chromatography). In addition, these candidate compounds may be tested for their ability to function as an antagonist to the HspA12B polypeptide. Compounds isolated by this approach may also be used, for example, as therapeutics to treat or prevent an angiogenic disorder in a subject. Compounds that are identified as binding to HspA12B with an affinity constant less than or equal to 10 mM are considered particularly useful in the invention. Alternatively, any in vivo protein interaction detection system, for example, any two-hybrid assay may be utilized to identify compounds or proteins that bind to an HspA12B polypeptide of the invention.

Identification of New Compounds or Extracts

In general, compounds capable of increasing or decreasing the activity of HSPA12B are identified from large libraries of both natural product or synthetic (or semi-synthetic) extracts or chemical libraries or from polypeptide or nucleic acid libraries, according to methods known in the art. Those skilled in the field of drug discovery and development will understand that the precise source of test extracts or compounds is not critical to the screening procedure(s) of the invention. Compounds used in screens may include known compounds (for example, known therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their molt-disrupting activity should be employed whenever possible.

When a crude extract is found to increase or decrease the biological activity or expression levels of an HSPA12B polypeptide, or to bind to an HSPA12B polypeptide, further fractionation of the positive lead extract is necessary to isolate chemical constituents responsible for the observed effect. Thus, the goal of the extraction, fractionation, and purification process is the careful characterization and identification of a chemical entity within the crude extract that decreases the biological activity of an HSPA12B polypeptide. Methods of fractionation and purification of such heterogeneous extracts are known in the art. If desired, compounds shown to be useful as therapeutics for the treatment or prevention of an endothelial cell disorder or an angiogenic disorder are chemically modified according to methods known in the art.

EXAMPLES

We sought to discover novel genes of functional importance in early vessel formation by a two-step process: (A) the screening of 4000 transcripts from a zebrafish kidney/bone marrow cDNA library (Galloway et al., *Dev. Cell* 8:109-116 (2005)) to identify those whose expression was relatively restricted to developing vessels in the 24-72 hpf period, and (B) the use of antisense morpholino oligonucleotides mediated knockdown in embryos to assess a vascular phenotype. Of the approximately 50 transcripts from the library whose expression was localized mainly to vasculature during early development, we focused attention on one designated as GA2692, which at the time these studies were initiated, had homology to the human cDNA FLJ32150, of which nothing was known in terms of expression or function. More recently, FLJ32150 was found to be identical to HspA12B, a transcript present in macrophages in atherosclerotic lesions (Han et al., *Proc. Natl. Acad. Sci. USA* 100:1256-1261 (2003)), but the relevance of the expression and the function of the protein in endothelial biology was unknown and unsuspected. HspA12B is believed to be a distantly related member of the Hsp70 family but one containing an atypical ATPase domain and a distinctive substrate binding domain located in its C-terminus.

Hsp70s constitute one group of the heat shock protein superfamily, classified according to their molecular weight: Hsp10, small Hsps, Hsp40, Hsp60, Hsp70, Hsp90 and Hsp110 (Kiang and Tsokos, *Pharmacol. Ther.* 80:183-201 (1998); Snoeckx et al., *Physiol. Rev.* 81:1461-1497 (2001)). As molecular chaperones, mammalian Hsp70s associate with unfolded nascent precursor peptides to stabilize them prior to their folding into mature proteins and reaching their ultimate cellular compartments (Artigues et al., *J. Biol. Chem.* 272: 16852-16861 (1997); Beckmann et al., *Science* 248:850-854 (1990); Hartl et al., *Annu. Rev. Biophys. Biomol. Struct.* 21:293-322 (1992)). Hsp70s can also aid in solubilizing and refolding damaged proteins or transporting them to degradative organelles. Hsp70s are capable of protecting cells, tissues, organs, and animals from various noxious conditions (Kiang et al., *Pharmacol. Ther.* 80:183-201 (1998); Marber et al., *J. Clin. Invest.* 95:1446-1456 (1995); Plumier et al., *J. Clin. Invest.* 95:1854-1860 (1995); Polla et al., *Am. J. Physiol.* 252:C640-C649 (1987); Ribeiro et al., *Crit. Care Med.* 22:922-929 (1994); Samali and Cotter, *Exp. Cell Res.* 223: 163-170 (1996); Takano et al., Cell Stress Chaperones. 3:109-117 (1998)).

Here we characterize the zebrafish GA2692 transcript and its presumed mammalian orthologue HspA12B and show their selective expression in vasculature in zebrafish and in endothelial cells (ECs) in vitro. Then, using antisense morpholino oligos and small interfering RNA (siRNA) methodologies, we demonstrate that GA2692/HspA12B (which for simplicity will henceforth be designated just as HspA12B) is essential for zebrafish vascular development and for endothelial cell migration, wound healing and tube formation in vitro.

Experimental Procedures

The following experimental procedures were used for the assays described below.

Isolation of cDNA Clone

GA2692 was identified by an whole-mount in situ hybridization (WMISH) screen (Galloway et al., supra) and was isolated from an adult zebrafish kidney cDNA library (Dr. J. Rast, Children's Hospital, St. Petersburg, Fla.).

Zebrafish Lines and Maintenance

Adult zebrafish were maintained as described (Westerfield, The zebrafish book. A guide for the laboratory use of zebrafish (*Danio rerio*). Eugene, Oreg.: Univ. of Oregon Press. (2000)). Developmental stages were determined by embryo morphology and hpf (Kimmel et al., Dev. Dyn. 203: 253-310 (1995)). Embryo medium was supplemented with 0.003% 1-phenyl-2-thiourea (Sigma) before 24 hpf to prevent melanin formation.

Whole-Mount In Situ Hybridization

Whole-mount in situ hybridization was carried out as described (Jowett and Lettice, *Trends. Genet.* 10:73-74 (1994); Thisse et al., *Methods Cell Biol.* 77:505-519 (2004)). For histological analysis, specimens were fixed in 4% paraformaldehyde overnight at 4° C., dehydrated with ethanol, and embedded in JB-4™ resin (Polysciences, Inc., Warrington, Pa.). Specimens were sectioned at 6 μm using a Jung Supercut 2065 microtome and examined with a Nikon Optiphot 2 Microscope.

Antisense Morpholino Oligonucleotides: Sequence and Injection

Morpholino antisense oligos were designed and synthesized by Gene Tools LLC., Philomath, Oreg. The sequences are, 5'-ATATTACAGGACTTTCACAGCCCGA-3' (SEQ ID NO: 6) (MOATG, targeting six bases upstream of the ATG start site), 5'-ATTTTAGAGGAGTTTCACACCCGGA-3' (SEQ ID NO: 7) (MM, the corresponding mispairing control for MOATG, the five mismatched bases are underlined) and 5'-ACAGACATAAATACCTCATCATGTG-3' (SEQ ID NO: 8) (MOs3rd, MO targeting the third exon-intron junction to block the splicing of mRNA precursor). Solutions were prepared and injected as described (Nasevicius and Ekker, 2000) using a gas driven microinjector (Pico-Injector, PL1-90, Harvard Apparatus).

In Vitro Transcription and Translation

The TNT® Quick Coupled Reticulocyte Lysate system (Promega) was used according to the manufacturer's protocol with modifications. In a 12.5 μl reaction, 0.25 μg of pBK-CMV-HspA12B and different concentrations of MOATG and MM (0, 10 nM, 1 μM and 10 μM final concentration) were added to the TNT® Master Mix, containing all of the required components for in vitro transcription and translation plus $^{35}$S-labeled methionine, and incubated at 30° C. for 90 minutes. $S^{35}$-labeled proteins were visualized by autoradiography following resolution by 4-15% SDS-PAGE.

Reverse Transcription-PCR of HspA12B Fragments from Zebrafish Embryos

Following collection of embryos 48 hours after injection of various concentrations of MOs, total RNA was extracted using RNeasy™ Mini Kit (Qiagen). Reverse transcription was performed according to SuperScript™ III First-Strand Synthesis System for RT-PCR using oligo dT primer (Invitrogen). PCR was carried out using Platinum® Taq DNA Polymerase (Invitrogen). Forward and reverse primers are 5'-GCTGTGAAAGTCCTGTAATA-3' (SEQ ID NO: 9) and 5'-AAAGTATAGCCAATGTCTGG-3' (SEQ ID NO: 10), respectively.

Endogenous Alkaline Phosphatase (AP) Staining

Whole-mount AP staining was carried out essentially according to a published protocol (Habeck et al., Curr. Biol. 12:1405-1412 (2002)).

Microangiography

Microangiography was performed as described (Weinstein et al., Nat. Med. 1:1143-1147 (1995)) except that 0.02 µm Fluorospheres® with red fluorescence (Invitrogen) in 1% bovine serum albumin (BSA) were injected into the fish.

Time Lapse Analysis

Time lapse analysis movies were made as described (Bedell et al., Proc. Natl. Acad. Sci. USA 102:6373-6378 (2005)) except that Tg(fli1:EGFP)$^{y1}$ embryos were used.

Northern Blot Analysis

Total RNA was extracted from different cell lines using RNeasy™ mini kit (Qiagen). Ten µg of RNA was subjected to northern blotting. The full length human HspA12B coding region was PCR amplified (Advantage™ GC cDNA PCR kit from Clontech) from a human umbilical vein endothelial cell (HUVEC) reverse transcription product using primers: 5'-ACAGGATCCACCATGTTGGCTGTCCCGGAGATG-3' (SEQ ID NO: 11) and 5'-TCAGTTGGAAAGAAAGTCGATGGA-3' (SEQ ID NO: 12) and used as a probe after purification. A $^{32}$P-labelled probe was generated using Prime-It® II random primer labeling kit (Stratagene). It was added to ExpressHyb™ Rapid Hybridization Buffer (Clontech) and the blot was incubated for 3-4 hours at 65° C. and then washed and autoradiographed.

Real time PCR Analysis

Specific sets of primers and Taqman® probes were designed by using PRIMER EXPRESS (Applied Biosystems) and synthesized by GenScript, Piscataway, N.J. The primer and probe sequences for human HspA12B were 5'-CTTCTTCAGGGAGCACGCC-3' (SEQ ID NO: 13), 5'-TGTCCTTCTCTGGCAGCGA-3' (SEQ ID NO: 14) and FAM-5'-TCAGGAGCTGAGGGAGCAGAGCCC-3'-TAMRA (SEQ ID NO: 15). The sequences for HspA12A (another gene highly homologous to HspA12B) were 5'-CAGGAATAACGCCTCTGTCC-3' (SEQ ID NO: 16), 5'-CACCACGAGAAATGACTGCT-3' (SEQ ID NO: 17) and FAM-5'-CCCTCCCATATTGTAACGACACTGA-3'-TAMRA (SEQ ID NO: 18). Human glyceraldehyde-3-phosphate dehydrogenase (GADPH) primers (Applied Biosystems) were included in all reactions as an endogenous control. The Real time PCR reactions were performed on an Applied Biosystems 7500 Real-time PCR System using Taqman® One-step RT-PCR master mix (Applied Biosystems). All data were analyzed by ΔΔCt using the 7500 system SDS software (Applied Biosystems).

Polyclonal Antibody Against HspA12B

An anti-HspA12B polyclonal antibody, AB4112, was generated by immunizing rabbits with a synthesized peptide derived from mouse HspA12B with the following amino acid sequence, CVDVSTNRSVRAAIDFLSN (SEQ ID NO: 19). Detailed generation, purification and validation of this antibody will be described elsewhere (Steagall et al., Arterioscler. Thromb. Vasc. Biol. (2006) e-publication ahead of print).

Plasmid Construction, Adenovirus Amplification and HUVEC Infection

Full length human HspA12B cDNA with a FLAG® tag was amplified using Advantage™ GC cDNA PCR kit (Clontech) from a HUVEC reverse transcription product using forward primer 5'-ACAGGATCCACCATGTTGGCTGTCCCGGAGATG-3' (SEQ ID NO: 20) and reverse primer 5'AAACTCGAGTCACTTATCGTCGTCATCCTTGTAATCGTTGGAAAGA AAGTCGATGGA-3' (SEQ ID NO: 21). The PCR product was digested with BamHI and Xho I and ligated into the pCS2+ expression vector, designated as pCS2+-S8 and confirmed by sequencing. The gene was further subcloned into the pShuttle-CMV vector by BamHI and Xba I digestion. Adenoviral recombinants were obtained using BJ 5183 AD-1 electrocompetent cells (Stratagene). Adenoviruses were amplified using QBI-HEK293A cells (QBiogene, Morgan Irvine, Calif.). Amplification, CsCl purification and virus storage were done as described (He et al., Proc. Natl. Acad. Sci. 95:2509-2514 (1998)) and viral titers were determined using Adeno-X™ Rapid Titer Kit (BD Biosciences). HUVECs (Cascade Biologics, Inc. Portland, Oreg.) cultured in 6-well tissue culture plates to 60% confluency were infected with adenoviruses for 6 hours at which point fresh EGM2™-MV medium (Cambrex) was added and cells were incubated for 24-48 hours prior to further experiments.

The constitutively active adenoviral Akt construct was a gift of Dr. Kenneth Walsh (Boston University) (Fujio and Walsh, J. Biol. Chem. 274:16349-16354 (1999)), which contains the c-src myristoylation sequence fused in-frame to the N terminus of the HA-Akt (wild-type) coding sequence that targets the fusion protein to the membrane. Virus amplification and purification were done as above.

siRNIAs and Transfection

All siRNAs (sequences shown below) against human HspA12B were obtained from Dharmacon. Silencer® Negative Control #1 siRNA (NC) was obtained from Ambion, Inc. Lipofectamine™ 2000 (Invitrogen) was used to transfect siRNAs into HEK 293 cells (final concentration 62.5 nM) in 6-well plates and HUVECs cultured in 6-well plates or 10 cm plates as suggested in the manual.

The sense sequences of the siRNAs are: siGENOME™ duplex 1 (si1), CCACGGAUCUCACCUUGAAUU (SEQ ID NO: 22); siGENOM™ duplex 2 (si2), CGACUUUCUUUCCAACUGAUU (SEQ ID NO: 23); siGENOME™ duplex 3 (si3), GGGACUGGCUCUACUUCGAUU (SEQ ID NO: 24); siGENOME™ duplex 4 (si4), CCAGCUAGAGGCAGUAAAUUU (SEQ ID NO: 25).

Western Blot Analysis

Protein lysates were collected from HUVECs or HEK293 cells using RIPA buffer with protease inhibitor cocktail complete Mini tablets (Roche). For protein phosphorylation studies, additional phosphatase inhibitor cocktail 1 &2 from Sigma Aldrich was added to the RIPA buffer. HUVECs were serum starved in 0.5% serum EBM-2 (Cambrex) for 24 hours before stimulation with VEGF (10 ng/ml) in 0.5% serum EBM-2 or EGM™-2 MV. Protein concentration was measured using BCA protein assay reagents from PIERCE. Proteins were loaded onto Novex® 4-12% Bis-Tris gel or 3-8% Tris-Acetate gel (Invitrogen) and transferred onto an Immobilon-P PVDF Transfer membrane (Millipore). Akt (pS473) rabbit monoclonal antibody was obtained from Abcam; total Akt1/2 rabbit polyclonal IgG was from Santa Cruz Biotechnology; monoclonal antibody against GAPDH was obtained from Chemicon International. The horseradish peroxidase-coupled secondary antibodies were from GE Healthcare and SuperSignal™ chemiluminescent substrates (Pierce) were used for visualization.

Migration and Wound Healing Assays

Migration assay was done as previously described (Seth et al., *Biochem. Biophys. Res. Comm.* 332:533-541 (2005)). HUVECs infected with adenovirus or transfected with siRNAs were grown in 6-well tissue culture plates and a wound of defined size was made in the confluent cell monolayer with a pipette tip. Phase contrast micrographs were used to assess wound closure at 0, 16 and 60 hours.

Tube Formation Assay

The tube formation assay and quantification was performed as previously described (Merchan et al., *J. Natl. Cancer Inst.* 95:388-399 (2003)).

Example 1

Zebrafish GA2692 cDNA Sequence and Homology to Mammalian HspA12B

A clone designated GA2692 was one of the roughly 50 clones—from a total of approximately 4000 cDNAs screened by whole-mount in situ hybridization in zebrafish—that showed expression largely restricted to developing vessels.

The sequence of the GA2692 cDNA consisted of 2884 nucleotides (GenBank accession number, DQ119052). The longest open reading frame extended from nucleotides 267 to 2339 and predicted a protein with 691 amino acid residues (FIG. 11B). When this protein sequence was initially "blasted" to the zebrafish and mammalian genome (approximate date October 2002), GA2692 showed homology to a human EST dubbed FLJ32150. Subsequent blast searches in year 2003 showed that the mouse and human HspA12B demonstrated a 70% identity to GA2692, that human HspA12B and FLJ32150 were identical in their overlap regions and that GA2692 had a 30% identity to HspA12A (FIGS. 11B, 11C). A phylogenetic tree analysis also indicated that GA2692 evolved from the same ancestor as HspA12Bs in other species (FIG. 11D). It is likely therefore that HspA12B is the mammalian orthologue of zebrafish GA2692. In added support of this relationship is the restricted expression of HspA12B to cultured endothelial cells (see below).

Example 2

Expression of HspA12B During Embryonic Development of Zebrafish

A detailed characterization of HspA12B was carried out at different developmental stages. No expression of HspA12B was found before 10 somite stage. During the middle of somitogenesis (12-16 somite stage), expression was observed in ventral hematopoietic and vasculogenic mesoderm in both posterior and cephalic territories (FIGS. 1A-D). Weaker expression was also observed in anterior telencephalon, diencephalon and hindbrain rhombomeres likely in the ventral part of rhombomeres 3 and 5 (FIG. 1E), the first somite (FIG. 1F) as well as in the anterior part of the otic vesicle (FIG. 1G).

Figure 1:
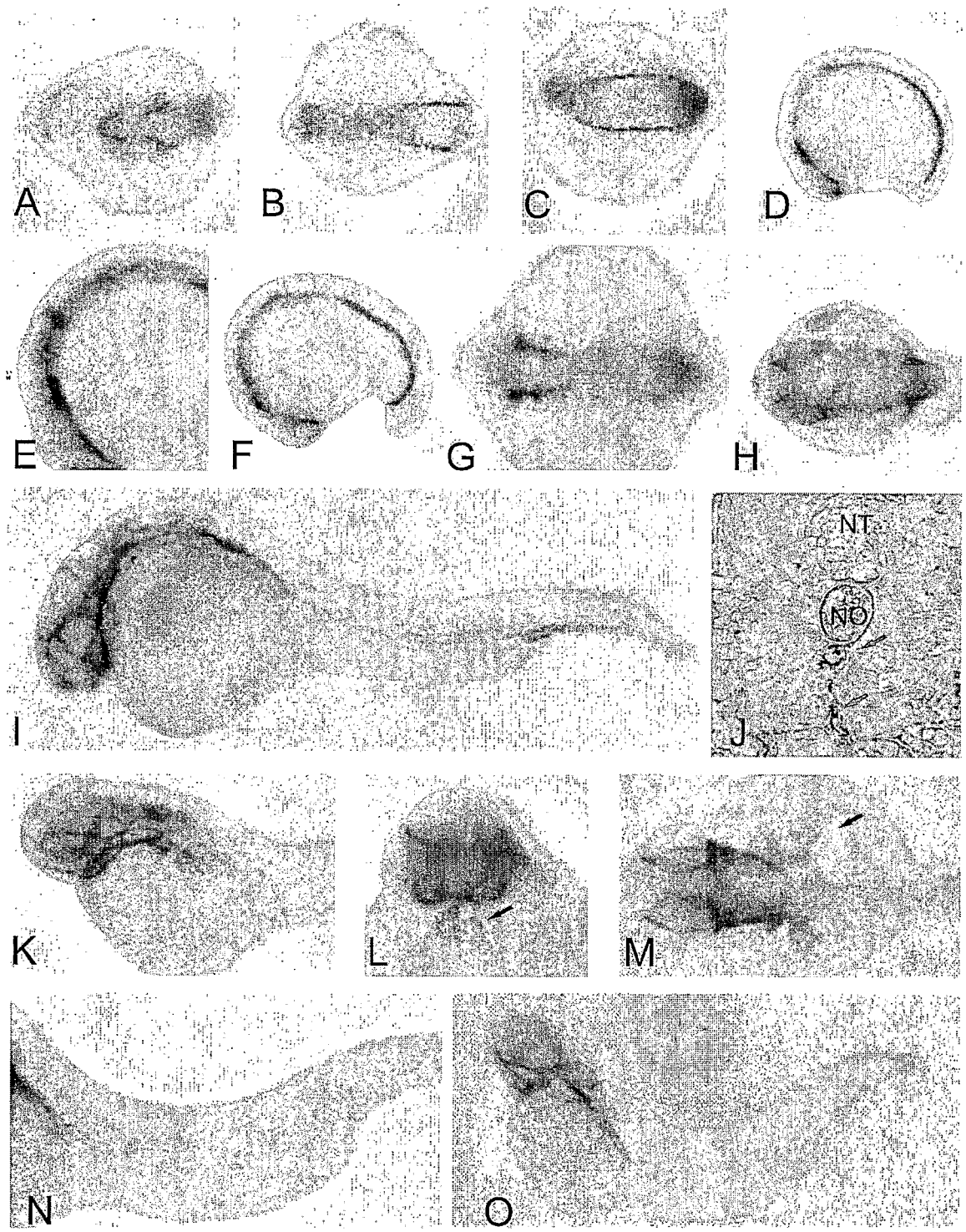

At 24 hpf, expression of HspA12B was mostly observed in vasculature (such as head, aorta, caudal vein, posterior cardinal vein and intersegmental blood vessels) (FIGS. 1H, I, J). Expression could also be found in telencephalon, anterior diencephalon, head mesenchyme, choroid fissure and heart (FIGS. 1H, I).

At 36 hpf, expression was observed in head vasculature (FIG. 1K), heart (FIG. 1L, arrow head), duct of Cuvier (FIG. 1M, arrow head), axial vasculature, intersegmental blood vessels (FIG. 1N), head mesenchyme (mainly around the eye and the otic vesicle) (FIGS. 1K, L, M) and branchial arches (FIG. 1K). At 48 hpf, expression was restricted to splanchnocranium (otic placode, trabecula cranii, lower jaw). Expression decreased after 48 hpf.

Example 3

Knockdown of HspA12B by MOs

Figure 2:
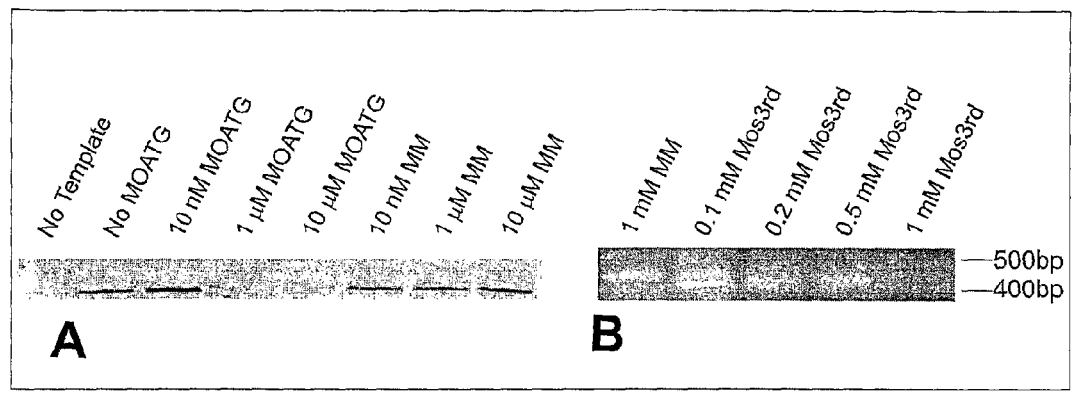
FIGS. 2A-2F are a series of images showing the knockdown of HSPA12B by morpholino oligomers during zebrafish development.
Figure 2:
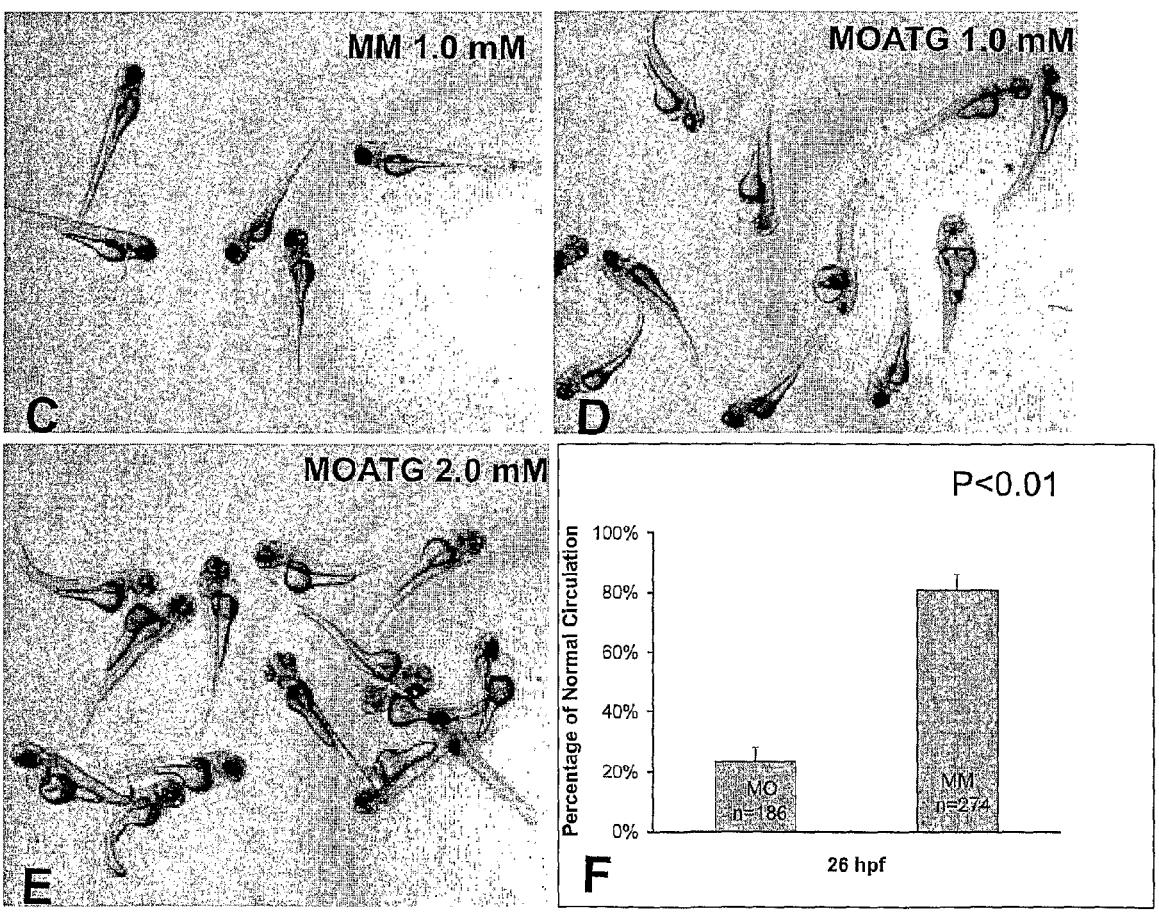

Since the MOATG sequence was derived against a region six bases before the start codon, we expected that it would serve as a translation blocker. We therefore tested the potency and specificity of the HspA12B MOATG in an in vitro transcription and translation system. The HspA12B MOATG inhibited protein translation in a dose-dependent manner (FIG. 2A). On the other hand, no inhibiting effect from the MM was observed even at 10 µM.

The knockdown of HspA12B by MOs3rd was also confirmed by RT-PCR (FIG. 2B). RNAs were extracted from zebrafish embryos injected with various amount of MOs. The alternative splicing of mRNA caused by MOs3rd was verified by RT-PCR. Results showed that almost all mRNA was alternatively spliced after injection of 0.2 mM MOs3rd. Further increasing of concentration can even reduce the total mRNA level.

Example 4

Knockdown of HspA12B Causes Vascular Developmental Defects in Zebrafish

Zebrafish embryos were microinjected with HspA12B MOATG, MOs3rd, and MM at the 1-4 cell stage and examined for vascular defects at 24, 48 and 72 hpf. At different stages, embryos injected with MM had normal blood cell circulation in the axial (dorsal aorta and posterior cardinal vein) vessels, the intersegmental vessels (ISVs), the dorsal longitudinal anastomotic vessels (DLAVs), the subintestinal vessels (SIVs) and the pectoral fin vessels. However, the majority of MOATG and MOs3rd injected embryos exhibited slower trunk circulation and severely compromised circulation through the ISVs. The phenotype became more obvious as the concentration of MOATG and MOs3rd was increased. Embryos injected with MOATG and MOs3rd exhibited very similar phenotypes, although a higher dose was required for MOATG to show the same potency as MOs3rd. Table 1 shows the dose response of the circulation defects noted for MOATG (examined at 48 hpf): 4.3% of embryos presented circulation defects in 0.5 mM MOATG injected fish vs. 41.5% and 60% in 1.0 mM and 2.0 mM MOATG injected fish respectively.

TABLE 1

Live observation in MOATG injected fish.

|  | WT | 0.5 mM MO | 1.0 mM MO | 2.0 mM MO |
| --- | --- | --- | --- | --- |
| Embryos injected | 42 | 47 | 41 | 35 |
| Slow circulation | 0 (0%) | 2 (4.3%) | 11 (26.8%) | 12 (34.3%) |
| No circulation | 0 (0%) | 0 (0%) | 6 (14.6%) | 9 (25.7%) |
| Total circulation defect | 0 (0%) | 2 (4.3%) | 17 (41.5%) | 21 (60%) |

As the MOATG and MOs3rd concentration was increased, the following phenotypes were also noted (FIGS. 2C, D, E). 1) The total body length decreased. 2) The lumen of axial vessels including the dorsal aorta and axial vein was narrowed and short-circuiting of blood flow could be observed. 3) Flow in the ISVs, SIVs and the vascular arch of the fin bud was disrupted. 4) Blood cells accumulated in the tail vein plexus and/or common cardinal vein. 5) Pericardial edema was noted in most fish FIGS. 2D, E).

Example 5

Figure 3:
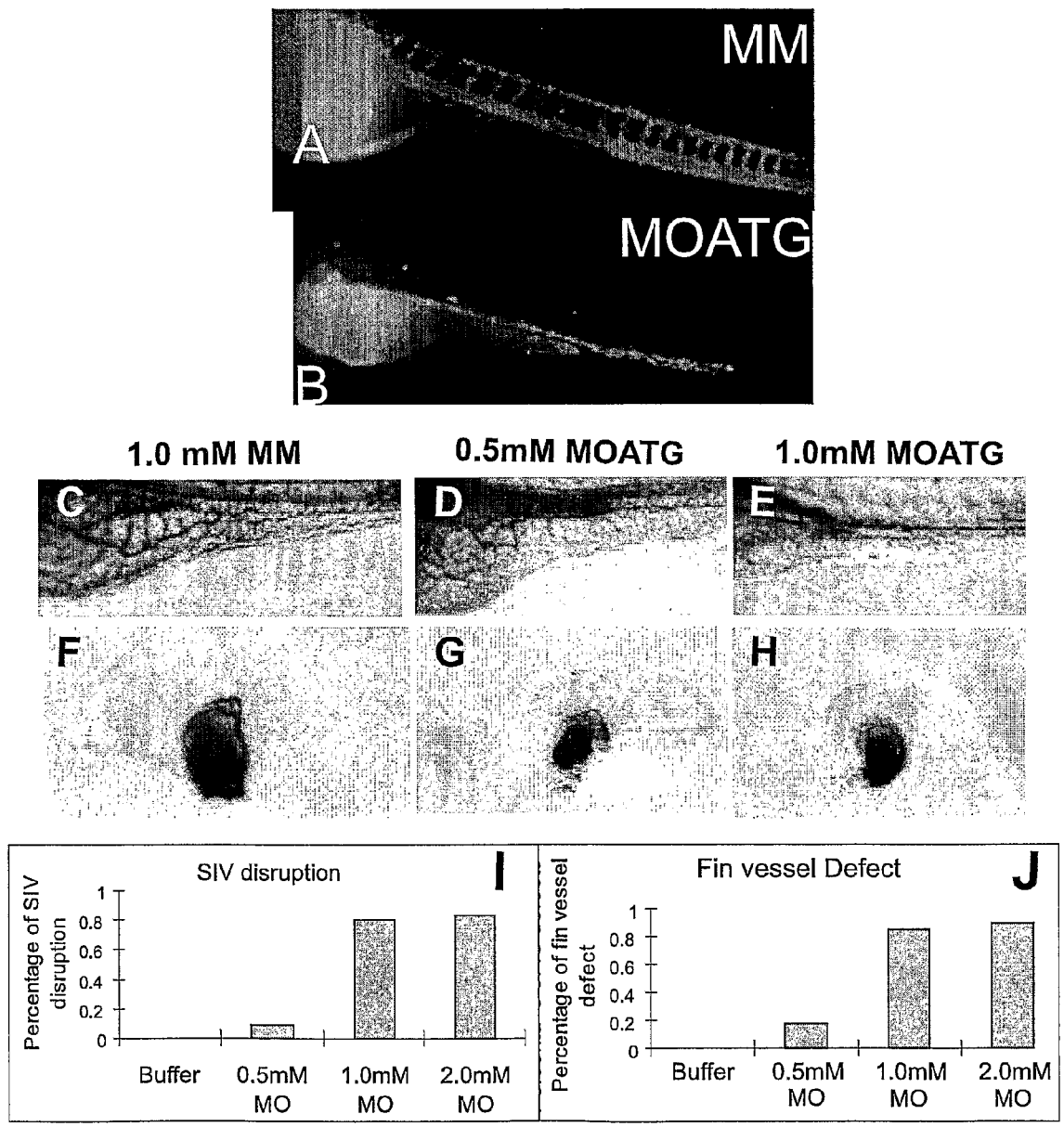
FIGS. 3A-3J show phenotypes in morphants defined by microangiography and AP staining.

Microangiography and AP Staining Further Demonstrate Vascular Defects in HspA12B Morphants To further investigate the vascular phenotypes in HspA12B morphants, we used microangiography with 0.02 μm fluorospheres and did AP staining (which only stains endothelial cells) on MOATG- and MM-injected fish. Microangiography clearly demonstrated absence of circulation in ISVs in morphants and narrowed trunk vessels compared with controls (FIGS. 3 A, B). At 72 hpf, AP staining showed that SIVs and fin vessels also had defects to varying degrees depending on the concentration of MOATG injected, whereas there were no observable vessel defects in MM-injected fish. As the concentration of MOATG was increased, the defects in these two vessels increased (FIGS. 3C-H). In the 0.5 mM group, the percentages with defects of SIV and fin vessel were 8.89% and 17.78%, respectively (FIGS. 3 I, J). In the group of 1.0 mM MOATG, percentages of defects of SIV and fin vessel were 80% and 85%, respectively. In the group of 2.0 mM MOATG, percentages of defects of SIV and fin vessel were 82.76% and 89.66%, respectively.

Example 6

Knockdown of HspA12B in [Tg(fli1:EGFP)$^{y1}$] Zebrafish Line Disrupts the Angiogenic Formation of ISVs and DLAVs These results pointed to multiple vascular defects in the HspA12B morphants. Next, to assess whether the defects seen could be ascribed to the absence of endothelial cells in the HspA12B morphants, we carried out the knockdown experiments in the [Tg(fli1:EGFP)$^{y1}$] zebrafish line, in which virtually all ECs and their angioblast precursors are highlighted by the robust expression of EGFP driven by a 15 kb fli-1 promoter (Isogai et al., *Development* 130:5281-5290 (2003)), (Lawson and Weinstein, *Dev. Biol.* 248:307-318 (2002)). The use of these fish allowed us to monitor vascular development in real time by fluorescent microscopy.

Figure 4:
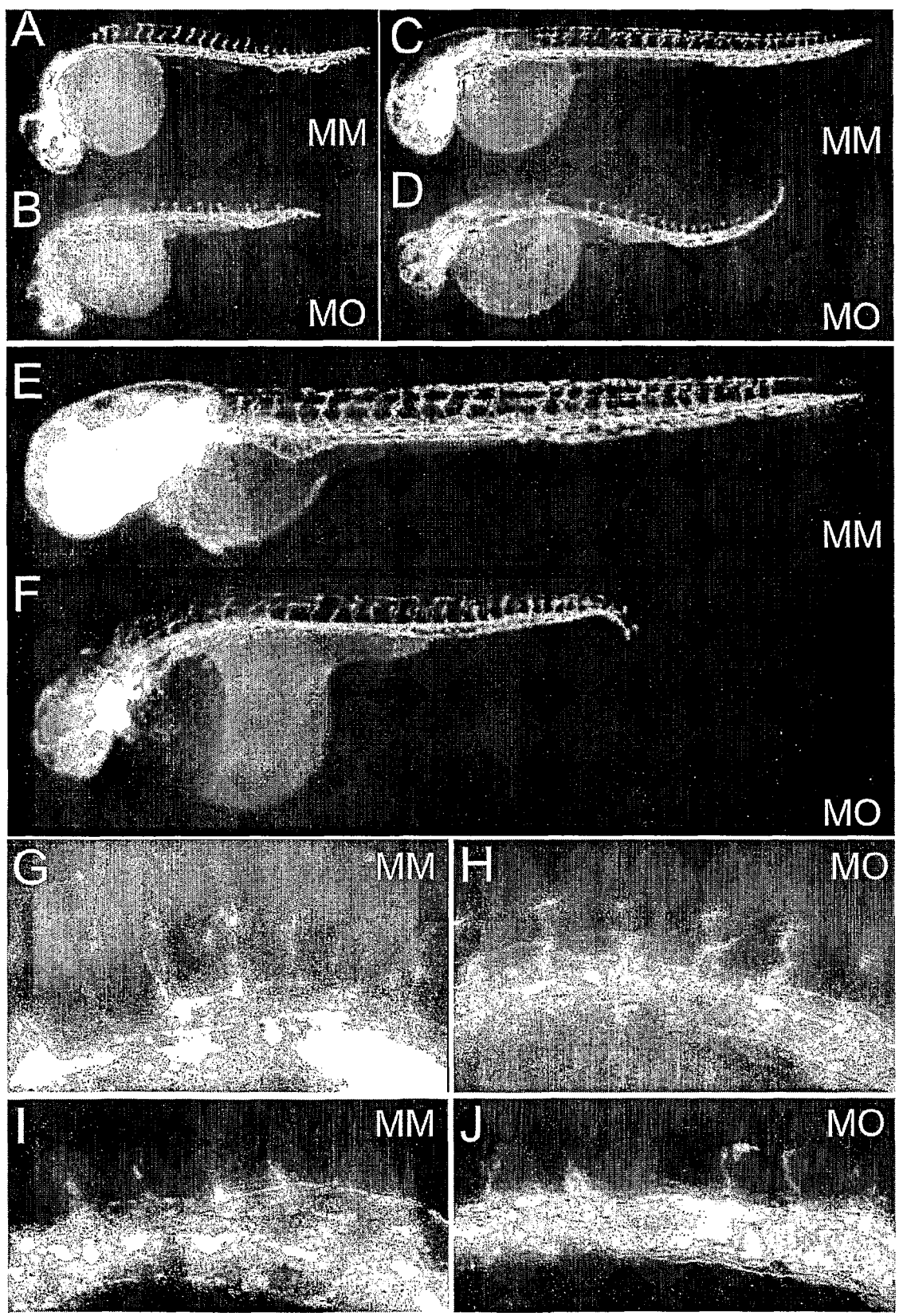
FIGS. 4A-4J show the impaired angiogenic processes revealed by knockdown of HspA12B in the [Tg(fli1:EGFP)$^{y1}$] zebrafish line.

After injecting MOsATG, early vasculogenesis, the de novo formation of major trunk vessels by co-migration and coalescence of angioblast progenitor cells originating in the trunk lateral mesoderm (Risau and Flamme, *Ann. Rev. Cell Dev. Biol.* 11:73-91 (1995)), was largely unaffected in the morphants in comparison with wild type fish. However, the formation of ISVs and DLAVs, an angiogenic process involving the sprouting and migration of ECs from the axial vessels, was disrupted in the HspA12B morphants. At 27 hpf, the EC sprouts appeared sporadically along the longitude of the HspA12B morphants, in contrast to their blossoming in the control embryos (FIGS. 4A, B). At 36 hpf, an elaborate network of ISVs and DLAVs was clearly visible in control embryos, while the dorsal part of this network was completely absent in the morphants, even 14 hours after the initial sprouting (FIGS. 4C, D). Therefore, this difference is unlikely to merely represent a delay in an otherwise largely normal developmental program. At 54 hpf, a small percentage of these ECs remained exactly where they were at 36 hpf; some ECs branched horizontally at the midline and connected to each other; others did sprout dorsally during this time period but followed distorted paths resulting in fragmentary DLAVs (FIGS. 4E, F). This was observed in 85.7% of embryos injected with MOATG. These ISVs and DLAVs were not functional as previously demonstrated by microangiography (FIGS. 3A, B) and visualization of the circulation. Furthermore, parachordal endothelial cells sprouts were dramatically reduced in most zebrafish embryos injected with MOATG or MOs3rd (Table 2). Table 2 shows the effects of MOs on the reduction of the dorsal part of ISVs, parachordal endothelial cell sprouts and DLAVs in the [Tg(fli1:EGFP$^{f^{y1}}$] zebrafish line at 48 hpf using fluorescent microscope. Data is presented as a percentage of affected embryos in total embryos examined.

TABLE 2

| Effects of MOs. | | | | |
|---|---|---|---|---|
| | 0.1 mM MOs3rd | 0.2 mM MOs3rd | 1 mM MOATG | 1 mM MM |
| ISVs | 0 | 0 | 71.4 | 14.3 |
| DLAVs | 0 | 35.3 | 85.7 | 14.3 |
| Parachordal sprouts | 4.2 | 64.3 | 85.7 | 14.3 |

To examine more closely the ISV sprouting from DA, we used live time-lapse analysis to track the sprouting endothelial cells during formation of the primary ISV network. In MM injected embryos, most ISVs extended slightly rostrally and then caudally after crossing the transverse myoseptum, potentially following the chevron like contours of the somites, before reaching the dorso-lateral surface, where tubes from adjacent ISVs fused to form the DLAVs. Movies from MOATG injected embryos showed that the axial vessels did extend rostrally but then made a sharp caudal turn. In fact, most ISVs formed preliminary T-shape structure prior to reaching the dorso-lateral surface when compared to age-matched MM injected embryos (FIGS. 4G, H). Moreover, the rostral-caudal coordinated timing of ISVs sprouts was disturbed in the MOATG injected embryos (FIGS. 4I, J). Taken together, the time lapse results and the spectrum of ISV defects in other assays suggested that in general, reduced HspA12B level in endothelial cells might render them incompetent to respond spatially and temporally to cues from the surrounding environment.

The specific expression of HspA12B in vasculature and its importance in angiogenesis during zebrafish early development prompted us to investigate the function of its human orthologue. We began by first assessing HspA12B expression levels in multiple cell lines.

Example 7

Human HspA12B is Specifically Expressed in Endothelial Cells

Figure 5:
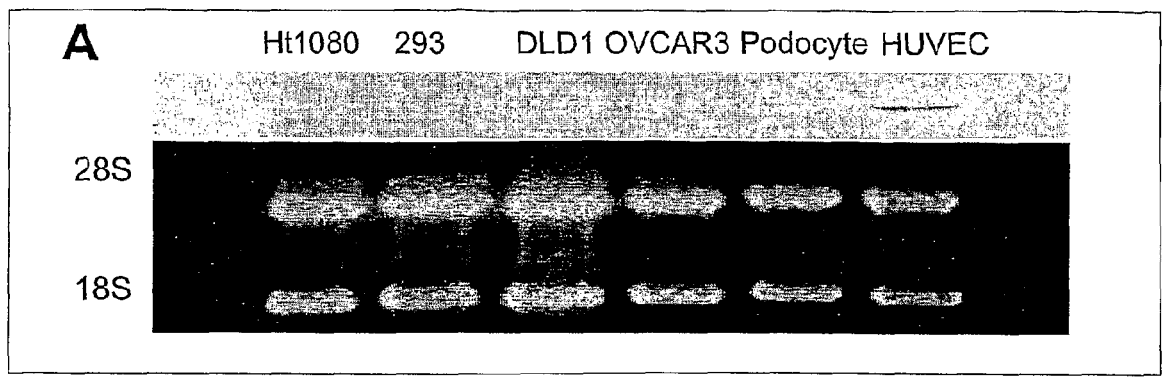
FIGS. 5A and 5B show the expression profile of human HspA12A and HspA12B in human cell lines.
Figure 5:
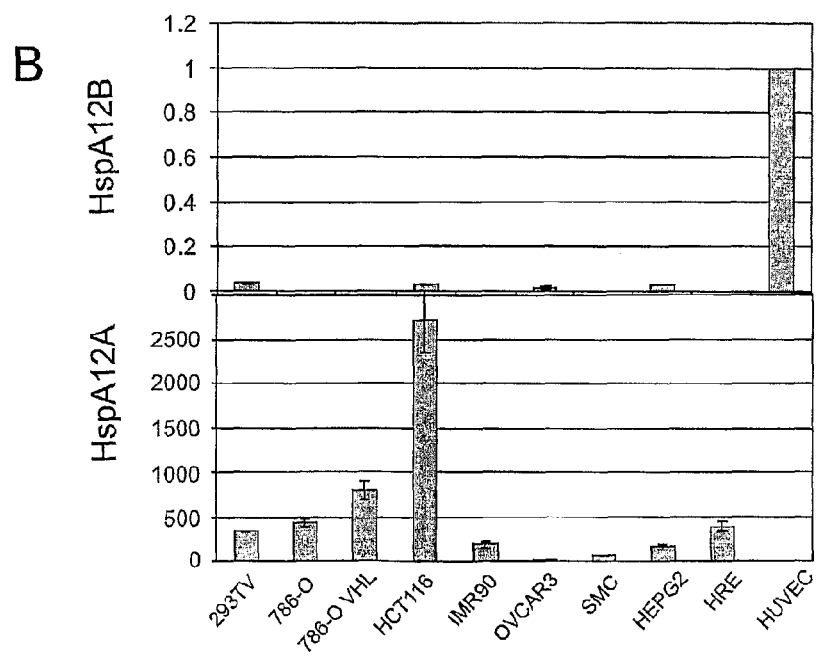

Northern blot analysis using the coding region of human HspA12B as a probe showed that HspA12B was present in HUVECs, and not detectable in HT1080 (fibrosarcoma cells), HEK 293, DLD1 (human colon cancer cells), OVCAR3 (ovarian cancer cells) and podocytes (FIG. 5A). Since HspA12A is closely related to HspA12B, we decided to compare the expression of HspA12B and HspA12A in a broader spectrum of cell lines by real-time PCR, which is more quantitative than Northern blot analysis. Similar to the results of our Northern blot analysis, the expression of HspA12B was highly specific to HUVECs (FIG. 5B), with the expression level 26 fold higher compared with the second highest expression cell line (293TV). Interestingly, the expression level of HspA12A in HUVECs was the lowest among all cell lines we checked. The second lowest expressor was OVCAR3 which was still 24.5 fold higher than that in HUVECs. These results were consistent with the endothelial specific expression pattern of HspA12B in zebrafish, and also suggested that the function and regulation of HspA12A and HspA12B were likely to be distinct, though they are similar in primary sequence.

Given the specific expression of HspA12B in endothelial cells, we proceeded to investigate its role in a number of angiogenesis assays in vitro.

Example 8

Knockdown and Overexpression of HspA12B in HUVECs

Figure 6:
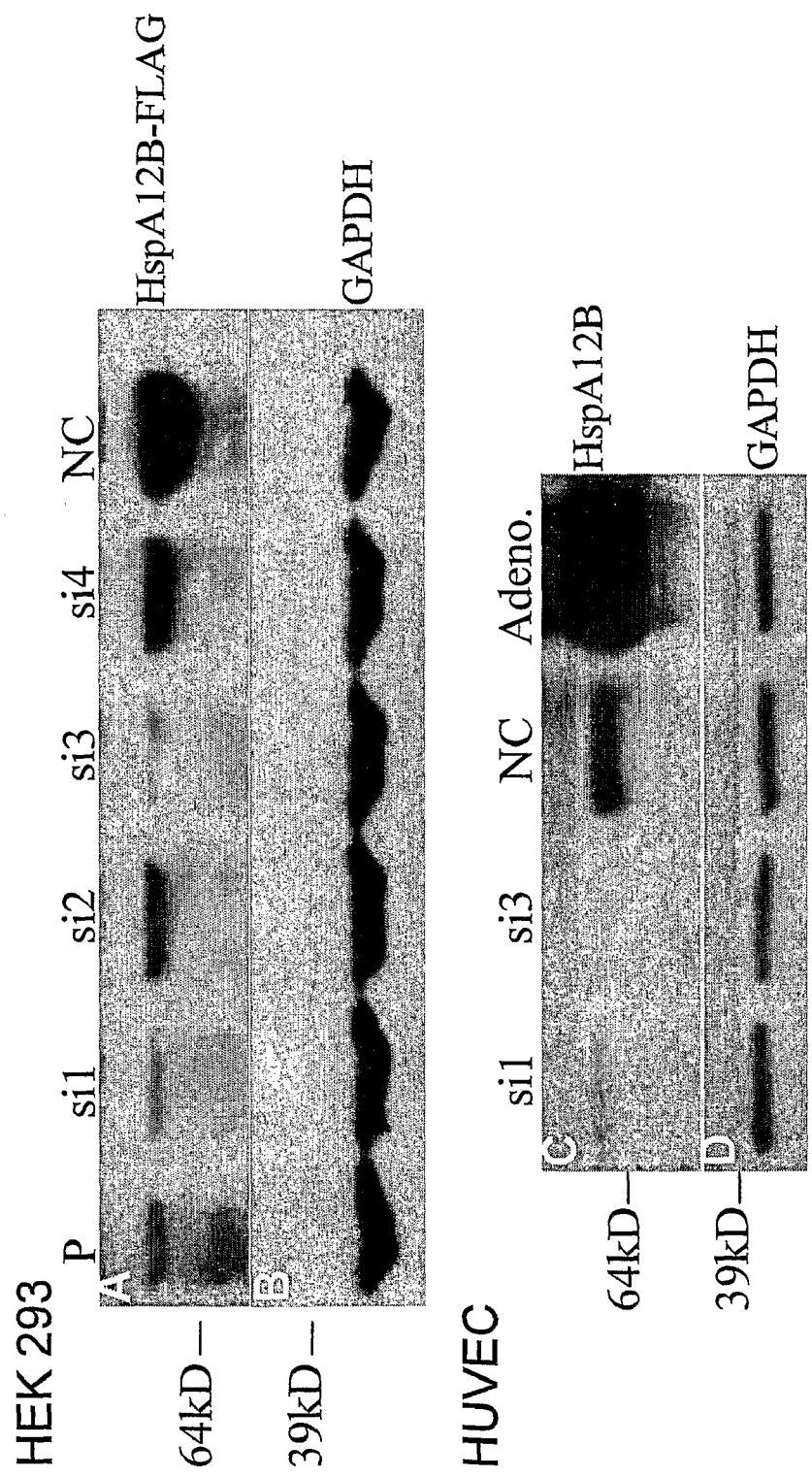
FIGS. 6A-6D shows the knockdown and overexpression of HspA12B.

To knockdown the expression of HspA12B in HUVECs, four siRNAs (si1 to 4) and a negative control siRNA (NC) were tested by cotransfecting them with pCS2+-HspA12B/C-FLAG with a ratio of 50:1 in HEK 293 cells and lysates collected 48 hours post-transfection were resolved by SDS-PAGE. Si1 and si3 knocked down the expression of HspA12B/C-FLAG to 13.8% and 8.2% compared with that of NC, respectively, while si2 and 4 were less effective (FIGS. 6A, B). Therefore, si1 and 3 were tested further in HUVECs. After transfecting these two siRNAs into HUVECs, si1 and 3 were—as expected from the transfection data in HEK293 cells-found to reduce endogenous expression by over 85% (FIGS. 6C, D), as assessed by a polyclonal antibody against HspA12B (Steagall et al., supra). Infection of HUVECs with HspA12B/C-FLAG adenovirus at a multiplicity of infection (MOI) of ~100 increased the expression level by ~5 fold compared with empty virus control (EV).

Example 9

Figure 7:
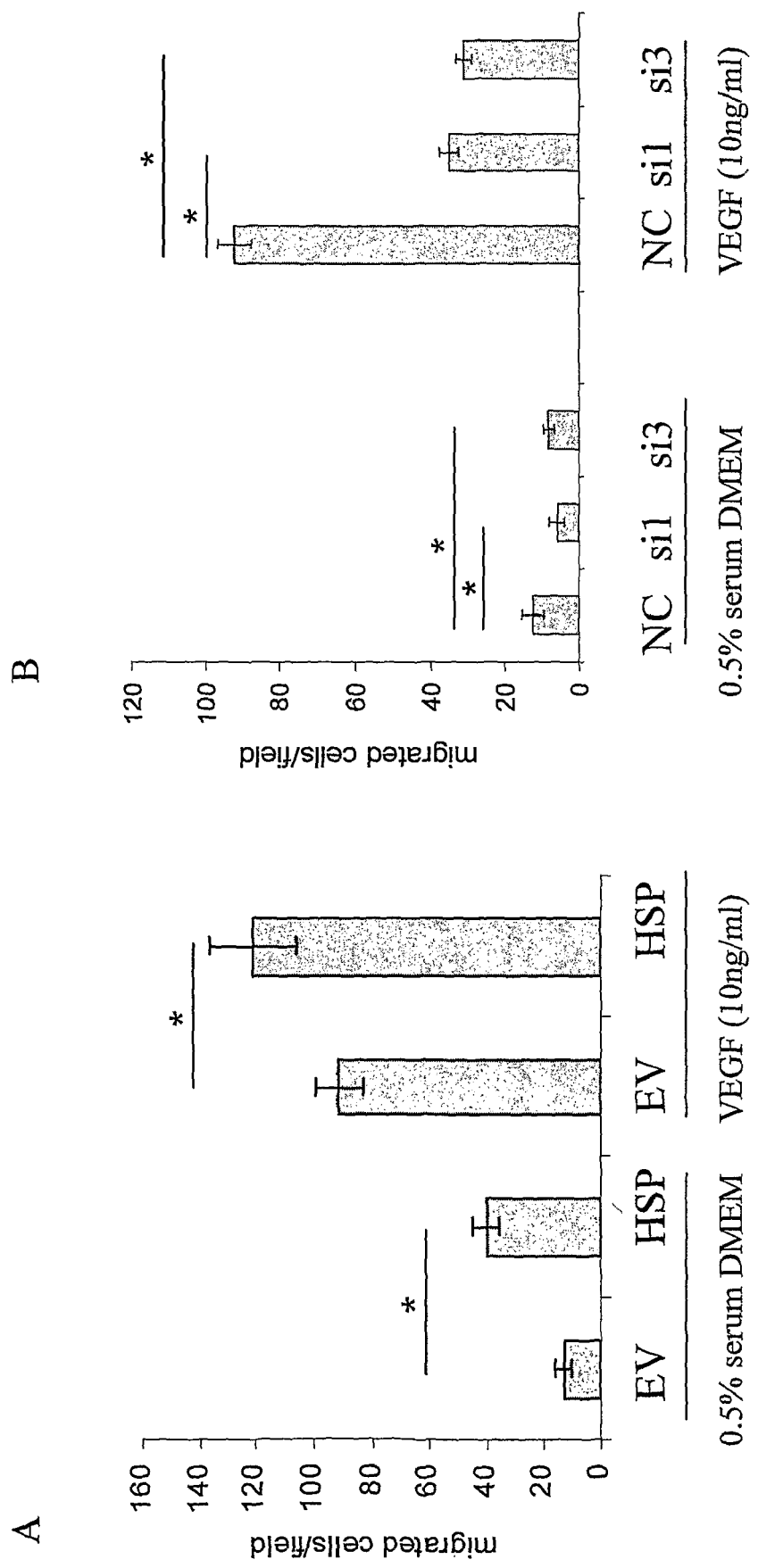
FIGS. 7A and 7B shows the effect of HspA12B on VEGF induced HUVEC migration.

HUVEC Migration is Augmented by Overexpressing HspA12B and Inhibited by HspA12B siRNAs In Vitro Since angiogenesis is a composite process in which cell migration plays a central role, we used HUVEC migration assay to test the role of HspA12B in this process. We found that cells overexpressing HspA12B via adenoviral mediated gene transfer migrated about 3 fold faster than controls cells infected with empty control adenovirus (FIG. 7A). Next, we redid our experiments under stimulation by vascular endothelial growth factor (VEGF), a potent and well-studied promigratory agent for endothelial cells (ECs). In the migration assay with 10 ng/ml VEGF, HspA12B augmented HUVEC migration was only 33% higher compared with empty virus (FIG. 7A), suggesting that HspA12B induced downstream signaling might overlap with those induced by VEGF. Conversely, the number of migrated cells from the si1 and si3 transfected HUVECs under VEGF stimulation was about 40% of that noted with cells transfected with NC (FIG. 7B), suggesting that HspA12B influenced VEGF signaling. Of importance, the use of si1 and si3 gave a similar phenotype, demonstrating that the phenotype was likely to be due to the knockdown of HspA12B expression. Si1 and si3 also had some effect in blocking baseline migration in 0.5% serum DMEM, suggesting that HspA12B may influence the "basal" migratory machinery (FIG. 7B).

Figure 8:
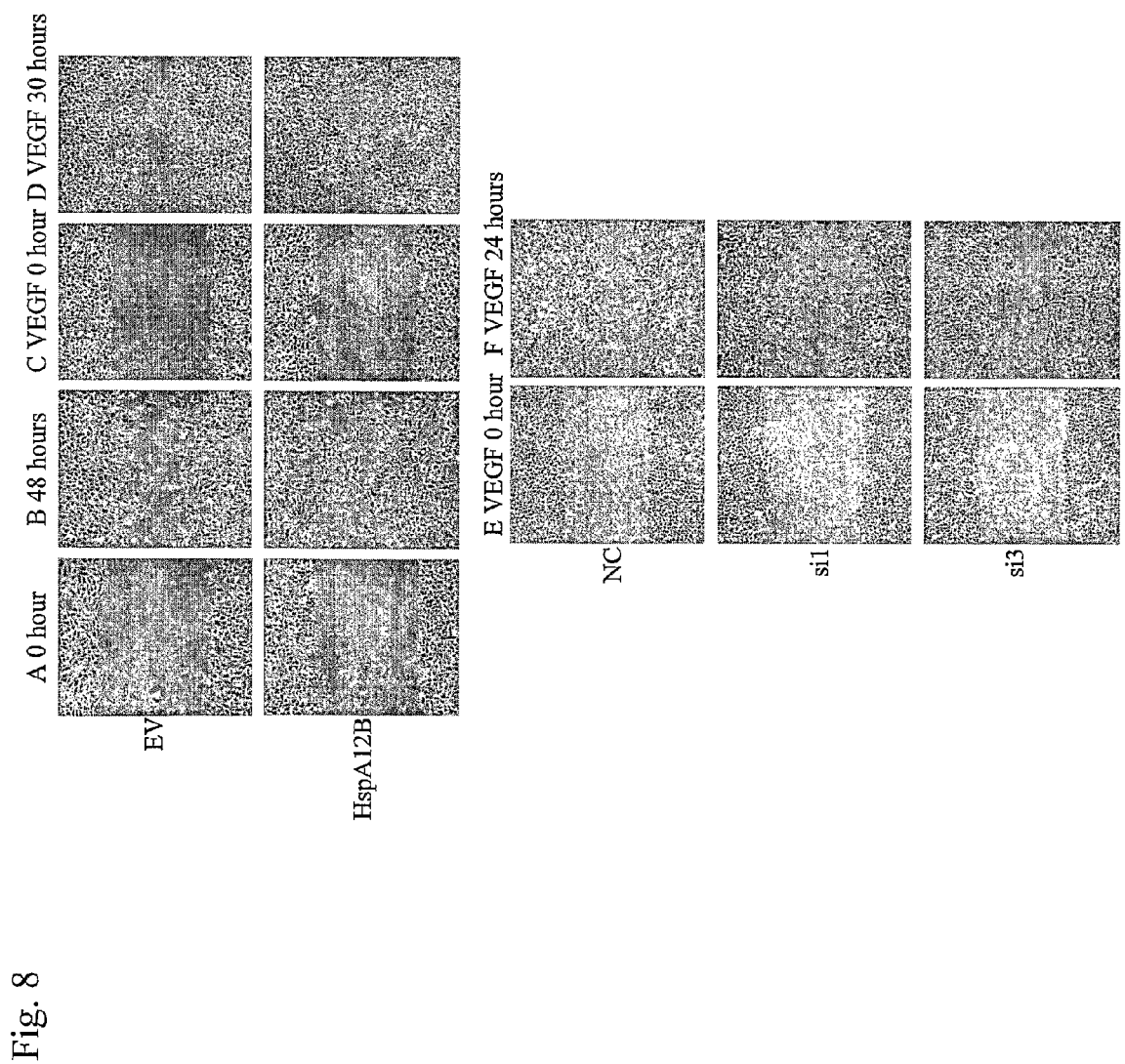
FIGS. 8A-8F show the results of wound healing assays using HUVECs.

To further study the effect of HspA12B on migratory responses, we used a wound healing assay to compare the motility of the HUVECs infected with sense adenovirus or transfected with siRNAs. HUVECs infected with sense and empty virus controls were grown to confluence on 6-well plates and wounds were made in the cell monolayer. EBM-2 with 1% serum (FIGS. 8 A, B) or EBM-21% serum plus VEGF (10 ng/nl) (FIGS. 8C, D, E, F) were used in the experiments. HspA12B strongly promoted wound closing in either conditions (FIGS. 8 A-D) and si1 and si3 transfection decreased wound closing (FIGS. 8E, 8F). These data were consistent with our migration assay results.

Example 10

Blocking of Tube Formation by siRNA Transfection into HUVECs

Figure 9:
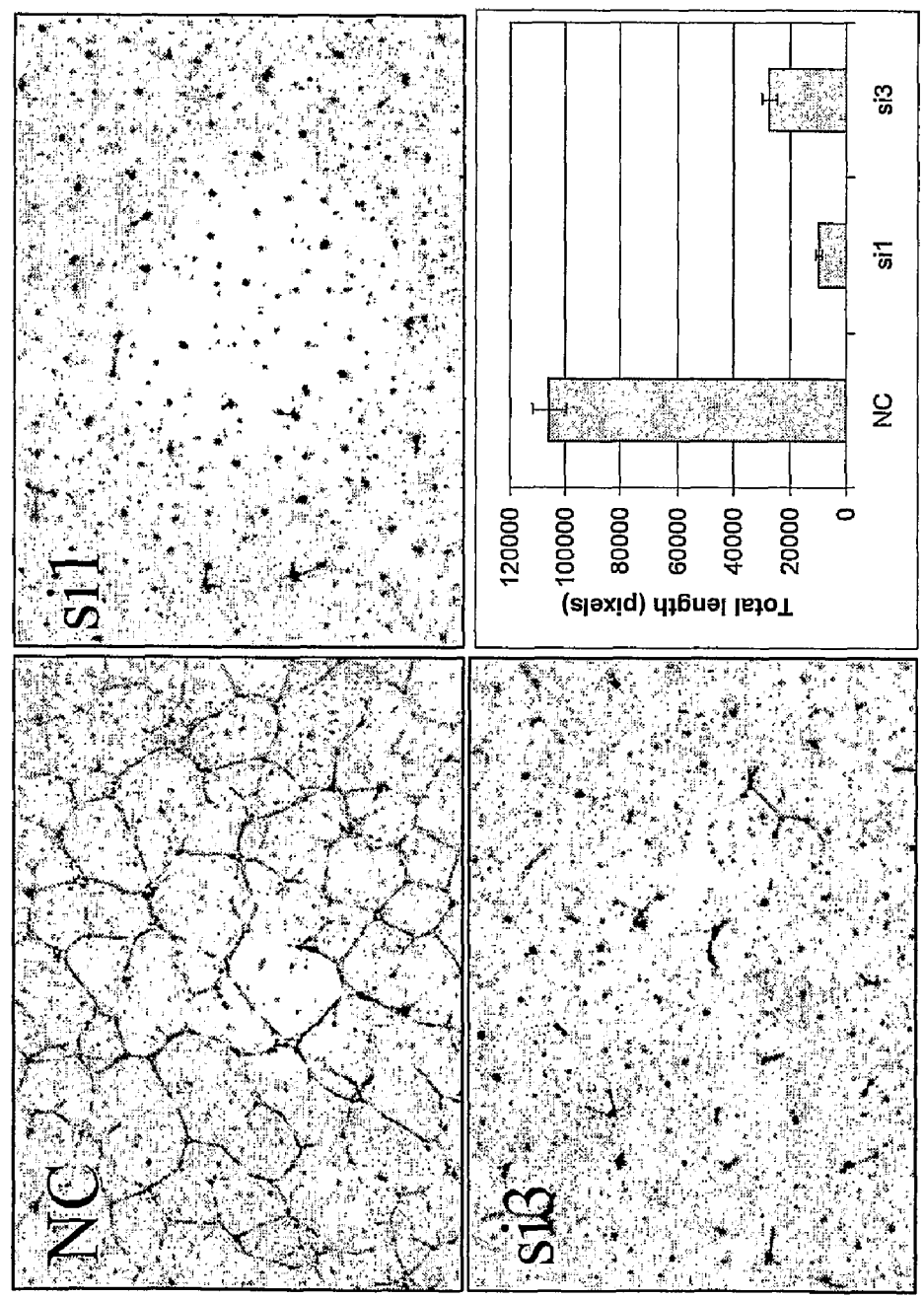
FIG. 9 shows the results of the HUVEC tube formation assay. HUVECs were transfected with NC, si1 and si3. After 48 hours, cells were trypsinized and resuspended in EBM-2 plus 2% serum and $4 \times 10^4$ cells were added to each well of a 48-well tissue culture plate with 100 μl solidified growth factor reduced Matrigel. Pictures were taken at 24 hours. Representative pictures were shown from five independent experiments. Quantitative data were shown as mean±s.e.m. All difference between groups were statistic significance ($p<0.05$) tested by two tailed student's t-Test.

The tube formation assay measures a number of functions of endothelial cells including cell survival, cell migration, the ability to connect to other endothelial cells and lumen formation. In this assay, we found that NC transfected HUVECs form well connected tube-like structures, whereas si1 and si3 transfected HUVECs barely formed tube-like structures, resembling the effect seen with potent antiangiogenic molecules (FIG. 9), and being consistent with our zebrafish phenotype.

Example 11

HspA12B is Necessary for Akt Phosphorylation in Endothelial Cells

To get more insight into HspA12B's function, we studied the effects of HspA12B siRNAs (si1 and si3) on Akt phosphorylation, known to be modulated by VEGF (Shiojima and Walsh, Circ. Res. 90:1243-1250 (2002)).

Figure 10:
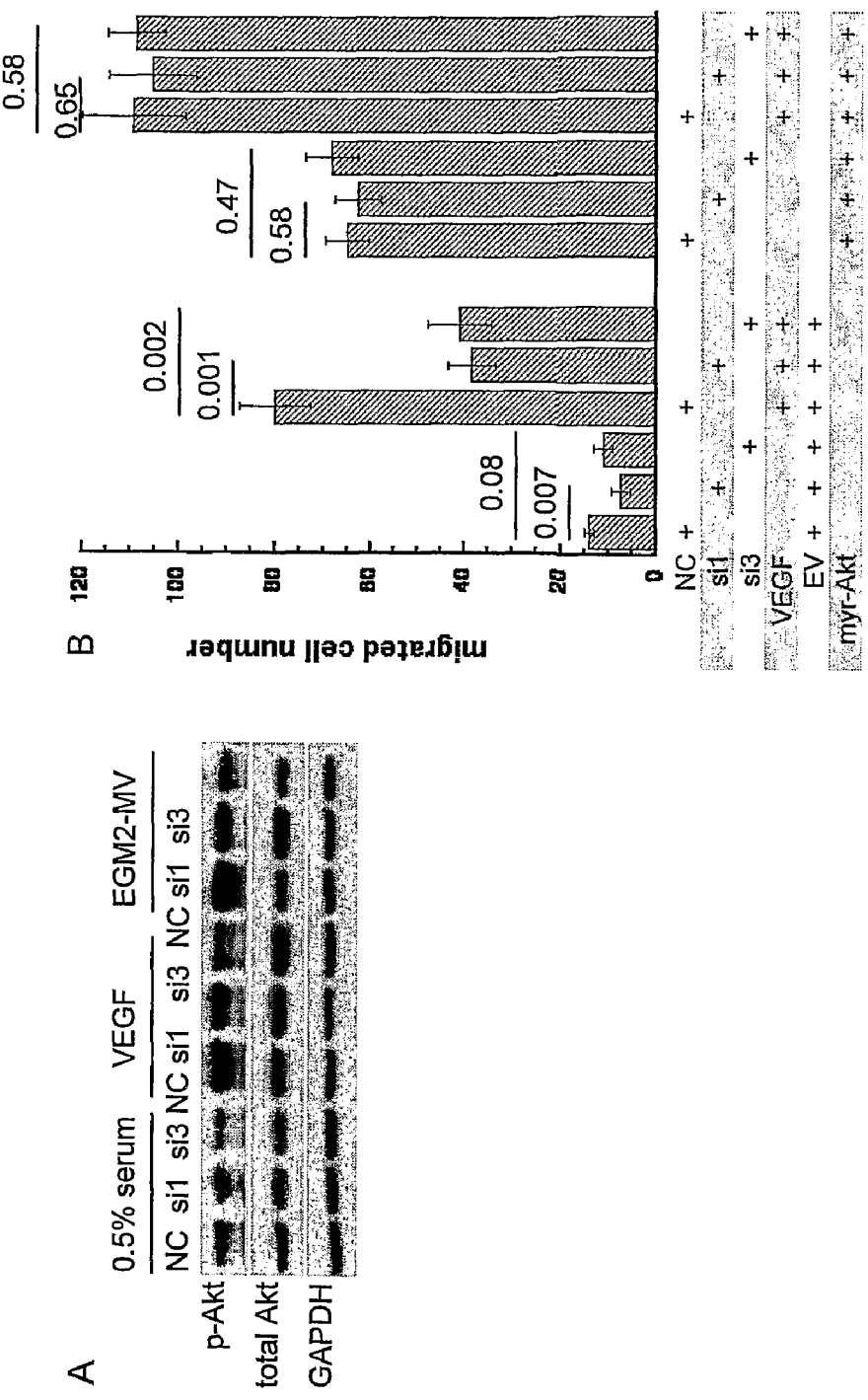
FIGS. 10A-10B show the western blot analysis of phosphorylation of Akt in cells transfected with siRNAs and HUVEC migration rescue experiment done with myr-Akt.

We found that si1 and si3 transfected HUVECs showed diminished phosphorylation levels of Akt in the presence of VEGF and even in normal serum conditions. In contrast, there was no significant change in total Akt (FIG. 10A). To ask whether diminished Akt phosphorylation might account for the effect on HUVEC migration of HspA12B siRNAs, we attempted to rescue this phenotype with a constitutively active Akt (myr-Akt). Indeed, the inhibitory effects of HspA12B siRNAs were abolished with myr-Akt (FIG. 10B).

Conclusions

Our whole-mount in situ screen enabled us to identify new genes that have expression specifically localized to vasculature without relying on any previous knowledge. Benefiting from various attributes of zebrafish vasculature development (e.g. transparency of the embryo, development of circulation in the first 48 hpf) and the availability of transgenic fish in which EGFP is expressed selectively in endothelial cells (Isogai et al., supra (2003)), (Lawson and Weinstein, supra (2002)), we could immediately gain insight into the function of these genes in vivo by using morpholino oligos as a tool for loss-of-function analysis. These in vivo results could then be further dissected and signalling pathways studied via in vitro assays in primary endothelial cells such as HUVECs, after identification of the HspA12B human orthologue using bioinformatics tools. By combining the advantages of both in vivo and in vitro systems, we have demonstrated a functionally important role for HspA12B in endothelial biology.

Not only have we demonstrated the endothelial cell specific expression of HspA12B, but we have also addressed the function of HspA12B in endothelial cells, We have addressed this question, first in vivo in fish and then in vitro in HUVECs and shown that the angiogenic potency of endothelial cells was greatly impaired in the absence of or with diminished expression of HspA12B. Knockdown of HspA12B expression using morpholino oligos in zebrafish compromised the sprouting of ISVs, the formation of intact DLAVs, and hampered the formation of SIVs and pectoral fin vessels; while knockdown of HspA12B in HUVECs by siRNAs led to inhibition of wound healing, migration and tube formation.

Knockdown of HspA12B reduced the phosphorylation of Akt under three different conditions but had little effect on the total level of Akt. Akt phosphorylation is one of the key events transducing multiple angiogenic signals, including those initiated by VEGF, Angiopoietin-1 and FGF-2. The attenuation of Akt phosphorylation could be one of the mechanisms by which knockdown of HspA12B expression blocks angiogenesis. Our results also suggest that reduction of phosphorylated Akt could at least account for the inhibitory effect of HspA12B siRNAs on the migration of HUVECs, since overexpression of myr-Akt, a constitutively active form of Akt could overcome these effects. However, we did not see such a rescue in the tube formation assay suggesting the existence of additional targets by which HspA12B affects tube formation.

We do not yet know if HspA12B is a heat inducible protein or what else induces its expression. Intriguing is the fact that it is rather uniquely expressed in endothelial cells, since Hsps are typically not cell or tissue specific, suggesting that it may play a unique role in protecting endothelium from "toxic" insults. For example, Hsp synthesis is known to be induced in all cell types in the blood vessel wall, including endothelial cells, upon exposure to environmental stress, heat, hormones, reactive oxygen species and sodium arsenite (Snoeckx et al., Physiol. Rev. 81:1461-1497 (2001)). However, HspA12B is constitutively expressed in endothelial cells, distantly related to the Hsp70 family and as yet we do not know if its expression can be modulated by heat shock or other insults. Aside from their roles as molecular chaperones and stress protecting proteins, Hsps are also being recognized as active components constitutively involved in many cellular processes. All proteins need to constantly change their conformation to be properly functional, often resulting in transient exposure of surfaces similar to those found in denatured proteins. By recognizing and associating with these surfaces to prevent undesirable protein interactions, Hsps facilitate many cellular processes, including cell signaling pathways. These results demonstrate the ability to induce HspA12B expression promotes endothelial health and can be used in the treatment of disorders in which there is evidence of endothelial dysfunction, e.g. atherosclerosis, sepsis, or pre-eclampsia. Similarly, inhibition of HspA12B expression or action (as could be undertaken by drugs that inhibit the binding of ATP to the putative ATP binding site of HspA12B) can be used to treat patients in which there is dysregulated angiogenesis, such as that occurs in cancer, or in ocular neovascularization processes, among others, especially if it is shown that HspA12B expression is augmented in these conditions. Finally, serum antibodies to HspA12B or the serum level of shed HspA12B may reflect the functional state of endothelium in humans.

In conclusion, the present study demonstrates that the HspA12B is selectively expressed in endothelial cells and is essential for both normal zebrafish vascular development in vivo and multiple endothelial cell functions in vitro.

Other Embodiments

From the foregoing description, it will be apparent that variations and modifications may be made to the invention described herein to adopt it to various usages and conditions. Such embodiments are also within the scope of the following claims.

All publications, patent applications, and patents, including U.S. provisional application No. 60/711,579, mentioned in this specification are herein incorporated by reference to the same extent as if each independent publication, patent application, or patent was specifically and individually indicated to be incorporated by reference.

From the foregoing description, one skilled in the art can easily ascertain the essential characteristics of this invention; can make various changes and modifications of the invention to adapt it to various usages and conditions. Thus, other embodiments are also within the claims.

What is claimed is:

1. A method of treating cancer in a subject, said method comprising administering to said subject a therapeutically effective amount of an HspA12B-specific antibody, or antibody fragment thereof, in an amount and for a time sufficient to treat or prevent said angiogenic disorder in said subject wherein said HspA12B-specific antibody or antibody fragment thereof is not cytotoxic, and wherein said HspA12B-specific antibody, or antibody fragment thereof, inhibits the biological activity of an HspA12B protein.

2. The method of claim 1, wherein said biological activity is ATPase activity, heat shock protein or chaperone activity, substrate binding, HspA12B-mediated phosphorylation of Akt, HspA12B-mediated activation of nitric oxide biological activity or expression levels.

3. The method of claim 1, wherein said HspA12B-specific antibody, or antibody fragment thereof specifically binds the ATP binding domain or the substrate-binding domain of HspA12B.

4. The method of claim 1, wherein said cancer is characterized by excessive proliferation, migration, or excess survival of endothelial cells.

5. The method of claim 1, wherein said HspA12B-specific antibody, or antibody fragment thereof, specifically binds to an epitope consisting of CVDVSTNRSVRAAIDFLSN (SEQ ID NO: 19).

6. A method of treating cancer in a subject, said method comprising administering to said subject a therapeutically effective amount of an HspA12B-specific antibody, or antibody fragment thereof, in an amount and for a time sufficient to treat said cancer in said subject, wherein said HspA12B-specific antibody or antibody fragment thereof specifically binds to an epitope consisting of CVDVSTNRSVRAAIDFLSN (SEQ ID NO: 19).

7. The method of claim 6, wherein said HspA12B-specific antibody, or antibody fragment thereof, inhibits the biological activity of an HspA12B protein.

8. The method of claim 7, wherein said biological activity is ATPase activity, heat shock protein or chaperone activity, substrate binding, HspA12B-mediated phosphorylation of Akt, HspA12B-mediated activation of nitric oxide biological activity or expression levels.

9. The method of claim 6, wherein said cancer is characterized by excessive proliferation, migration, or excess survival of endothelial cells.

\* \* \* \* \*

UNITED STATES PATENT AND TRADEMARK OFFICE
CERTIFICATE OF CORRECTION

| | | |
|---|---|---|
| PATENT NO. | : 8,329,175 B2 | Page 1 of 1 |
| APPLICATION NO. | : 11/990803 | |
| DATED | : December 11, 2012 | |
| INVENTOR(S) | : Sukhatme et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 633 days.

Signed and Sealed this
Twenty-sixth Day of August, 2014

Michelle K. Lee
*Deputy Director of the United States Patent and Trademark Office*